(12) United States Patent
Mamoun et al.

(10) Patent No.: US 9,546,371 B2
(45) Date of Patent: *Jan. 17, 2017

(54) CHIMERIC POLYNUCLEOTIDES AND POLYPEPTIDES ENABLING SECRETION OF A POLYPEPTIDE OF INTEREST IN ASSOCIATION WITH EXOSOMES AND USE THEREOF FOR THE PRODUCTION OF IMMUNOGENIC COMPOSITIONS

(75) Inventors: Robert Zaine El Abiddine Mamoun, St Andre de Sangonis (FR); Bernadette Nadine Trentin, St Andre de Sangonis (FR); Michel Vidal, Juvignac (FR)

(73) Assignees: CENTRE NATIONAL DE LA RECHERCHE SCIENTIFIQUE, Paris (FR); UNIVERSITE MONTPELLIER 2 SCIENCE ET TECHNIQUES, Montpellier (FR)

( * ) Notice: Subject to any disclaimer, the term of this patent is extended or adjusted under 35 U.S.C. 154(b) by 1122 days.

This patent is subject to a terminal disclaimer.

(21) Appl. No.: 12/933,403

(22) PCT Filed: Mar. 18, 2009

(86) PCT No.: PCT/EP2009/053221
§ 371 (c)(1),
(2), (4) Date: Dec. 20, 2010

(87) PCT Pub. No.: WO2009/115561
PCT Pub. Date: Sep. 24, 2009

(65) Prior Publication Data
US 2011/0268750 A1     Nov. 3, 2011

(30) Foreign Application Priority Data
Mar. 18, 2008 (FR) ..................... 08 01486

(51) Int. Cl.
*C07K 19/00* (2006.01)
*C12N 1/00* (2006.01)
*C12N 15/62* (2006.01)
*C12N 5/078* (2010.01)

(52) U.S. Cl.
CPC ......... *C12N 15/625* (2013.01); *C07K 2319/01* (2013.01); *C12N 5/0634* (2013.01)

(58) Field of Classification Search
CPC ................................ A61K 8/14; C12N 5/0639
See application file for complete search history.

(56) References Cited

U.S. PATENT DOCUMENTS

2011/0268750 A1   11/2011 Mamoun et al.

FOREIGN PATENT DOCUMENTS

| WO | WO-03/016522 A2 | 2/2003 |
|----|----|----|
| WO | WO-03/076603 A2 | 9/2003 |
| WO | WO-2004/073319 A2 | 8/2004 |
| WO | WO-2009/115561 A1 | 9/2009 |

OTHER PUBLICATIONS

Novakovic, S. et al., "Dileucine and YXXL motifs in the cytoplasmic tail of the bovine leukemia virus transmembrane envelope protein affect protein expression on the cell surface", Journal of Virology, vol. 78, No. 15, Aug. 2004, pp. 8301-8311, XP002508133.

Zeelenberg, I. S. et al., "Targeting tumor antigens to secreted membrane vesicles in vivo induces efficient antitumor immune responses", Cancer Research, vol. 68, No. 4, Feb. 2008, pp. 1228-1235, XP002508134.

Delcayre et al., "Exosome Display technology: Application to the development of new diagnostics and therapeutics", Blood Cells, Molecules and Diseases, vol. 35, No. 2, Sep. 2005, pp. 158-168.

Kuate, et al., "Exosomal vaccines containing the S protein of the SARS coronavirus induce high levels of neutralizing antibodies", Virology, vol. 362, No. 1, Apr. 2007, pp. 26-37.

Estelles, A. et al,, "Exosome nanovesicles displaying G protein-coupled receptors for drug discovery", International Journal of Nanomedicine 2007, vol. 2, No. 4, pp. 751-760.

DeGassart, A. et al,, "Exosomal sorting of the cytoplasmic domain of bovine leukemia virus TM Env protein", Cell Biology International, 2009, vol. 33, pp. 34-48, XP00253020.

Blanchard, Nicolas et al., "TCR activation of human T cells induces the production of exosomes bearing the TCR/CD3/zeta complex," Journal of Immunology, Apr. 1, 2002, vol. 168, No. 7, pp. 3235-3241.

(Continued)

*Primary Examiner* — Ronald Schwadron
(74) *Attorney, Agent, or Firm* — Birch, Stewart, Kolasch & Birch, LLP

(57) ABSTRACT

The present invention concerns a chimeric polypeptide comprising several polypeptide domains, which is capable of being secreted in association with membrane vesicles and in particular exosomes.

The present invention also concerns a polypeptide constituted by one of said domains for the secretion of a peptide or polypeptide of interest in association with membrane vesicles and in particular exosomes.

The invention also concerns the use of polypeptides of the invention and of polynucleotides coding for said polypeptides for the production of immunogenic compositions based on exosomes or based on DNA or for screening protein interactions.

The present invention also concerns exploiting the properties of exosomes comprising a polypeptide of the invention and of immunogenic compositions of the invention for the prophylaxis and/or treatment of an infection by a pathogenic agent, a pathogenic organism, a tumour antigen or a cytoplasmic antigen, in particular to elicit or promote, in vivo, in a host, in particular in a human or non-human mammal or a bird, a humoral and/or cellular response against a virus, bacterium, parasite or tumour.

21 Claims, 24 Drawing Sheets
(18 of 24 Drawing Sheet(s) Filed in Color)

(56) References Cited

OTHER PUBLICATIONS

Reuther, G. W. et al., "Analysis of Function and Regulation of Proteins That Mediate Signal Transduction by Use of Lipid-Modified Plasma Membrane-Targeting Sequences", Methods in Enzymology, vol. 237, pp. 331-350, (2000).

Silverman, L. et al., "Lysine Residues Form an Intergral Component of a Novel $NH_2$-terminal Membrane Targeting Motif for Myristylated $pp60^{v-src}$", Journal of Cell Biology, vol. 119, No. 2, pp. 415-425, (Oct. 1992).

Zitvogel, L., et al., "Eradication of established murine tumors using a novel cell-free vaccine: dendritic cell-derived exosomes," Nature Medicine, vol. 4, No. 5, pp. 594-600, (May 1998).

Colino, J., et al., "Exosomes from Bone Marrow Dendritic Cells Pulsed with Diptheria Toxiod Preferentially Induce Type 1 Antigen-Specific IgG Responses in Naive Recipients in the Absence of Free Antigen[1]," The Journal of Immunology, vol. 177, pp. 3757-3762, (2006).

Chaput, N., et al., "Exosome-based immunotherapy," Cancer Immunol. Immunother., vol. 53, pp. 234-239, (2004).

Pornillos, O., et al., "Mechanisms of enveloped RNA virus budding," TRENDS in Cell Biology, vol. 12, No. 12, pp. 569-579, (Dec. 2002).

Raposo, G., et al., "Human Macrophages Accumulate HIV-1 Particles in MHC II Compartments," Traffic, vol. 3, pp. 718-729, (2002).

Gould, S. J., et al., "The Trojan exosome hypothesis," PNAS, vol. 100, No. 19, pp. 10592-10597, (Sep. 16, 2003).

Cann, A. J., et al., "The Region of the Envelope Gene of Human Immunodeficiency Virus Type 1 Responsible for Determination of Cell Tropism," Journal of Virology, vol. 66, No. 1, pp. 305-309, (Jan. 1992).

Delamarre, L., et al., "The HTL V-I Envelope Glycoproteins: Structure and Functions," Journal of Acquired Immune Deficiency Syndromes and Human Retrovirology, vol. 13, Suppl. 1, pp. S85-S91, (1996).

Straub, OC, et al., "Bovine immunodeficiency virus and analogies with human immunodeficiency virus," Leukemia, vol. 13, Suppl. 1, pp. S106-S109, (1999).

De Gassart, A., et al., "Exosome Secretion: The Art of Reutilizing Nonrecycled Proteins?" Traffic, vol. 5, pp. 896-903, (2004).

Delcayre, A., et al., "Exosomes as novel therapeutic nanodevices," Current Opinion in Molecular Therapeutics, vol. 8, No. 1, pp. 31-38, (2006).

A

B

CHIMERIC POLYNUCLEOTIDES AND POLYPEPTIDES ENABLING SECRETION OF A POLYPEPTIDE OF INTEREST IN ASSOCIATION WITH EXOSOMES AND USE THEREOF FOR THE PRODUCTION OF IMMUNOGENIC COMPOSITIONS

This Application is the National Phase Under 35 U.S.C. §371 of PCT International Application No. PCT/EP2009/053221 which has an International filing date of Mar. 18, 2009, which claims priority to French Application No. 08/01486 filed on Mar. 18, 2008. The entire contents of all applications listed above are hereby incorporated by reference.

The invention relates to chimeric polypeptides and polynucleotides enabling, secretion of a polypeptide of interest in association with exosomes, and to their use in the production of immunogenic compositions based on DNA or on exosomes or for screening protein interactions.

The present invention pertains to a chimeric polypeptide which is capable of being secreted in association with exosomes when it is expressed in appropriate eukaryotic cells, said chimeric polypeptide comprising several polypeptide domains.

The present invention also pertains to a polypeptide constituted by one of these domains, for the secretion, in association with exosomes, of a peptide or a polypeptide of interest with which it is associated.

The invention also relates to a membrane vesicle, in particular an exosome, which comprises a polypeptide of the invention, to an immunogenic composition based on such exosomes and to a method for producing said exosomes.

The invention also pertains to a polynucleotide coding for a polypeptide of the invention and to an immunogenic composition comprising it, in particular a DNA vaccine comprising it.

The present invention also relates to exploiting the properties of membrane vesicles and immunogenic compositions of the invention for the prophylaxis and/or treatment of an infection by a pathogenic agent, a pathogenic organism, a tumour antigen or a cytoplasmic antigen, in particular to elicit or promote a humoral and/or cellular response against a virus, bacterium, parasite or tumour, in vivo in a host (human or non-human).

The present invention also envisages the use of membrane vesicles of the invention in order to produce antibodies directed against the peptide or the polypeptide of interest or in the context of a method for screening molecules interacting with the peptide or the polypeptide of interest.

Exosomes are in the form of small spheres bounded by a lipid bilayer. These membrane vesicles are secreted naturally by various types of cells, in particular by epithelial cells, tumour cells and certain cells of the immune system, (mastocytes, T and B lymphocytes, dendritic cells, especially Langerhans cells). Exosomes are distinguished from other membrane vesicles secreted by the cells notably by their small dimensions (50 to 100 nm in diameter) and by their membrane protein composition (adhesion, transport, signal transduction molecules and molecules of the major histocompatibility complex, inter alia).

Exosomes might in particular correspond to internal vesicles of multivesicular endosomes (in particular late endosomes) secreted by the cell during fusion of these endosomes with the plasma membrane; multivesicular endosomes are generally involved in the transport of molecules in the lysosomal compartments (the protein degradation pathway), but in certain cells such as reticulocytes and certain antigen-presenting cells, they may be directed to the plasma membrane with which they fuse to liberate exosomes into the extracellular medium.

Previous studies have demonstrated that exosomes are capable of inducing humoral and/or cellular immune responses (Delcayre et al, 2002). Exosomes are considered to be antigen vectors which are capable of directly stimulating T lymphocytes in vitro in a antigen-specific manner. Exosomes secreted by dendritic cells express molecules of the major histocompatibility complex (MHC), class I and II. Functional peptide/MHC complexes carried by the exosomes are transferred from one dendritic cell to another which has no experience of the antigen from which the peptides associated with the MHC molecules derives. By stimulating naïve dendritic cells progressively, one after the other, secreted exosomes having an antigenic peptide at their surface contribute to amplification of the specific T CD4 and T CD8 response (Delcayre and Le Pecq, 2006). As an example, when loaded with tumour peptides and injected into mice, these exosomes are capable of promoting a strong immune response and of causing solid pre-established tumours to regress (Zitvogel et al, 1998).

Exosomes are capable of presenting exogenic antigens either in the form of native full length proteins or in the form of peptides associated with MHC I and II molecules (Colino and Snapper 2006). The presentation of antigen at the surface of exosomes is similar to presentation at the membrane of a cell or an enveloped virus. However, since exosomes are neither alive nor infectious, they have the advantage of being capable of being manipulated like a normal substance without confinement precautions having to be taken, as would be the case with a virus. Thus, exosomes can be used as presenters of antigenic peptides or polypeptides for the, purposes of immunization. This technique, termed "exosome display", does not necessarily require the direct presentation of the antigen by the MHC (Chaput et al, 2004). However, the development of this novel vaccination technique assumes that an effective molecular "tool" is available which can be used to target the antigenic proteins to the exosomes. However, until now, such a "tool" has not been described.

The study of retroviruses, and more particularly human immunodeficiency virus (HIV), has shown that they have the capacity to misappropriate the cellular machinery of biogenesis of multivesicular endosomes in order to bud at the plasma membrane (Pornillos et al, 2002). These viruses can also use this machinery on the endosomal membrane level, its normal functional site. In macrophages, HIV buds at the membrane of multivesicular endosomes, which thus accumulate a large quantity of viral particles (Raposo et al, 2002). This discovery, associated with a comparative study of exosomes and HIV particles, has resulted in the "Trojan exosomes" hypothesis (Gould et al, 2003). In this hypothesis, viruses use the pre-existing pathway for exosome biogenesis for the formation of viral particles.

Further, the assembly site for the viruses could be of significant consequence to the pathogenicity and development of infection. In the case of HIV, it is currently known that infected macrophages constitute an important infectious reservoir. These cells in effect appear to be less susceptible to apoptosis normally induced by the presence of viral particles (Herbein et al, 2002); their viral production is less sensitive to antiviral drugs and the viruses appear to be capable of conserving their infectious power over long periods. The fact that HIV buds and accumulates in the multivesicular endosomes of these cells could thus be of major consequence to this type of infection.

Retroviruses are envelope viruses having a RNA genome and a replication cycle which is very particular since it makes use of reverse transcriptase, which transcribes the viral RNA genome into bicatenary DNA, and a viral integrase, which enables insertion of double stranded DNA into the genome of the infected cell.

The envelope of retroviruses is constituted by the outer envelope protein (SU) responsible for binding to the receptor of the target cell, and the trans-membrane glycoprotein (TM), responsible for fusion between the viral and cell membranes.

The envelope glycoproteins SU and TM derive from cleavage of the mature precursor protein termed ENV. Expression of the env gene results in synthesis of the envelope glycoproteins of the retroviruses in the form of a protein precursor which passes through the Golgi apparatus and then reaches the membrane portion (endosomal or plasma) which will act as a viral envelope during virion budding. Along the way, this oligomeric precursor is glycosylated and cleaved into surface (SU) and transmembrane (TM) glycoproteins. The SU and TM proteins remain associated and are anchored in the cell membrane via a hydrophobic transmembrane helix of the TM protein.

The envelope glycoproteins (SU and TM) play a major role in the retroviral multiplication cycle. Initiation of infection occurs by binding and fusion of the viral particle to the cellular plasma membrane. This binding is caused by SU binding to a specific receptor present on the surface of the target cell.

The TM glycoprotein of retroviruses has many facets due to association of its outer, transmembrane and cytoplasmic (CD™) domains, making it form the only protein of the retroviruses permitting communication either side of the membranes of the virus and the infected cell (Cann et al, 1992; Delamarre et al, 1996).

The TM protein is involved in the phenomenon of penetration of the virus into the target cell, by provoking fusion between the viral and cell membranes. It is also involved in the transmission of information between extra- and intracellular media. There is a structural dependency but also a functional dependency between the internal and external domains, which results in a transfer of information between these domains. Thus, the cytoplasmic domain can modulate the fusing activity of the TM protein, which, however, is carried by the external region of the molecule. In other cases, an external signal may be transduced via the CD™ to trigger activation of the cell. This shows that CD™ interacts more or less directly with proteins of the signal transduction machinery of the cell.

During its intracellular transit, the TM protein is susceptible of having an influence on the sorting, outcome, targeting and budding of the viral particles by interactions with the cytoskeleton as well as with the ubiquitation and budding machinery (Cann et al, 1992; Delamarre et al, 1996; Straub and Levy, 1999).

An earlier study suggested that the cytoplasmic domain of the TM protein of two retroviruses, bovine leukaemia virus (BLV), and HIV, can induce addressing and secretion of a recombinant protein in exosomes (De Gassart et al, 2004). Cells from the K562 line (an erythroleukaemic cell line of human origin), which secrete exosomes in a constitutive manner, were transfected with retroviral vectors which could express two types of chimeric protein in a eukaryotic system: (i) a chimera comprising the extracellular domain of the murine CD8 protein and the transmembrane and cytoplasmic domains of the TM glycoprotein of BLV (TM-BLV/CD8 chimera), and (ii) a chimera comprising the extracellular and transmembrane domains of the murine protein CD8 and the cytoplasmic domain of the TM protein of VIH (TM-HIV/CD8 chimera). The two chimeras are expressed both in the transfected K562 cells and in the exosomes secreted by these cells. In particular, expression of the chimeric TM -BLV/CD8 protein in the cells of the K562 line disappeared rapidly after transit through the trans-golgian network and the late endosomal compartments to end up in the exosomes secreted by these cells. It appears that the chimera comprising the cytoplasmic domain of the TM protein of BLV is more strongly addressed to the exosomes than the chimera comprising the cytoplasmic domain of the TM protein of HIV.

However, as the results presented in the examples section of the present application will show, exosomes carrying chimeric construct TM-BLV/CD8 described by De Gassart et al are only effectively produced in cells of the K562 line, and are only produced to a small extent or are not produced efficiently in other types of cells such as cells of the HEK293 line.

The invention concerns particular polypeptides which are distinguished from those described in the prior art and in particular from those described in De Gassart et al in that they enable addressing, in a much more effective manner, a peptide or a polypeptide of interest to the exosomes produced by cells of the HEK293 line and thus enable to very greatly amplify (10 to 100 times) the production of exosomes comprising said peptide or polypeptide of interest. Further, in contrast to the constructs described in De Gassart et al, which can only be effectively used in cells of the K562 line, these polypeptides can be addressed to the exosome membrane and secreted in association with membrane vesicles, in particular exosomes produced by different cell types, in particular HEK293 cells or T or B lymphocytes, and not uniquely by cells of the K562 line.

Thus, the present invention can in particular be used to produce large quantities of membrane vesicles, in particular exosomes, which can be used in immunization and in particular in vaccination. Such membrane vesicles (especially exosomes) could also be produced in vivo by a human or non-human host (in particular a human or non-human mammal or a bird) to be immunized, and in particular vaccinated, by administering to said host an immunogenic composition the active principle of which is a polynucleotide coding for a polypeptide of the invention, in particular an immunogenic composition based on DNA, and more particularly a DNA vaccine or an immunogenic composition the active principle of which consists of membrane vesicles (in particular exosomes) comprising a polypeptide of the invention.

In a first aspect, the present invention provides a chimeric polypeptide characterized in that it comprises or consists of the following domains:
  (i) a peptide or polypeptide of interest;
  (ii) a membrane domain having the capacity to become anchored in the lipid bilayer of a cell membrane; and
  (iii) a cytoplasmic domain (CD) of a membrane protein, which, in eukaryotic cells, enables addressing said chimeric polypeptide to the membrane vesicles, in particular to exosome-forming vesicles, and/or to the cell compartment(s) involved in the formation of the membrane vesicles, and in particular the exosome-forming vesicles, or a mutated derivative of said CD domain, the mutated domain being defined by substitution, deletion and/or insertion of one or several residue(s) in the sequence of the reference CD domain and said mutated derivative conserving the addressing capacity of the CD domain, the CD domain or its mutated derivative comprising at least one motif YxxL, in which Y represents a tyrosine residue, x represents any residue and L represents a leucine residue; and it being understood that when the CD domain and a membrane domain of said chimeric polypeptide are derived from the same protein, then at least the CD domain, its mutated derivative or the membrane domain derived from the same protein as the CD domain is a derivative mutated by substitution and/or deletion of one or several residue(s) in the sequence of the original domain.

Said chimeric polypeptide is in particular capable of being secreted in association with membrane vesicles, in particular with exosomes, when it is expressed in appropriate eukaryotic cells.

The invention concerns any chimeric polypeptide in which there exists at least one membrane domain positioned between the peptide or polypeptide of interest and the CD domain or its mutated derivative.

According to a preferred embodiment, domains (i) to (iii) are positioned in succession in the following order, from the N-terminal end to the C-terminal end in the chimeric polypeptide of the invention: peptide or polypeptide of interest— membrane domain—CD domain or its mutated derivative.

Alternatively, domains (i) to (iii) are positioned in the following order, for example: CD domain or its mutated derivative—membrane domain—peptide or polypeptide of interest.

The term "chimeric" herein denotes a polypeptide which associates several domains from at least two types which differ in their function and/or their cell localisation, at least two of said domains deriving from distinct molecules, in particular deriving either from different proteins of the same species or from different species or from the same protein from different species.

The term "domain" of a protein or a polypeptide means a region having a functional property for said protein or said polypeptide. Thus, the chimeric polypeptide of the invention comprises at least two different types of domains which are defined by their difference in cell localisation, when they are contained in the chimeric protein: one or several membrane domain(s) and a particular cytoplasmic domain.

The chimeric polypeptide of the invention necessarily comprises at least one membrane domain, but it may comprise several; the peptide or polypeptide of interest may comprise zero, one or several membrane domains (see below); the chimeric polypeptide of the invention comprises one or several membrane domains. When said chimeric polypeptide comprises only a single membrane domain, it may or may not be derived from the same entity, in particular from the same protein as the peptide or polypeptide of interest of the chimeric polypeptide of the invention.

A chimeric polypeptide of the invention may be the expression product of a recombinant polynucleotide and may be expressed in a recombinant manner in a host cell. Said chimeric polypeptide is thus a fusion polypeptide, for example.

The expression "membrane vesicle" as used in the present application denotes any vesicle composed of a lipid bilayer comprising a cytostolic fraction as produced by eukaryotic cells. This expression in particular includes vesicles secreted into the extracellular space, i.e. exosomes.

The term "exosomes" as used in the present application means nanovesicles of cell membranes as defined above. These exosomes may be purified from culture supernatants of cells by differential centrifugation, by ultrafiltration or by adsorption onto a support or by any other method, as will be seen in the examples The expression "secreted in association with membrane vesicles, in particular with exosomes" as used in the present application means that a chimeric polypeptide of the invention and/or at least one of its degradation products is secreted into the extracellular space, not in the soluble form, but in a form which is anchored in the membrane of the membrane vesicles, in particular exosomes. This anchoring is accomplished via the membrane domain(s) of said chimeric polypeptide or the membrane domain of a MHC (class I or II) molecule with which a degradation product of said chimeric polypeptide is associated. In a polypeptide that is so anchored in the membrane of a membrane vesicle (in particular an exosome), the peptide or polypeptide of interest may be exposed (completely or partially) outside said membrane vesicle, included (completely or partially) in the membrane of said membrane vesicle (this is the case when said polypeptide or peptide of interest comprises one or several membrane domains) and/or included (completely or partially) in the cytosolic fraction of said membrane vesicle.

According to a particular embodiment, the chimeric polypeptide of the invention is produced with and is integrated into the exosomes before they leave the cell.

The secretion of a peptide or polypeptide in association with membrane vesicles (in particular exosomes) requires in particular (1) addressing said peptide or polypeptide to the location(s) for formation of membrane vesicles and in particular exosomes, and (2) vesicular budding from the membrane in which said peptide or polypeptide is anchored.

The term "addressing", also termed "targeting", "sorting" or "intracellular routing" as used in the present application refers to the process which allows a peptide the synthesis of which commences in the cytosol to reach the compartments involved in the budding of membrane vesicles, in particular exosome-forming vesicles, and/or of reaching membrane vesicles, in particular exosome-forming vesicles.

Addressing a peptide or a polypeptide to the location(s) for formation of the membrane vesicles and in particular to the location(s) for formation of exosomes may in particular require that said peptide or polypeptide should include a signal peptide for importation into the endoplasmic reticulum, as will be explained below, so that said peptide or polypeptide can be inserted into a cell membrane, the membrane anchoring function being provided by the membrane domain.

The term "secretion" in the context of the invention means the process by which membrane vesicles, also termed "exosomes", are secreted, i.e. released from one or several cell(s) into the extracellular space. This process can in particular occur when multivesicular endosomes fuse with the plasma membrane of a cell, thereby releasing the membrane vesicles which they contain from the cell.

As will be shown in the examples below, a test for demonstrating the properties of addressing and secretion of a chimeric polypeptide of the invention consists of verifying that said chimeric polypeptide and/or its degradation products are indeed associated with membrane vesicles (in particular exosomes) when said polypeptide is expressed in appropriate eukaryotic cells.

An "appropriate" eukaryotic cell is advantageously a eukaryotic cell comprising internal vesicles for secretion, which can be cultivated, which is capable of exocytosis, which is genetically modifiable and, preferably, wherein the internal vesicles may be secreted under the effect of an external stimulus. In particular, it is a mammalian cell and more particularly a cell of human origin or a cell having a non-human mammal at its origin. It may also concern primary cultures or immortalized lines. Such "appropriate" eukaryotic cells in particular include eukaryotic cells which are naturally capable of producing exosomes, in particular mastocytes, T and B lymphocytes and dendritic cells (for example Langerhans cells) or cells derived from these cell types, as well as eukaryotic cells or eukaryotic cell lines modified by genetic engineering so as to render them capable of secreting exosomes.

The term "residue" as used in the present application refers to an amino acid residue. These residues are indicated using the abbreviated single letter code (for example, Y for a tyrosine residue, L for a leucine residue and P for a proline residue).

The term "lipid bilayer" denotes the basic structure of the plasma membrane and of any biological membrane, i.e. any assembly of amphiphilic lipids in a double sheet (or double layer) separating a cell or a vesicle from its environment and delimiting the cytoplasm of a cell or a vesicle, or delimiting the organites within the cytoplasm. This term thus encompasses any membrane of the cell, i.e. both the plasma membrane and the membranes of the various intracellular compartments, in particular those of the endoplasmic reticulum, those of the Golgi, or those of the membrane vesicles, for example that of the exosomes or endosomes.

The term "membrane domain" as used in the present application denotes any domain capable of interacting with a lipid bilayer and in particular capable of anchoring itself—and thus anchoring a polypeptide comprising it—in a lipid bilayer and in particular in a cell membrane and in the membrane of an exosome. According to a particular embodiment, this membrane domain is capable of binding to a first domain (for example a peptide or a polypeptide of interest) and also to a second domain (for example a cytoplasmic domain). As an example, it may comprise 10 to 50 residues, preferably 15 to 40 residues and more preferably 20 to 30 residues.

According to a particular embodiment, said membrane domain is a transmembrane domain, i.e. a membrane domain passing entirely through the lipid bilayer of a cell membrane. A transmembrane domain is generally arranged in hydrophobic α helixes; multiple pass transmembrane proteins may contain several, in particular 2, 3, 4, 5, 6, 7, 8, 9 or 10, or even more than 20 hydrophobic α helixes. It may also be arranged in β sheets. One or several transmembrane domains may also adopt a β transmembrane barrel structure, generally composed of 8 to 22 β strands.

According to a particular embodiment, said membrane domain does not have to pass entirely through the lipid bilayer of a cell membrane. This is the case, for example, with the membrane domain of a membrane protein in contact with just one of the compartments defined by said membrane. Said membrane domain may then, for example, be a hydrophobic helix parallel to the plane of the membrane or a hydrophobic loop.

Said membrane domain may be derived from one or several membrane proteins(s), in particular one or several transmembrane protein(s).

The term "membrane protein" means any polypeptide chain comprising one or several membrane domain(s) as defined above.

The expression "transmembrane protein" as used in the present application denotes any polypeptide chain which passes entirely through a cell membrane at least once, in particular the plasma membrane of a cell. This protein, which is in contact with the two compartments defined by the cell membrane through which it passes (for example with the extracellular space and the cytosol) thus comprises three types of domains, each being in contact with an environment with a different composition (for example, when the cell membrane which is passed through is the plasma membrane, the ectodomain(s) (or extracellular domain(s)), the transmembrane domain(s), and the cytoplasmic domain(s) are respectively in contact with the extracellular medium, the lipids of the plasma membrane and the cytosol): According to a particular embodiment, the transmembrane protein passes once through a cell membrane. According to another particular embodiment, the transmembrane protein passes through a cell membrane several times, in particular 2, 3, 4, 5, 6, 7, 8, 9 or 10, or even 20 or more times.

Said membrane or transmembrane proteins may in particular be selected from: human proteins, proteins of a non-human animal, proteins of a pathogenic organism or a pathogenic agent, in particular viral proteins, bacterial proteins or proteins expressed by a parasite or a tumour cell.

The or at least one of the membrane domain(s) of the chimeric polypeptide of the invention may in particular be that of one and the same membrane protein, or a mutated derivative of that domain. Said mutated derivative is defined by substitution, deletion and/or insertion of one or several residue(s) in the sequence of the reference membrane domain and conserves the capacity of this reference domain to become anchored in the lipid bilayer of a cell membrane. Said mutated derivative may, for example, be obtained by replacing a portion of the sequence of the reference domain by a sequence derived from the membrane domain of another membrane protein.

The term "derived from a particular protein" as used in the present application indicates that the peptide or polypeptide of interest comprises or consists of this particular protein or a fragment of said particular protein.

A "mutated derivative" of a membrane or cytoplasmic domain in the context of the present invention refers to any polypeptide or peptide modified with respect to the original or reference membrane or cytoplasmic domain, provided that this mutated derivative conserves the function of insertion, anchoring in a lipid bilayer normally attached to the reference membrane domain or the capacity of addressing normally associated with the reference cytoplasmic domain. Such a mutated derivative may thus, for example, correspond to a fragment composed of contiguous residues of said membrane or cytoplasmic domain (this derivative being obtained in particular by deletion and possibly substitution of one or several residue(s) into the original sequence) or, in contrast, a polypeptide with a larger size than the original membrane or cytoplasmic domain, in particular a polypeptide comprising the original membrane or cytoplasmic domain (this derivative being obtained in particular by insertion of one or several residue(s) into the original sequence).

According to a particular embodiment, the "mutated derivative of the membrane domain" in the context of the present application differs from the original sequence of the membrane domain by substitution of at least one residue, preferably one, two, three, four, five or even more than five residue(s), which may or may not be consecutive, in the sequence of the original membrane domain, said substitutions possibly being conservative, semi-conservative or non conservative, and/or by deletion and/or insertion of at least one residue, preferably one, two, three, four, five or even more than five residue(s), which may or may not be consecutive, in the sequence of the original domain. The sequence of said mutated derivative of the membrane domain may have at least 60% or 70%, in particular at least 80%, 90% or 95% similarity or identity with the membrane domain of the membrane protein from which it derives, with respect to the complete sequence of said membrane domain.

The term "percentage identity" as used in the present application means the number of identical residues with respect to the total number of residues of the peptide or polypeptide in question. The term "percentage similarity" defines the number of identical or chemically similar residues with respect to the total number of residues of the peptide or polypeptide being studied. The percentage identity or similarity is determined by aligning the two sequences to be compared and by using the Needleman and Wunsch algorithm, which allows overall alignment between two sequences. The percentage similarity or identity is then calculated based on the total length of these two sequences.

The term "cytoplasmic domain" (CD) as used in the present application means a particular cytoplasmic domain which is capable of being addressed to the membrane vesicles, in particular to the exosome-forming vesicles, or to the cell compartment(s) involved in the formation of the membrane vesicles, and in particular the exosome-forming vesicles in eukaryotic cells; this domain may thereby be secreted into the extracellular space in association with exosomes, when it is expressed in appropriate eukaryotic cells. Thus, when it is integrated into a chimeric polypeptide comprising a peptide or a polypeptide of interest, this domain enables addressing said chimeric polypeptide to the membrane vesicles and/or to their location(s) of formation and in particular to address said chimeric polypeptide to the membrane of membrane vesicles, such that said polypeptide can be secreted by a cell in association with the membrane vesicles (in particular exosomes), in particular an appropriate eukaryotic cell.

This CD domain comprises at least one motif YxxL, in which x represents any residue. In particular, it may comprise one, two or three YxxL motifs.

Said YxxL motif or one of the YxxL motifs of the CD domain may, for example, be the motif YINL (SEQ ID NO: 91) or YSHL (SEQ ID NO: 97). According to a particular embodiment, the CD domain comprises a motif DYxxL, in which x represents any residue. An example illustrated in the experimental section which may be cited is the motif DYINL (SEQ ID NO: 93).

Alternatively or in complementary manner, the CD domain comprises at least one motif equivalent to a motif YxxL (SEQ ID NO: 127), for example a motif YxxF (SEQ: ID NO: 130), in which x represents any residue. As an example, the transferrin receptor, which is a cellular protein, comprises such a domain.

Alternatively or in complementary manner, the CD domain comprises at least one motif equivalent to a motif DYxxL (SEQ ID NO: 128), for example a motif DYxxF (SEQ ID NO: 131), in which x represents any residue.

The description of the present application, made with reference to the YxxL domain in general or as illustrated in the particular sequences, is also applicable for the domains DYxxL or DYxxF, defined in general terms or having specific sequences derived from the examples of motifs which have been given.

According to a preferred embodiment, said CD domain further comprises at least one, in particular one, two, three or four motif(s) PxxP, in which x represents any residue. According to a particular embodiment, the motif PxxP or one of the motifs PxxP of the CD domain is the motif PSAP (SEQ ID NO: 88) or PTAP (SEQ ID NO: 89).

The general or specific description of the chimeric polypeptides of the invention, mentioning one or several motifs YxxL, is thus also applicable to chimeric polypeptides which further comprise a motif PxxP.

According to a particular embodiment, the CD domain comprises at least one motif YxxL or DYxxL (for example the motif YINL, YSHL or DYINL) and a motif PxxP (for example the motif PSAP or PTAP).

In particular, the CD domain consists of a sequence having a motif PxxP and a motif YxxL (or YxxF, DYxxL or DYxxF). In a particular embodiment of the invention, the motif PxxP of the CD domain is PSAP and the motif YxxL is YINL or YSHL.

In a particular embodiment, the motif YxxL of the CD domain (for example the motif YINL or YSHL), or one of the motifs, is YxxL, located in the C-terminal position with respect to the motif PxxP (for example the motif PSAP).

In a particular embodiment, the motif YxxL of the CD domain (for example the motif YINL or YSHL) is located in the N-terminal position with respect to the motif PxxP (for example the motif PSAP).

The proteins having a CD domain comprising at least one motif YxxL in particular include cellular proteins and viral proteins. These viral proteins are in particular proteins of enveloped viruses, in particular TM glycoproteins of enveloped viruses as defined above, or herpesvirus proteins, for example the protein LMP2-A of the Epstein-Barr virus which comprises at least two YxxL motifs.

According to a particular embodiment, the CD domain is that of a TM protein of a retrovirus. The term "retrovirus" as used here encompasses any retrovirus. This retrovirus may in particular be selected from the two sub-families of the following retroviruses, established on the basis of pathogenicity criteria:
  the Oncovirinae (Oncovirus), which are transforming viruses and which in particular include BLV which, in cattle, can induce a proliferation of B cells which can cause leukaemia, and the human T cell leukaemia virus (or HTLV-1);
  the lentivirinae (Lentivirus), which are cytopathogenic viruses, and which in particular include the human immunodeficiency virus VIH-1 and VIH-2.

By way of example, the CD domain may be that of a TM protein of a retrovirus selected from the bovine leukaemia virus (BLV), a human immunodeficiency virus (HIV), in particular HIV type 1 or HIV type 2, the human T cell leukaemia virus (HTLV), in particular HTLV-1 or HTLV-2, and the Mason-Pfizer monkey virus (MPMV).

According to a particular embodiment, the CD domain is that of the TM protein of BLV. This CD domain of BLV, which is composed of 58 residues, has the sequence SEQ ID NO: 6. Domain (iii) of the chimeric polypeptide of the invention then corresponds either to the domain of sequence SEQ ID NO: 6, or to a mutated derivative of the domain of sequence SEQ ID NO: 6.

In the particular case in which domain (iii) comprises or consists of the CD domain' of the TM protein of BLV, of sequence SEQ ID NO: 6, the membrane domain(s) of said chimeric polypeptide of the invention is(are) devoid of the membrane domain of the TM protein of BLV, which has the sequence SEQ ID NO: 4. A membrane domain of the chimeric polypeptide of the invention may however correspond to a mutated derivative of the domain of sequence SEQ ID NO: 4, said mutated derivative not including the sequence SEQ ID NO: 4. Such a mutated derivative may be obtained by deletion and possibly substitution of one or several residue(s) in the sequence SEQ ID NO: 4, as illustrated in the examples.

The term "mutated derivative of the CD domain" in the context of the present application encompasses at least one motif YxxL, in which x represents any residue. It may in particular comprise one, two or three YxxL motif(s). This mutated derivative may further comprise at least one, in particular one, two, three or four PxxP motif(s), in which x represents any residue. This mutated derivative differs from the original cytoplasmic domain by the substitution of at least one residue, preferably one, two, three, four, five, or even more than five residues, consecutive or not, in the sequence of the original cytoplasmic domain, these substitutions possibly being conservative, semi-conservative, or non-conservative, and/or by deletion and/or insertion of at least one residue, preferably one, two, three, four, five, or even more than five residues, consecutive or not, in the sequence of the original cytoplasmic domain.

In a particular embodiment of the invention, the mutated derivative of the CD domain is a fragment of native CD domain essentially constituted by a sequence of amino acids extending from the PSAP motif to the motif YxxL (for example YINL or YSHL) which, in a particular embodiment, follows it in the C-terminal part. If necessary, one or several amino acid residues naturally present in the CD domain, between these two motifs, is substituted or deleted.

According to a particular embodiment, the mutated derivative of the CD domain comprises at least one motif YxxF or DYxxL (for example the motif YINL, YSHL or DYINL) and a motif PxxP (for example the motif PSAP or PTAP), in which x represents any residue.

According to a particular embodiment, domain (iii) of the chimeric polypeptide of the invention, in particular the mutated derivative of the CD domain, is devoid of the sequence KCLTSRLLKLLRQ (SEQ ID NO: 126). Thus, the mutated derivative of the CD domain may differ from the original CD domain in that its sequence is devoid of the sequence: KCLLSRLLKLLRQ (SEQ ID NO: 126).

Further, or alternatively, the sequence of the mutated derivative of the CD domain may have at least 60% or 70%, in particular at least 80%, 90% or 95% similarity or identity with the sequence of the original CD domain devoid of the concatenation KCLTSRLLKLLRQ.

It may also be preferable for domain (iii) of the chimeric polypeptide of the invention, and in particular the mutated derivative of the CD domain, to be devoid of the sequence PC and/or of the sequence CP. According to a particular embodiment, said domain (iii), in particular the mutated derivative of the CD domain, is devoid of the sequence PCP. Thus, if the original CD domain contains a sequence PCP, its mutated derivative may in particular be obtained by deleting the cysteine residue of said sequence PCP in the sequence of the original CD domain, or by substituting it with another residue, preferably a non palmitoylable residue, for example an alanine residue.

According to a particular embodiment, the CD domain or its derivative is devoid both of the sequence PCP and of the concatenation KCLTSRLLKLLRQ.

When the or one of the membrane and cytoplasmic domain(s) derive from the same protein, in particular when they derive from the TM protein of BLV, it may be preferable to use as the domain (iii) a mutated derivative of the CD domain which is devoid of the sequence PCP and/or devoid of the sequence KCLTSRLLKLLRQ.

In the particular case in which one of the membrane domains of the chimeric polypeptide of the invention comprises or consists of the transmembrane domain of the TM protein of BLV, of sequence SEQ ID NO: 4, the CD domain or its mutated derivative is devoid of the CD domain of the TM protein of BLV, of sequence SEQ ID NO: 6. However, the CD domain or its mutated derivative may correspond to or comprise a mutated derivative of the domain of sequence SEQ ID NO: 6. As illustrated in the examples, such a mutated derivative may be obtained, for example, by deleting residues located in the N-terminal part of the sequence SEQ ID NO: 6, in particular by deleting the sequence KCLTSRLLKLLRQ and/or by deleting the sequence PCP in sequence SEQ ID NO: 6, or by substituting, for example, the cysteine residue of the sequence PCP with another residue, preferably with a non palmitoylable residue, for example an alanine residue.

By way of example, the mutated derivative of the CD domain of the TM protein of BLV may comprise or consist of the sequence SEQ ID NO: 8, which corresponds to the sequence SEQ ID NO: 6 in which the 13 N-terminal residues have been deleted.

Also by way of example, the sequence of the mutated derivative of the TM protein of BLV may differ from the sequence of the CD domain of the TM protein of BLV by substitution of at least one residue, preferably one, two, three, four, five, or even more than five residue(s), consecutive or not, and/or by deletion and/or insertion of at least one residue, preferably one, two, three, four, five, or even more than five residue(s), consecutive or not, in the sequence of said domain corresponding to the sequence SEQ ID NO: 8.

Again by way of example, the sequence of the mutated derivative of the CD domain of the TM protein of BLV (CD domain of sequence SEQ ID NO: 6) may have at least 60% or 70%, in particular at least 80%, 90% or 95% similarity or identity with the sequence SEQ ID NO: 8. Preferably, the sequence of said mutated derivative in particular conserves the motif YINL, YSHL (or, if appropriate, DYINL) and the motif PSAP of the sequence SEQ ID NO: 8.

The sequence of said mutated derivative of the CD domain of sequence SEQ ID NO: 6 is preferably devoid of the motifs PC (proline-cysteine) and CP (cysteine-proline), and more preferably devoid of the motif PCP (proline-cysteine-proline). For example, it may comprise or consist of the sequence SEQ ID NO: 10 or SEQ ID NO: 12.

According to a particular embodiment, the CD domain or its mutated derivative, in particular the mutated derivative of the CD domain of sequence SEQ ID NO: 6, comprises or consists of a sequence selected from the following sequences:

PxxPxxxxPxxPxSxYxxLxPxxPExYxxLxPxxPDYxxL;

PxxPx$_n$PxxPx$_n$SxYxxLx$_n$PxxPEx$_n$YxxLx$_n$PxxPDYxxL;

PxxPxxxxPxxPxSxYxxLxPxxPExYxxLxPxxPDYxxLxxxx; and

PxxPx$_n$PxxPx$_n$SxYxxLx$_n$PxxPEx$_n$YxxLx$_n$PxxPDYxxLxxxx;

in which x and x$_n$ respectively represent any residue and any one or several residue(s).

According to a particular embodiment, the CD domain or its mutated derivative, in particular the mutaded derivative of the CD domain of sequence SEQ ID NO: 6, comprises or consists of a sequence selected from the following sequences:

PxxPxxxxxxxxxxxxYxxL;

PxxPxxxxxxxxxxxxDYxxL;

PxxPxxYxxxxxxxxxYxxL;

PxxPxxYxxxxxxxxxDYxxL;

-continued

PxxPExYxxLxPxxPDYxxL;

PxxPx$_n$YxxL;

PxxPx$_n$DYxxL;

PxxPx$_n$Yx$_n$YxxL;

PxxPx$_n$Yx$_n$DYxxL;

PxxPEx$_n$YxxLx$_n$PxxPDYxxL;

PxxPxxxxPxxPxxxYxxLxPxxPExYxxLxPxxPDYxxL;

PxxPx$_n$PxxPx$_n$YxxLx$_n$PxxPEX$_n$YxxLx$_n$PxxPDYxxL;

PxxPxxxxPxxPxxxYxxLxPxxPExYxxLxPxxPDYxxLxxxx; and

PxxPx$_n$PxxPx$_n$YxxLx$_n$PxxPEX$_n$YxxLx$_n$PxxPDYxxLxxxx, in which x and x$_n$ respectively represent any residue and any one or several residue(s).

In particular, n is greater than or equal to 1 and less than 50. n may in particular have any value between 1 and 20.

By way of example, the motif PxxP which, in a particular embodiment, is in the N-terminal position in the sequences indicated above, may be the motif PSAP or PTAP.

Alternatively or in complementary manner, the motif YxxL which, in a particular embodiment, is in the C-terminal position in the sequences indicated above, may be the motif YINL or YSHL, for example.

In a particular embodiment of the invention, when the CD domain or its mutated derivative comprises one of the above sequences, the consecutive amino acid residues added upstream or downstream of this sequence do not form a motif PxxP, nor a motif YxxL, YxxF, DYxxL or DYxxF.

According to a particular embodiment, said mutated derivative of the CD domain of sequence SEQ ID NO: 6 comprises 6 to 100 residues, in particular 20 to 80, 30 to 70 or 40 to 60, for example 40, 41, 42, 43, 44, 45, 46, 47, 48, 49 or 50 residues.

By way of example, the sequence of the mutated derivative of the CD domain may comprise or consist of the sequence SEQ ID NO: 30, SEQ ID NO: 42, SEQ ID NO: 44 or SEQ ID NO: 95 or have at least 60% or 70%, in particular at least 80%, 90% or 95% similarity or identity with the sequence SEQ ID NO: 30, SEQ ID NO: 42, SEQ ID NO: 44 or SEQ ID NO: 95 with reference respectively to the complete sequence SEQ ID NO: 30, SEQ ID NO: 42, SEQ ID NO: 44 or SEQ ID NO: 95.

The term "peptide or polypeptide of interest" means the entire concatenation of several (at least two) successive residues, forming the structure of a peptide or a polypeptide. The term "peptide" denotes a chain of 2 to 20 successive residues (in particular 2, 3, 4, 5, 6, 7, 8, 9, 10, 11, 12, 13, 14, 15, 16, 17, 18, 19 or 20 residues), in particular a chain of 5 to 10, 10 to 15 or 15 to 20 successive residues. The term "polypeptide", which also denotes a protein or a fragment of a protein, is a concatenation of more than 20 (at least 21) successive residues, in particular a chain of 21 to 1000 successive residues, preferably 21 to 500, 21 to 250 or 21 to 150 successive residues, for example 21 to 50, 50 to 100, or 100 to 150 successive residues. Said peptide or polypeptide of interest may in particular comprise or consist of one or several domains of a soluble, membrane, transmembrane and/or multimeric protein.

According to a particular embodiment, said peptide or polypeptide of interest comprises or consists of one or several domain(s) of an extracellular protein or one or several fragment(s) of one or several of this(these) domain(s).

According to a particular embodiment, said peptide or polypeptide of interest comprises or consists of one or several ectodomain(s) and/or one or several membrane domain(s) and/or one or several cytoplasmic domains(s) of a membrane protein, in particular of a transmembrane protein, or one or several fragment(s) of one or several of this(these) domain(s).

According to a particular embodiment, said peptide or polypeptide of interest comprises or consists of one or several domain(s) of a cytosolic protein or one or several fragment(s) of this(these) domain(s).

In the present application, the term "fragment" of a domain means a portion composed of at least 6 contiguous residues of said domain, and in particular a portion having at least 50%, preferably at least 60%, 70%, 80%, or at least 90%, or even 100% identity with the complete sequence of said domain. Whatever it is, a fragment is smaller in size than that of the protein from which it derives.

According to a particular embodiment, said peptide or polypeptide of interest is antigenic, i.e. it is, capable of eliciting an immune response directed against said peptide or polypeptide of interest. Said peptide or polypeptide of interest may in particular comprise or consist of one or several epitope(s) of a protein.

According to a particular embodiment, said peptide or polypeptide of interest derives from a pathogenic organism, for example a virus, a bacterium or a parasite, or from a pathogenic agent, for example a cell tumour, a toxin, etc. Any peptide component of such an organism or pathogenic agent may be used, whether or not it is a structural protein. It may in particular be an antigen of a pathogen, and in particular a viral or bacterial antigen or an antigen deriving from a parasite.

Said peptide or polypeptide of interest may also derive from a tumour antigen, a cytoplasmic antigen, a transmembrane protein, in particular from an integrin or from a co-receptor or from a protein involved in interactions (in particular the proteins ICAM, CD4, CD8), from a ligand receptor, in particular a receptor with a single membrane domain, for example a cytokine receptor (in particular the receptors of the HER family responding to EGF, for example the receptor EGF-R1), in particular a receptor with multiple membrane domains, for example a receptor with seven transmembrane domains (in particular the receptor CXCR4 of VIH or a receptor of gamma amino butyric acid (GABA)), or a receptor ligand, in particular of a cytokine or from a fragment thereof.

Depending on the selected type of peptide or polypeptide of interest, the invention may be used in vivo, especially in immunization, in particular in vaccination, and/or in vitro, for example to screen molecules interacting with said peptide or polypeptide of interest (as described below).

According to a particular embodiment, said peptide or polypeptide of interest' derives from a protein present at the surface of a virus, for example a protein responsible for binding of a viral particle to a receptor located on a target cell and/or responsible for fusion of the viral envelope or the plasma membrane of a cell infected with the plasma membrane of a target cell, or a fragment of such a protein.

By way of example, it is possible to use, as the domain (i), a protein of the envelope of an enveloped virus or a fragment of this protein. This enveloped virus may in particular be selected from the following families:
- the Poxviridae, in particular those of the genus Orthopoxvirus, which in particular includes the smallpox virus and the vaccinia virus;
- the Herpesviridae, in particular those of the genus Herpesvirus, which in particular includes Herpesvirus types 1 and 2, the chicken pox virus, the Epstein Barr virus, Cytomegalovirus, and Herpesvirus types 6, 7, 8;
- the Hepadnaviridae, which in particular includes the hepatitis B virus;
- the Orthomyxoviridae, in particular those of the A, B or C influenza virus genus, which in particular includes the H5N1 avian influenza virus;
- the paramyxoviridae, in particular those of the genus Paramamyxovirus, which in particular includes the parainfluenzae virus and the mumps virus, those of the genus Morbillivirus, which in particular includes the measles virus, and those of the genus Pneumovirus, which in particular includes the syncytial respiratory virus;
- the Rhabdoviridae, in particular those of the genus Lyssavirus, which in particular includes the rabies virus;
- the Filoviridae, which in particular includes the Marburg virus and the Ebola virus;
- the Togaviridae, in particular those of the genus Flavivirus, which in particular includes the yellow fever virus and the hepatitis C virus (HCV), those of the genus Alphavirus and those of the genus Rubivirus, which in particular includes the Rubella virus;
- the Coronaviridae, in particular those of the genus Coronavirus, which in particular includes viruses responsible for respiratory and digestive infections such as severe acute respiratory syndrome (SARS);
- the Arenaviridae, in particular those of the genus Arenavirus, which in particular includes the Lassa virus;
- the Bunyaviridae, in particular those of the genus Bunyavirus, Hantavirus, Phlebovirus; and
- the Retroviridae, in particular those of the genus Lentivirus, which in particular includes the human immunodeficiency virus (VIH).

Again by way of example, the peptide or polypeptide of interest may be derived from a protein of the envelope of an influenza virus, in particular from the haemagglutinin (HA) of an influenza virus, and more particularly from the HA protein of the H5N1 avian influenza virus. It may be the ectodomain of this protein or a fragment of this ectodomain or a fragment comprising or consisting of one or several epitope(s) of this ectodomain.

Other antigenic polypeptides of these viruses may naturally be used, such as the protein or a fragment of the GAG polyprotein of VIH, the protein or a fragment of the capsid of poliovirus or of a papillomavirus.

Also by way of example, the peptide or polypeptide of interest may be derived from a protein of the external envelope of one of these viruses. It may be the envelope of one of these viruses. It may be the envelope of a coronavirus, in particular the Spike (S) protein of a coronavirus, and more particularly the Spike protein of a severe acute respiratory syndrome coronavirus (SARS-CoV). This peptide or polypeptide of interest may in particular comprise or consist of the ectodomain of this protein or a fragment comprising or consisting of one or several epitope(s) of this ectodomain.

According to a preferred embodiment, said peptide or polypeptide of interest is in its native conformation in the polypeptide of the invention.

According to a particular embodiment, the chimeric polypeptide of the invention further comprises at least one linking molecule (or linker). The term "linker" denotes any element enabling binding of two successive domains. It may be of variable length and nature.

According to a particular embodiment, at least two successive domains of the polypeptide of the invention are bound covalently, for example via peptide bonds. Thus, according to a particular embodiment, said linker is a polypeptide or a peptide. This polypeptide linker may consist of a sequence of 2 to 50 residues, preferably 2 to 30 residues, for example 2 to 5, 5 to 10, 10 to 20 or 20 to 30 successive residues.

According to a particular embodiment, the nucleotide sequence coding for said linker comprises or consists of a restriction site. The term "restriction site" means a particular nucleotide sequence recognized by a type II restriction enzyme as a cleavage site in the DNA molecule. Thus, this linker may, for example, be the linker of sequence RSR, encoded by the nucleotide sequence AGGTCTAGA, which comprises the restriction site for the restriction enzyme XbaI (sequence TCTAGA).

According to a particular embodiment, the chimeric polypeptide of the invention comprises one (or more) signal peptides for importation into the endoplasmic reticulum.

The term "signal peptide for importation into the endoplasmic reticulum>>, means a small continuous polypeptide sequence of approximately 5 to approximately 60 residues, in particular 15 to 60 residues and more particularly 15 to 30 residues, which allows a protein comprising it to pass through the membrane of the endoplasmic reticulum, the passage of the protein possibly being complete or partial; stopping of the passage of the protein is dependent on the presence of another additional signal (or signals). The signal peptides for the same destination are interchangeable from one protein to another, and so any signal peptide allowing the protein to be addressed to the endoplasmic reticulum may be used in the context of the present invention.

By way of example, it is possible to use, as the signal peptide for importation into the endoplasmic reticulum, a 27 residue peptide of sequence SEQ ID NO: 2.

Also by way of example, it is also possible to use, as the signal peptide for importation into the endoplasmic reticulum, the signal peptide of a membrane protein such as the proteins CD4, CD8 and haemagglutinin (HA), the signal peptide of a cytokine receptor such as IL1 R1, EGFR1 (HER1), HER2, HER3 or HER4, or the signal peptide of a secreted protein, for example, that of a cytokine. Thus, it is possible to use a signal peptide selected from: that of the human CD4 protein (peptide of sequence SEQ ID NO: 49) or the mouse CD4 protein (peptide of sequence SEQ ID NO: 50), that of the mouse CD8 alpha protein (peptide of sequence SEQ ID NO: 51), the bovine CD8 alpha protein (peptide of sequence SEQ ID NO: 52), the human CD8 alpha protein (peptide of sequence SEQ ID NO: 53), or the rat CD8 alpha protein (peptide of sequence SEQ ID NO: 54), that of the human Il1R1 receptor (peptide of sequence SEQ ID NO: 55), the human EGFR1 receptor (HER1) (peptide of sequence SEQ ID NO: 56), the human HER2 receptor (peptide of sequence SEQ ID NO: 57), the human HER3 receptor (peptide of sequence SEQ ID NO: 58) or the human HER4 receptor (peptide of sequence SEQ ID NO: 59), or that of the mouse IL-2 cytokine (peptide of sequence SEQ ID NO: 60), the mouse IL-6 cytokine (peptide of sequence SEQ ID NO: 61), the human IL-7 cytokine (peptide of sequence SEQ ID NO: 62), the mouse IL-10 cytokine (peptide of sequence SEQ ID NO: 63), or the human MIP-1-alpha chemokine (peptide of sequence SEQ ID NO: 64), that of the haemagglutinin of influenza B virus (peptide of sequence SEQ ID NO: 65), that of the haemagglutinin of influenza A H1N1 virus (peptide of sequence SEQ ID NO: 66), influenza A H2N2 virus (peptide of sequence SEQ ID NO: 67), H3N2 influenza A virus (peptide of sequence SEQ ID NO: 68), H4N6 influenza A virus (peptide of sequence SEQ ID NO: 69), H5N1 influenza A virus (peptide of sequence SEQ ID NO: 70), H6N5 influenza A virus (peptide of sequence SEQ ID NO: 71), H7N7 influenza A virus (peptide of sequence SEQ ID NO: 72), H8N4 influenza A virus (peptide of sequence SEQ ID NO: 73), H9N2 influenza A virus (peptide of sequence SEQ ID NO: 74), H10N7 influenza A virus (peptide of sequence SEQ ID NO: 75), H11N6 influenza A virus (peptide of sequence SEQ ID NO: 76), H12N5 influenza A virus (peptide of sequence SEQ ID NO: 77), or H13N6 influenza A virus (peptide of sequence SEQ ID NO: 78).

According to another particular embodiment, said signal peptide for importation into the endoplasmic reticulum may form part of the peptide or polypeptide of interest of the chimeric polypeptide of the invention. This is the case, for example, when said peptide or polypeptide of interest is a membrane protein or a cytokine.

Independently of or in combination with the above embodiment, said signal peptide for importation into the endoplasmic reticulum may form part of one of the membrane domains of the chimeric polypeptide of the invention. This may be the case, for example, when the membrane domain or one of the membrane domains of said polypeptide is derived from a receptor with seven transmembrane domains; it is in fact known in the art that for certain receptors with seven transmembrane domains, such as the receptor CXCR4, the transmembrane domain in the N-terminal position acts as a signal for importation into the endoplasmic reticulum. Do not put this in as it is occasionally carried out to augment membrane targeting.

Alternatively, according to another embodiment, said signal peptide for importation does not form part of either of the three domains (i), (ii) and (iii), and is consequently added in addition to the three domains (i), (ii) and (iii) of said chimeric polypeptide. It may then be placed at different localisations in the linear sequence of the chimeric polypeptide of the invention, but is generally at one end of said polypeptide and is preferably in the N-terminal position in said polypeptide.

If a second signal peptide for importation into the endoplasmic reticulum is added into the chimeric polypeptide of the invention, it can if necessary increase membrane targeting.

In the mature form, in particular when it is anchored in the membrane of a membrane vesicle, for example an exosome, the chimeric polypeptide of the invention generally has no or no more N- or C-terminal signal peptide for importation into the endoplasmic reticulum; after it has fulfilled its function, the N- or C-terminal signal peptide may be separated from the polypeptide by proteolytic cleavage, for example in the endoplasmic reticulum or in the Golgi.

According to a preferred embodiment, said peptide or polypeptide of interest is in its native conformation in the polypeptide of the invention.

According to a particular embodiment, said chimeric polypeptide is multimeric and in particular is in the form of a dimer or a trimer. This may in particular be the case when the peptide or the polypeptide of interest derives from a protein which, in its native form, dimerises or trimerises.

According to a particular embodiment, the chimeric polypeptide further comprises a tag sequence, which enables purifying the chimeric polypeptide. For example, said tag sequence may comprise or consist of a plurality of consecutively linked histidine residues, in particular a sequence of 6 consecutive histidine residues.

According to a particular embodiment, the chimeric polypeptide further comprises a marker for detecting the chimeric polypeptide by ELISA or Western Blot. Preferably, said marker is an epitope recognized by a specific monoclonal antibody, for example a myc epitope.

More particularly, the invention concerns a population of chimeric polypeptides, in particular chimeric polypeptides essentially glycosylated at the terminal stage, i.e. in the mature form, following their targeting and association with exosomes. Such a population is advantageously devoid of polypeptides which are glycosylated at early or intermediate stages of glycosylation.

In a particular embodiment of the invention, in the chimeric polypeptides, the peptide or polypeptide of interest advantageously has its native conformation (in particular it is in the form of a multimer, for example in the form of a dimer or trimer) when it is associated with exosomes.

The present invention also pertains to a polypeptide allowing the secretion of a peptide or polypeptide of interest with which it is associated, in association with membrane vesicles (in particular exosomes) when it is expressed in a eukaryotic cell, characterized in, that it comprises or consists of a mutated derivative of the CD domain of the TM protein of a retrovirus, said mutated derivative being defined by substitution, deletion and/or insertion of one or several residue(s) in the sequence of the reference CD domain and comprising at least one motif YxxL, in which Y represents a tyrosine residue, x represents any residue and L represents a leucine residue and said mutated derivative conserving the capacity of said CD domain to address a peptide or polypeptide of interest to the membrane vesicles, in particular to the exosome-forming vesicles, and/or to the cell compartment(s) involved in the formation of membrane vesicles, and in particular the exosome-forming vesicles.

The definitions given above in the context of the chimeric polypeptide of the invention also apply to this polypeptide by analogy.

According to a particular embodiment, said mutated derivative is a mutated derivative of the CD domain of the TM protein of BLV (CD domain of sequence SEQ ID NO: 6). This mutated derivative is as defined in the various aspects of the present invention concerning the chimeric polypeptide. Thus, said mutated derivative, which is generally devoid of the sequence KCLTSRLLKLLRQ and/or devoid of the peptide PCP, may comprise or consist of a sequence selected from the following sequences:

PxxPxxxxxxxxxxxxYxxL;

PxxPxxxxxxxxxxxDYxxL;

PxxPxxYxxxxxxxxxYxxL;

PxxPxxYxxxxxxxxDYxxL;

PxxPExYxxLxPxxPDYxxL;

PxxPx$_n$YxxL;

PxxPx$_n$DYxxL;

PxxPx$_n$Yx$_n$YxxL;

-continued

PxxPx$_n$Yx$_n$DYxxL;

PxxPEx$_n$YxxLx$_n$PxxPDYxxL;

PxxPxxxxPxxPxxxYxxLxPxxPExYxxLxPxxPDYxxL;

PxxPx$_n$PxxPx$_n$YxxLx$_n$PxxPEX$_n$YxxLx$_n$PxxPDYxxL;

PxxPxxxxPxPxxxYxxLxPxxPExYxxLxPxxPDYxxLxxxx;

PxxPx$_n$PxxPx$_n$YxxLx$_n$PxxPEX$_n$YxxLx$_n$PxxPDYxxLxxxx.

PxxPExxxPxKPDxDYxxLxPxxPExYxxLxPxxPDYxxLR;

PxxPEx$_n$PxKPDx$_n$DYxxLx$_n$PxxPEX$_n$YxxLx$_n$PxxPDYxxLR;

PxxPExxxPxKPDxDYxxLxPxxPExYxxLxPxxPDYxxLRxxxx and

PxxPEx$_n$PxKPDx$_n$DYxxLx$_n$PxxPEx$_n$YxxLx$_n$PxxPDYxxLRxxxx, in which x and x$_n$ respectively represent any residue and any one or several residue(s).

In particular, n is greater than or equal to 1 and less than 50 n may in particular have any value between 1 and 20.

By way of example, the motif PxxP which, in a particular embodiment, is in the N-terminal position in the sequences indicated above, may be the motif PSAP or PTAP.

Alternatively or in complementary manner, the motif YxxL which, in a particular embodiment, is in the C-terminal position in the sequences indicated above, may be the motif YINL or YSHL, for example.

In particular, this mutated CD derivative exclusively comprises the motifs PxxP and YxxL or DYxxL contained in the sequences described above.

According to a preferred embodiment, the mutated derivative of the CD domain of the polypeptide of the invention comprises at least one motif YxxL or DYxxL (for example the motif YINL, YSHL or DYINL) and a motif PxxP (for example the motif PSAP or PTAP) in which x represents any residue.

By way of example, the mutated derivative of the polypeptide of the invention may have the sequence SEQ ID NO: 30, SEQ ID NO: 42, SEQ ID NO: 44 or SEQ ID NO: 95 or have at least 60% or 70%, in particular at least 80%, 90% or 95% similarity or identity with the sequence SEQ ID NO: 30, SEQ ID NO: 42, SEQ ID NO: 44 or SEQ ID NO: 95 with reference respectively to the complete sequence SEQ ID NO: 30, SEQ ID NO: 42, SEQ ID NO: 44 or SEQ ID NO: 95.

More precisely, the mutated derivative of the polypeptide of the invention may have the sequence SEQ ID NO: 8 or have at least 60% or 70%, in particular at least 80%, 90% or 95% similarity or identity with the sequence SEQ ID NO: 8 by reference to the complete sequence SEQ ID NO: 8. For example, the sequence of said mutated derivative may comprise or consist of the sequence SEQ ID NO: 10 or SEQ ID NO: 12. Preferably, the sequence of said mutated derivative notably conserves the motif YINL or YSHL (or if appropriate DYINL) and the PSAP motif of the sequence SEQ ID NO: 8.

According to a particular embodiment, the polypeptide of the invention is further associated with or fused to a peptide or a polypeptide of interest.

The present invention also pertains to the use of a chimeric polypeptide of the invention or of a polypeptide of the invention as defined in the present application, to address (in vivo or in vitro) a peptide or polypeptide of interest to the membrane vesicles, in particular to the exosome-forming vesicles, and/or to the cell compartment(s) involved in formation of the membrane vesicles, and in particular exosome-forming vesicles, and to thereby allow secretion, by appropriate eukaryotic cells, of said peptide or polypeptide of interest in association with said membrane vesicles.

The present invention also pertains to a membrane vesicle, and more precisely an exosome, which comprises a chimeric polypeptide or a polypeptide of the invention as defined above, and/or one or several degradation product(s) of said chimeric polypeptide or of said polypeptide, this (these) degradation product(s) if necessary being associated with a molecule of the major histocompatibility complex (MHC) type I and/or type II.

The chimeric polypeptide or the polypeptide of the invention and/or their degradation product(s) is(are) anchored in the membrane of said membrane vesicle via their or one of their membrane domain(s) or via a membrane domain of the MHC (class I or II) molecule with which it is (they are) associated.

According to a particular embodiment, said degradation product comprises or consists of a fragment of the peptide or polypeptide of interest, in particular a fragment comprising or consisting of one or several epitope(s) of said peptide or polypeptide of interest.

According to a particular embodiment, the peptide or the polypeptide of interest or one of its fragments is exposed, partly or completely, at the surface, outside of the membrane vesicle. Thus, this membrane vesicle may in particular be used to produce or select, in vivo or in vitro, prokaryotic or eukaryotic cells or viruses (for example phages) or ribosomes interacting directly or indirectly with said peptide or polypeptide of interest or their fragment. This membrane vesicle may also be used to produce monoclonal or polyclonal antibodies in vivo or in vitro, for vaccination or not for vaccination, directed against said peptide or polypeptide of interest or fragment thereof. Such antibodies may in particular be used in diagnostics or to study protein interactions, in particular to carry out high throughput screening of molecules such as drugs or cytokines which are capable of interacting with the peptide or the polypeptide of interest or fragment thereof. Further, this membrane vesicle may be used in vivo, in immunization, to elicit or promote in a host (human or non-human) a humoral and/or cellular response against a tumour or against the virus, bacterium or parasite from which the peptide or the polypeptide of interest derives.

The immune response elicited or promoted by the membrane vesicle of the invention, in particular by an exosome of the invention, may be a tolerogenic or defensive response, depending on the nature of the polypeptides associated with the exosomes. A tolerogenic response may, for example, allow the host to combat asthma or accept a graft.

According to a preferred embodiment, said peptide or polypeptide of interest or fragment thereof is exposed (partly or completely) in its native conformation at the surface of the membrane vesicle.

According to a particular embodiment, the peptide or the polypeptide of interest or fragment thereof is partly or completely included in the membrane of the membrane vesicle of the invention, and/or partly or completely included in the cytosolic fraction of said membrane vesicle.

A pharmaceutical composition or an immunogenic composition, wherein the active principle comprises one or several membrane vesicle(s), in particular one or several exosome(s) as defined in the present application or one or several chimeric polypeptide(s) of the invention, one or several polypeptide(s) of the invention as defined above, also fall within the scope of the invention. Said composition further comprises one or several vehicle(s), diluent(s), and/or adjuvant(s) or one of their combinations. In the case of an injectable administration, a formulation in an aqueous, non-aqueous or isotonic solution may be selected.

In the present application, the term "vehicle" denotes any support (i.e. anything that can transport at least one active principle) which does not alter the efficiency of the biological activity of the active substances of the invention. Many vehicles are known in the art. For example, the vehicles used may be water, a saline solution, serum albumin, a Ringer solution, polyethylene glycol, water-miscible solvents, sugars, binders, excipients, pigments, vegetable or mineral oils, water-soluble polymers, surfactants, thickening or gelling agents, cosmetic agents, solubilizing agents, stabilization agents, preservatives, alkalinizing or acidifying agents, or one of their combinations.

The term "diluent" as used in the present application means a diluting agent, and includes soluble diluents and insoluble diluents. In general, an insoluble diluent is used when the active principle is soluble and a soluble diluent is used when the active principle is insoluble. An "insoluble" active principle may be completely insoluble in an aqueous medium or it may have a limited solubility (i.e. a solubility of less than 10mg/mL in 250 mL of water at a pH of 1.0 to 7.5) in aqueous medium. Examples of insoluble diluents include microcrystalline cellulose, silicon-containing microcrystalline cellulose, hydroxymethyl cellulose, dicalcium phosphate, calcium carbonate, calcium sulphate, magnesium carbonate, tricalcium phosphate, etc. Examples of soluble diluents include mannitol, glucose, sorbitol, maltose, dextrates, dextrins, dextrose, etc.

The term "adjuvant" in the present application denotes a product which, added to the contents of an immunogenic composition, in particular to a vaccine, increases the intensity of the immune reaction induced in the host (human or non-human) to which said composition is administered. An adjuvant may in particular increase the quantity of specific antibodies which said mammal is capable of producing after administration of said composition and thus increases the efficiency of immunization. The adjuvants are especially useful when the antigen alone can only provoke an immune reaction that is too weak to provide good protection, to reduce the quantity of antigen to be administered to a host, or to facilitate certain modes of administration of said composition, for example in the case of administration to the mucosae. In particular, the adjuvants that can be used in the context of the invention are saponins, aluminium phosphate (alum), peptidoglycans, carbohydrates, peptides, for example muramyl dipeptide (N-acetylmuramyl-L-alanyl-D-isoglutamine, MDP), oil/water emulsions, polysaccharides, cytokines, hormones, keyhole limpet haemocyanin, adjuvants from the family of non-methylated CpG dinucleotides, adjuvants from the poly IC family, adjuvants from the monophosphoryl lipid A family and nucleic acids, in particular bacterial DNA or DNA coding for a protein having an adjuvant effect, for example a growth factor or a cytokine, more particularly GM-CSF or IL4.

According to a preferred embodiment, said vehicle(s), diluent(s) and/or adjuvant(s) or a combination thereof are pharmaceutically acceptable substances or a combination of pharmaceutically acceptable substances, i.e. appropriate for administration to a host (for example a human, a non-human mammal or a bird) for therapeutic or prophylactic purposes. Such a substance or combination of substances is thus preferably non-toxic to the host to which it is administered.

The present invention also pertains to a polynucleotide characterized in that it codes for a chimeric polypeptide or for a polypeptide of the present invention, according to the universal genetic code, and considering the degeneracy of this code. The term "polynucleotide" encompasses any molecule of DNA or RNA (mono or bicatenary). This polynucleotide may be naked or, alternatively, it may be inserted in a cloning or expression vector, preferably a vector appropriate for expression in eukaryotic cells. This vector is preferably a plasmid. Said polynucleotide may in particular be assembled by PCR. It preferably comprises 2000 to 50000 nucleotides.

The term "code" does not necessarily mean that said polynucleotide comprises only the coding portion. Said polynucleotide may, in fact, further comprise sequences for regulation of expression and in particular comprise a promoter, for example a eukaryotic promoter.

By way of example, as the sequence coding for domain (iii) of the chimeric polypeptide of the invention, said polynucleotide comprises a sequence comprising or consisting of a sequence selected from the sequences SEQ ID NO: 5, SEQ ID NO: 7, SEQ ID NO: 9, SEQ ID NO: 11 SEQ ID NO: 47 and SEQ ID NO: 94.

According to a preferred embodiment, said polynucleotide comprises a sequence coding for a signal for importation into the endoplasmic reticulum. For example, this sequence may be the sequence SEQ ID NO: 1 or a sequence coding for a peptide of sequence SEQ ID NO: 49 to SEQ ID NO: 78. As indicated above; the signal peptide encoded by this sequence, when it is in the N- or C-terminal position in the polypeptide coded by said polypeptide, may be cleaved during a step for maturation of the chimeric polypeptide, which generally occurs in the endoplasmic reticulum or in the Golgi apparatus.

Said polynucleotide may be placed under the control of regulation, cloning or expression elements.

Thus, according to a particular embodiment, said polynucleotide is inserted into a cloning or expression vector, preferably an expression vector and more preferably a vector appropriate for expression in eukaryotic cells. Said vector is preferably a plasmid.

Said polynucleotide is in general placed under the control of a eukaryotic promoter, preferably a strong eukaryotic promoter such as a viral promoter, for example the promoter of a virus selected from: the SV40 virus, the Rous sarcoma virus, the murine leukaemia virus (MuLV), the human T-cell leukaemia virus (HTLV-I), the bovine leukaemia virus (BLV), the cytomegalovirus, a hybrid promoter derived from these viral promoters and a viral promoter containing modified sequences.

Said polynucleotide may further comprise a kozak sequence, in particular the nucleotide sequence ACCATGG, in which the sequence ATG corresponds to the start codon of the coding sequence.

Furthermore, said polynucleotide may further comprise an intron.

According to a particular embodiment, said polynucleotide comprises at least one nucleotide linker coding for a polypeptide linker as defined above. This nucleotide linker may in particular comprise or consist of a restriction site. The term "restriction site", means a particular nucleotide sequence recognized by a type II restriction enzyme as a cleavage site in the polynucleotide. By way of example, this nucleotide linker may consist of the nucleotide sequence AGGTCTAGA, which comprises the restriction site of the restriction enzyme XbaI (sequence TCTAGA).

According to a particular embodiment, the sequence of said polynucleotide is optimized for use in a host (for example a eukaryotic host), in particular a human being, a non-human mammal and/or a bird.

The present invention also pertains to a cloning or expression vector which is preferably a plasmid, characterized in that it comprises a polynucleotide insert constituted by a polynucleotide of the invention, under the control of regulation, cloning or expression elements.

The invention also pertains to a cell culture selected from the group comprising bacterial cell cultures, primary cell cultures of eukaryotic animal cells and cell lines, said cell culture containing a polynucleotide of the invention, a cloning or expression vector of the invention, or a chimeric polypeptide of the invention.

The present invention also pertains to an immunogenic composition comprising a nucleic acid, in particular a DNA, characterized in that it comprises or consists of a polynucleotide of the invention, and a pharmaceutically acceptable support, diluent or vehicle.

According to a particular embodiment, said immunogenic composition further comprises an adjuvant as defined in the present application.

According to a particular embodiment, said nucleic acid is a DNA. The DNA-based immunogenic compositions target cells of the host to be immunized in vivo, in particular dendritic cells (especially the Langerhans cells), which are excellent producers of vaccinating exosomes. Thus, this immunogenic composition may enable induction of the production, by the cells of a host immunized with said immunogenic composition, of exosomes carrying a peptide or polypeptide of interest or a fragment thereof.

According to a particular embodiment, said immunogenic composition is a vaccine, in particular a DNA vaccine.

The present invention also pertains to a recombinant exosome-producing cell, in particular a cell of the immune system and more particularly a cell of the immune system selected from mastocytes, lymphocytes, in particular B and T lymphocytes, and dendritic cells, in particular Langerhans cells, characterized in that it is recombined with one or several polynucleotide(s) of the invention, a cloning or expression vector of the invention or in that it has absorbed a membrane vesicle of the invention.

Further, the present invention also concerns a chimeric polypeptide of the invention, a polypeptide of the invention, one or several membrane vesicle(s) of the invention (in particular one or several exosome(s) of the invention), a polynucleotide of the invention or an immunogenic composition of the invention for use as a drug, in particular for use in prophylaxis and/or for treatment of a bacterial, viral or parasitic infection, or of a tumour. They are in particular intended for use in immunization, in particular to elicit or promote (i.e. in particular to amplify) in vivo, in a host (human or non-human) a humoral and/or cellular response against the tumour, virus, bacterium or parasite from which the peptide or polypeptide of interest derives. They may in particular be used in vivo to elicit or amplify a specific T CD4 and/or T CD8 response directed against the peptide or the polypeptide of interest and/or in order to produce polyclonal and/or monoclonal antibodies directed against the peptide or the polypeptide of interest, in particular antibodies directed against a peptide or a polypeptide comprising or consisting of one or several conformational epitopes.

The present invention also pertains to the use of a polypeptide of the invention (in particular a chimeric polypeptide of the invention), of one or several membrane vesicle(s) of the invention (in particular one or several exosome(s) of the invention), of a polynucleotide of the invention or of an immunogenic composition of the invention, for the production of a drug for prophylaxis and/or for treatment of a tumour or an infection by a pathogenic organism or by a pathogenic agent, in particular a bacterial, viral or parasitic infection.

Following administration of an immunogenic composition, the active principle of which is a polynucleotide of the invention or one or several membrane vesicle(s) of the invention, to a host (human or non-human), the exosome-producing cells of this host, in particular the dendritic cells, will produce exosomes comprising a chimeric polypeptide or a polypeptide of the invention and/or a degradation product of these latter polypeptides, this degradation product being liable to associate naturally with a molecule of the major histocompatibility complex. These membrane vesicles, in particular those on the surface to which the peptide or the polypeptide of interest or a fragment is (partly or completely) exposed, will elicit or promote an immune response directed against the peptide or the polypeptide of interest.

A "host" in the context of the present application denotes a human or a non-human animal.

The term " non-human animal" as used in the present application includes any non-human mammal, especially a rodent (in particular a mouse, a rat, a hamster or a rabbit), a monkey, a camel, a cat, a dog, a horse, a mule, cattle, a sheep, a pig, and also includes a bird, in particular a chicken.

The expression "infection" as used in the present application means that said host (human or non-human) has been exposed to a pathogenic organism or a pathogenic agent, in particular to an enveloped virus as defined in the present application. In particular, such an infection is capable of changing to show clinical signs of pathologies induced or accompanying said infection. The term "infection" thus also encompasses any clinical sign, symptom or disease appearing in a host (human or non-human) following exposure to a pathogenic organism or a pathogenic agent. As an example, a "viral infection" or a "bacterial infection" in the context of the present application includes both the earliest phases of the viral, bacterial or parasitic contamination, the intermediate phases, and the last phases of the contamination, as well as the various pathologies which are the consequence of the contamination of a host by a virus, by bacteria or by a parasite; it also includes the presence of all or part of the genome of a pathogenic organism.

The term "prophylaxis" denotes any degree of retardation in the time at which clinical signs or symptoms of infection or a tumour appears, as well as any degree of inhibition in the severity of the clinical signs or symptoms of infection or in the tumour, including but not limited to complete prevention of the infection or cancer. This requires that the polypeptides of the invention, the polynucleotide of the invention, the membrane vesicles or the immunogenic compositions of the invention are administered to the host that is susceptible of being exposed to a pathogenic organism or a pathogenic agent and/or susceptible of developing a tumour before the appearance of any clinical sign or symptom of disease. Prophylactic administration may take place before said host has been exposed to the organism or to the pathogenic agent responsible for infection, or at the moment of exposure. Such prophylactic administration serves to prevent and/or reduce the severity of any subsequent infection. Prophylaxis in the context of the present application also encompasses the total prevention of an infection or of a cancer.

The term "treatment", means the therapeutic effect, produced in a host, by the chimeric polypeptide, polypeptide, polynucleotide, membrane vesicles or one of the immunogenic compositions of the invention when they are administered to said host at the moment of exposure to an organism or a pathogenic agent, after exposure or after the appearance of clinical signs or symptoms of infection or after the appearance of a tumour. When the active substances of the invention are administered to a host after contamination by a virus, they may be administered during the primo-infection phase, during the asymptomatic phase or after the appearance of clinical signs or symptoms of the disease.

The term "treatment" includes any curative effect obtained because of an active substance of the invention, as well as an improvement in clinical signs or symptoms observed in the host (human or non-human), as well as an improvement in the condition of the host. Thus, the term "treatment" in particular encompasses slowing, diminution, interruption, as well as halting of a viral, bacterial or parasitic infection or of the growth of the tumour and/or the deleterious consequences of infection or of the appearance of the tumour; a treatment does not necessarily require the complete elimination of all of the clinical signs of infection or of the tumour and of all symptoms of the disease, nor the complete elimination of the virus, bacteria, parasites or tumour cells.

The active substances of the invention may thus be administered to a host presenting with risks of being exposed to an organism or a pathogenic agent and of developing an infection or a tumour (prophylaxis) or after exposure of the host to a pathogenic organism or agent, in particular after manifestation of the first clinical signs or symptoms of disease, for example after specific proteins or antibodies of a virus, bacteria, parasites or a tumour have been detected in the blood of the host (treatment).

The invention also pertains to a method for preventing and/or treating a viral, bacterial or parasitic infection or a tumour, said method comprising at least one step for administration in vivo, to a host requiring it, of the chimeric polypeptide or polypeptide of the invention, of one or several membrane vesicle(s) of the invention (in particular one or several exosome(s) of the invention), of a polynucleotide of the invention or of an immunogenic composition of the invention. Said treatment method is, in particular, appropriate for and intended to elicit or promote, in vivo, in said host, a humoral and/or cellular response against the tumour, the virus, the bacterium or the parasite from which the peptide or polypeptide of interest derives.

The terms "administration" and "administer" as used in the present application include any administration, regardless of the selected administration route.

The administration routes and posologies vary as a function of a variety of parameters, for example as a function of the state of the host, the type of infection and of the severity of infection to be treated or the size of the tumour.

The chimeric polypeptide or the polypeptide of the invention, as well as the one or several membrane vesicle(s) of the invention (in particular one or several exosome(s) of the invention), the polynucleotide of the invention or an immunogenic composition of the invention, are capable of being administered to a human or non-human host in the dry, solid (in particular as a wafer, powder, gelule, pill, granule, suppository, polymer capsule or tablet, and more precisely a rapid release tablet, gastroresistant tablet or delayed release tablet), in the gel form or in the form of a solution or as a liquid suspension (in particular a syrup, an injectable solution, infusion solution or drinkable solution, as nebulizers, microvesicles, or as liposomes) or in the form of a patch. These compounds may also be in the form of dry doses (powder, lyophilisate, etc) for reconstitution at the time of use with an appropriate diluent. Furthermore, they may be packaged in the form of a single dose (monodose) or multiple dose (multidose).

In order to enhance the beneficial effects of the immunogenic compositions of the invention, it is possible to carry out administration in the form of several successive administrations, repeated on one or more occasions, after a particular time interval. They may further be administered with a second therapeutic agent, in particular an antiviral, antibacterial, antiparasitic or antitumoral agent.

In the context of use in vaccination, it may also be preferable to immunize a host, initially with an immunogenic composition based on a polynucleotide of the invention, in particular with a DNA vaccine of the invention, then secondly with the membrane vesicles of the invention, an immunogenic composition based on said vesicles or an immunogenic composition wherein the active principle is a polypeptide of the invention, a chimeric polypeptide of the invention or one or several fragment(s) thereof (said polypeptide, chimeric polypeptide or its(their) fragment(s) possibly being obtained by purification or by chemical synthesis).

Alternatively, it may also be preferable to immunize a host, initially with the membrane vesicles of the invention or an immunogenic composition based on said vesicles, then secondly with an immunogenic composition based on a polynucleotide of the invention, in particular with a DNA vaccine of the invention.

The active substances of the invention may be formulated for administration enterally, parenterally (intravenously, intramuscularly or subcutaneously), transcutaneously (or transdermally or percutaneously), cutaneously, orally, mucosally, in particular per os, nasally, ophtalmically, otologically (into the ear), vaginally, rectally, or by intragastric, intracardiac, intraperitoneal, intrapulmonary or intratracheal delivery.

The immunogenic compositions based on a polynucleotide of the invention and in particular the DNA vaccines of the invention are preferably administered to a host intramuscularly or subcutaneously, using either a needle and syringe or a needle-free injector, in particular a compressed air gun that can propel microbeads of gold, tungsten or platinum loaded with DNA into the cells of a host ("biolistic" gun or gene gun), for example the "Helios® Gene Gun System" from the supplier BioRad.

The quantity of active principle administered to a human or non-human host is a therapeutically effective quantity, i.e. a quantity which is active, sufficient, in posologies and for periods of time that are necessary for a significant effect to be obtained and in particular for providing a significant benefit to the host in the context of administration for prophylaxis or treatment as defined in the present application. A therapeutically effective quantity is also a quantity whereby the beneficial effects outweigh any toxic or deleterious effect due to the active principle(s). Such a quantity may correspond to a quantity sufficient for inhibiting viral replication, bacterial proliferation or the significant growth of a tumour or to cause any existing infection provoked by the pathogenic organism or agent to disappear, reduce or improve. The therapeutically effective quantity varies as a function of factors such as the state of infection, age, sex or the weight of the host. The posological regimes may be adjusted in order to obtain an optimum therapeutic effect.

The present invention also pertains to a method for the in vivo production of membrane vesicles, in particular exosomes, characterized in that it comprises a step for administration of a polypeptide of the invention (in particular a chimeric polypeptide of the invention), one or several membrane vesicle(s) of the invention (in particular one or several exosome(s) of the invention), a polynucleotide of the invention or an immunogenic composition of the invention, to a host (human or non-human). This method may in particular be carried out in the context of a method for prophylaxis and/or treatment of a tumour or an infection by a pathogenic organism or by a pathogenic agent, in particular a bacterial, viral or parasitic infection.

The present invention further concerns a method for the in vitro production of membrane vesicles and in particular exosomes comprising a peptide or a polypeptide of interest and/or a degradation product of said peptide or polypeptide of interest, said degradation product possibly, if necessary, being able to associate with a molecule of the major histocompatibility complex. Said method comprises the following steps:
  a) introducing, into an exosome-producing cell, one or several polynucleotide(s) of the invention, which code(s) for a polypeptide comprising said peptide or polypeptide of interest, or bringing an exosome-producing cell into contact with one or several membrane vesicle(s) of the invention, which comprise(s) a polypeptide comprising said peptide or polypeptide of interest and/or a degradation product of this polypeptide, or with a composition based on said vesicles;
  b) culturing said exosome-producing cell;
  c) recovering the membrane vesicles and in particular the exosomes produced by said exosome-producing cell.

According to a particular embodiment, the exosome-producing cell is a cell of the line HEK293, or a derivative line, or a cell of the immune system. In particular, the cell of the immune system may be selected from mastocytes, lymphocytes, in particular T and B lymphocytes, and dendritic cells. The cell of the immune system is preferably a dendritic cell, for example a Langerhans cell.

According to a particular embodiment, step a) consists of bringing one or several membrane vesicle(s) of the invention, in particular one or several exosome(s) of the invention, into contact with a dendritic cell.

According to a particular embodiment, said method further comprises an intermediate step between steps a) and b), during which the cell is selected and/or stimulated to induce and/or increase the secretion of exosomes or to obtain exosomes having defined qualities, in particular to induce a specificity in the composition of the exosomes as regards certain cellular proteins, for example the protein ICAM.

According to a particular embodiment, the introduction of one or several polynucleotide(s) of the invention into an exosome-producing cell in step a) is carried out by transfection or by transduction.

According to a particular embodiment, step c) is carried out by purifying the membrane vesicles and in particular the exosomes, starting from a culture supernatant of the exosome-producing cell by differential centrifuging, by ultrafiltration, by adsorption onto a support, or by any other method.

The membrane vesicles and in particular the exosomes obtained by this method also fall within the scope of the invention.

The present invention also pertains to the use of one or several membrane vesicle(s) of the invention, or of an immunogenic composition based on membrane vesicle(s) of the invention, in order to produce antibodies directed against the peptide or polypeptide of interest, these antibodies being intended for use in diagnostics or in research.

The present invention also pertains to a method for preparing a polyclonal serum directed against one or several antigenic peptide(s) or polypeptide(s) of interest expressed on the surface of membrane vesicles, in particular of exosomes, said method comprising the following steps:
  a) administering to a non-human animal, if necessary repeated, membrane vesicles of the invention, an immunogenic composition of the invention or a polynucleotide of the invention, associated or not with an adjuvant; and
  b) recovering the antibodies formed, capable of recognizing the antigenic peptide(s) or polypeptide(s) of interest.

According to a particular embodiment, step a) is followed by a step for sacrifice of the non-human animal.

The present invention also pertains to two methods for preparing monoclonal antibody directed against one or several antigenic peptide(s) or polypeptide(s) expressed on the surface of membrane vesicles, in particular of exosomes. The first method comprises the following steps:
  a) fusing, with myeloma cells, spleen cells which have been previously obtained in a host (human or non-human), for example a Balb/c mouse, to which membrane vesicles of the invention, an immunogenic composition of the invention or a polynucleotide of the invention have been administered, if necessary in association with an adjuvant and if necessary by repeated administration;
  b) culturing and selecting hybridomas under conditions allowing the production of antibody;
  c) recovering monoclonal antibodies directed against the antigenic peptide(s) or polypeptide(s) of interest.

The second method for preparing monoclonal antibodies comprises the following steps:
  a) immortalizing antibody-producing cells, for example lymphocytes or lymphoblasts, from haematopoietic cells, more particularly from blood cells, which have been previously obtained in a host (human or non-human), for example a Balb/c mouse, to which membrane vesicles of the invention, an immunogenic composition of the invention or a polynucleotide of the invention have been administered, if necessary in association with an adjuvant and if necessary by repeated administration;
  b) culturing and selecting immortalized cells under conditions allowing the production of antibodies;
  c) recovering monoclonal antibodies directed against the antigenic peptide(s) or polypeptide(s) of interest.

The immortalization of antibody-producing cells in step a) may in particular be carried out by infecting these cells with an immortalizing virus. This immortalizing virus may be a herpes type virus, for example the Epstein-Barr virus. This immortalization may also be carried out by modification of the genome of antibody-producing cells with an immortalizing component. This immortalizing component may be a viral component, for example of a herpes type virus, or a cellular gene, for example the gene for telomerase.

The non-human animal to which membrane vesicles, an immunogenic composition or a polynucleotide of the invention have been administered in the context of a method for preparing a polyclonal serum or methods for preparing monoclonal antibodies may in particular be a rodent (in particular a mouse, for example a Balb/c mouse, a rat, a hamster or a rabbit), a bird, in particular a chicken, or a mule.

According to a particular embodiment of the two methods for preparing monoclonal antibodies of the invention, the spleen cells or the antibody-producing cells of step a) have been previously obtained in a non-human host following a step for sacrifice of said non-human animal.

If necessary, the monoclonal or polyclonal antibodies produced by the methods for preparing antibodies of the invention may be "humanized", i.e. modified by genetic engineering in order to replace the maximum number of constant fragments Fc of the original species by human fragments.

The present invention also pertains to the use of a chimeric polypeptide of the invention, a polypeptide of the invention, one or several membrane vesicle(s) of the invention or an immunogenic composition of the invention, for the detection (in particular in vitro) of specific partners which are capable of interacting with said peptide or polypeptide of interest or with a fragment of said peptide or polypeptide of interest.

The present application also concerns a method for in vitro screening of molecules or a method for selecting cells producing molecules interacting with a peptide or a polypeptide of interest or with a fragment of said peptide or polypeptide of interest, said method comprising:

a) bringing membrane vesicles of the invention into contact with one or several molecules susceptible of interacting with said peptide or polypeptide of interest;

b) detecting any interaction between said peptide or polypeptide of interest or a fragment of said peptide or polypeptide of interest and said molecules.

The interactions between said peptide or polypeptide of interest and any partner can be demonstrated in vitro by any technique that can demonstrate protein interactions and in particular between a protein and its ligand, for example by co-immunoprecipitation experiments, for example by ELISA, for example flow cytofluorimetry, for example by PAGE-SDS electrophoresis or by transfer of the "Western" (Western Blot) type, as well as by any high throughput screening technique that can demonstrate protein interactions, in particular between a protein and its ligand, for example techniques measuring inositol phosphate or by cAMP, or calcium modifications, or energy transfers (for example the FRET or BRET technique) between molecules or between two domains of molecules.

According to a particular embodiment, the membrane vesicles used in step a) of the screening method of the invention are such that at least one peptide or polypeptide of interest or at least one of their fragments is exposed, partly or completely, on the outside of said membrane vesicle. Said peptide or polypeptide of interest may in particular be a receptor with multiple transmembrane domains, for example the receptor CXCR4 or a receptor comprising a single transmembrane domain, for example the CD4 or EGF-R1 receptor.

Finally, the present invention also pertains to a kit comprising a polynucleotide of the invention and instructions for use.

Other characteristics and advantages of the present invention will become apparent from the examples and Figures below.

DESCRIPTION OF THE FIGURES

The patent or application file contains at least one drawing executed in color. Copies of this patent or patent application publication with color drawing(s) will be provided by the office upon request and payment of the necessary fee.

The bands corresponding to super-coiled plasmid DNA are framed. A: DNA obtained by the STET method and deposited on the column. E and E': Fractions retained on the column then eluted. FT: Non-retained fraction. M: Size marker.

Figure 5:
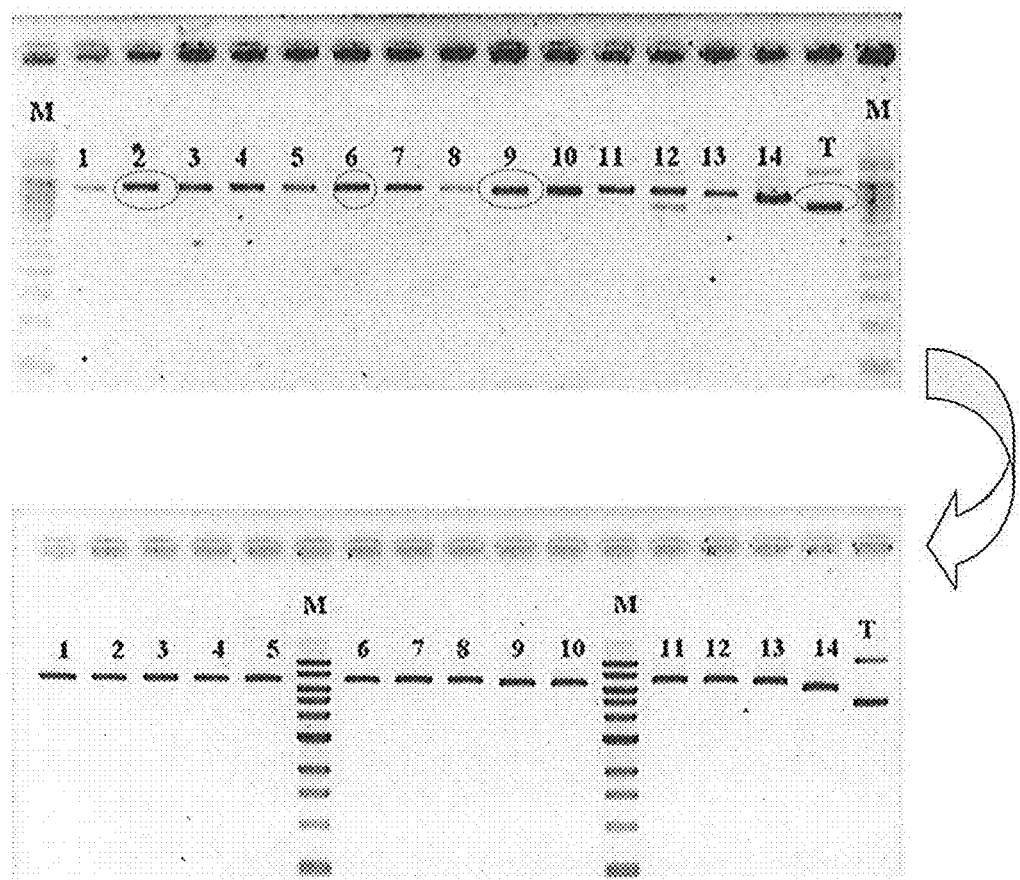

FIG. 5: Spectrometric assays of aliquots and adjustment of DNA concentrations after enzymatic digestion. The double arrow indicates that the concentrations have been readjusted.

Figure 6:
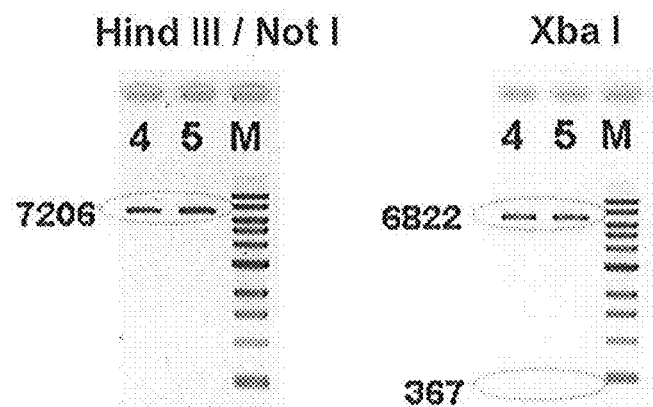
Figure 6:
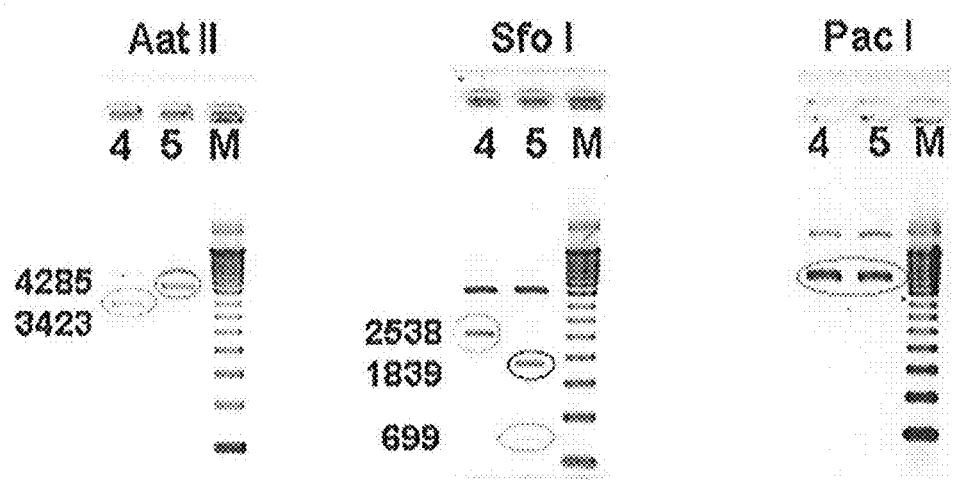

FIG. 6: Check of DNA identity after enzymatic digestion.—Differentiations of CD8-CD™ mutants. A: differentiation of pX2 AAC and pX2 CCA mutants. B: differentiation of X2 mutants between themselves.

Figure 7:
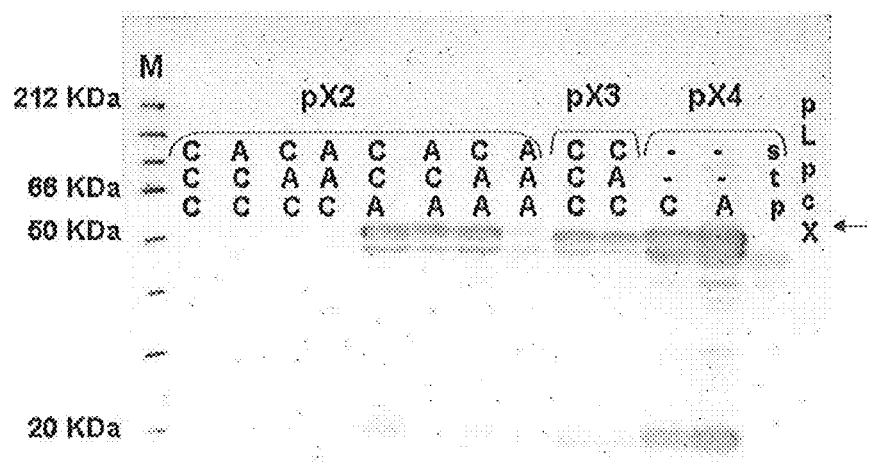

FIG. 7: Western Blot analysis of the expression of various CD8-CD™ chimeras. The CD8-CD™ chimera is indicated by an arrow.

Figure 8:
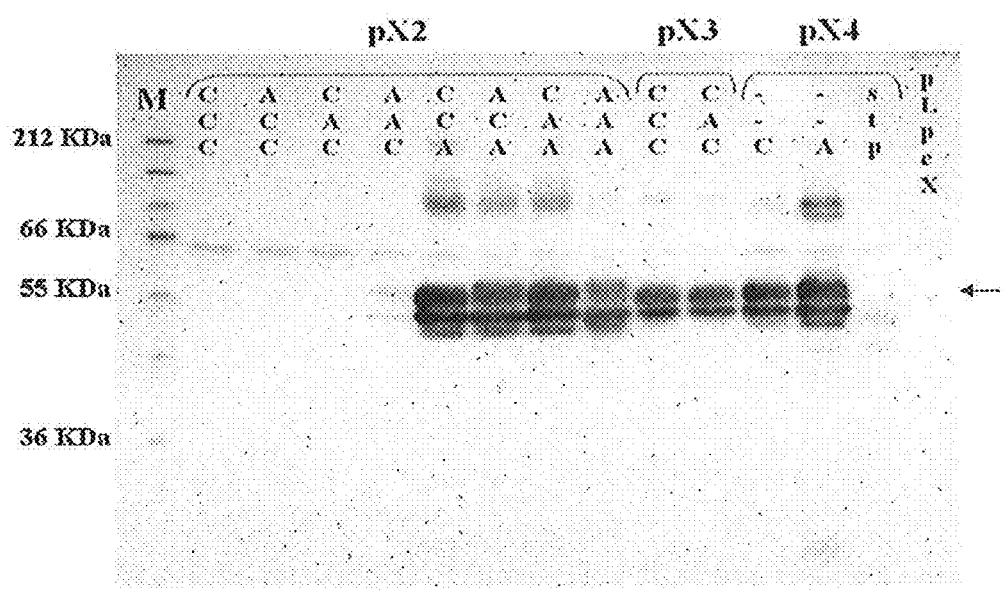

FIG. 8: Western Blot analysis of the expression of various CD8-CD™ chimeras after immunoprecipitation. The CD8-CD™ chimera is indicated by an arrow.

Figure 9:
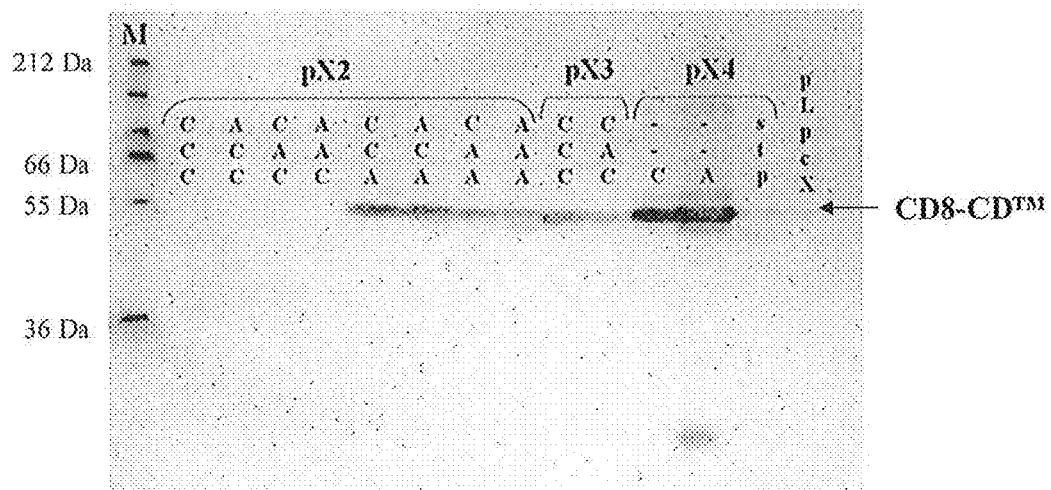

FIG. 9: Western Blot analysis of the expression of CD8-CD™ in exosomes isolated by ultracentrifuging. The signal at 55 kDa corresponds to the presence of CD8-CD™.

Figure 10:
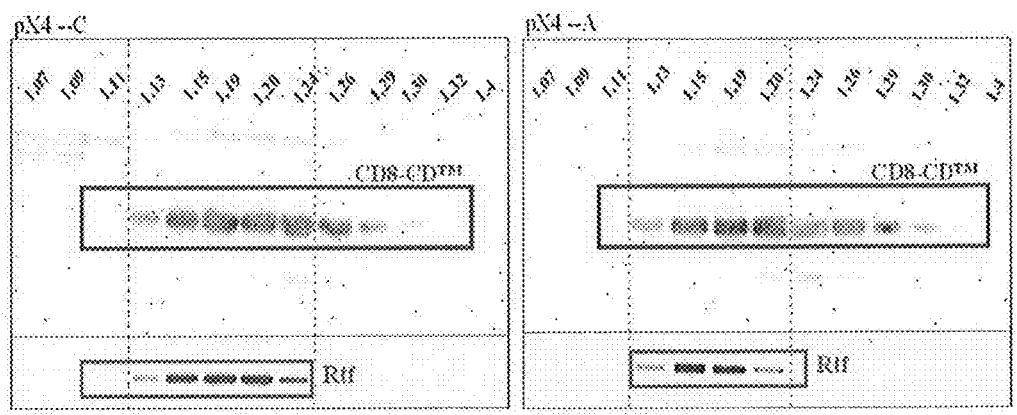

FIG. 10: Western Blot analysis of the CD8-CD™ content of vesicles isolated after sedimentation on a sucrose density gradient, for the pX4-C and pX4-A mutants.

Figure 11:
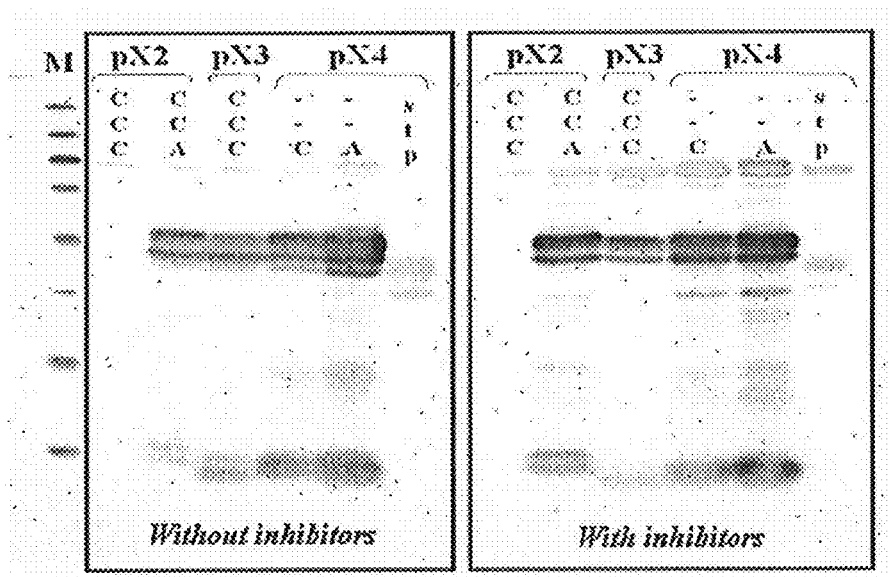

FIG. 11: Western Blot analysis of the expression of CD8-CD™ after cell lysis, in the presence or absence of vesicle transport inhibitors. The CD8-CD™ chimera is indicated by an arrow.

Figure 12:
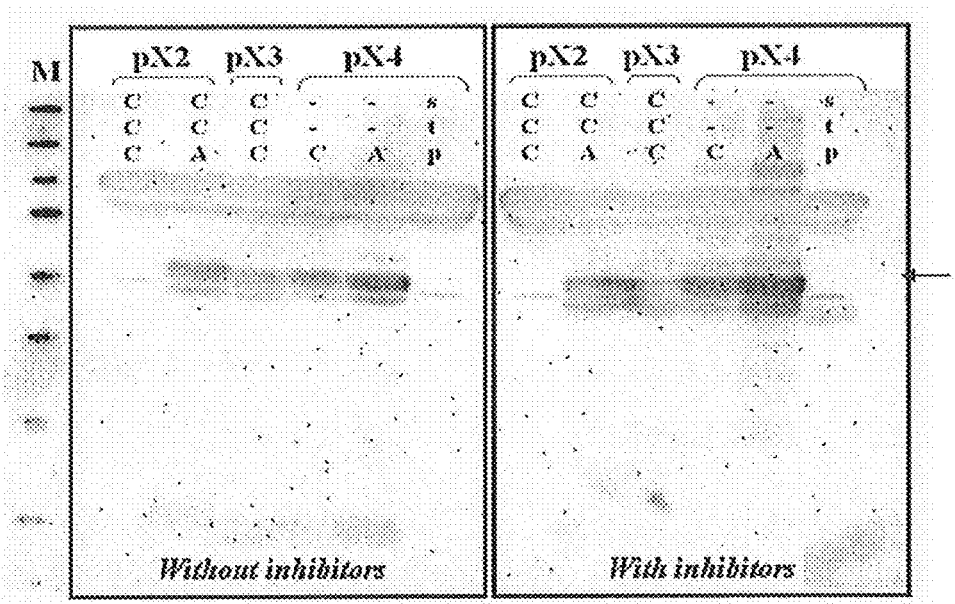

FIG. 12: Western Blot analysis of the expression of CD8-CD™ in exosomes, in the presence or absence of vesicle transport inhibitors. The CD8-CD™ chimera is indicated by an arrow.

Figure 13:
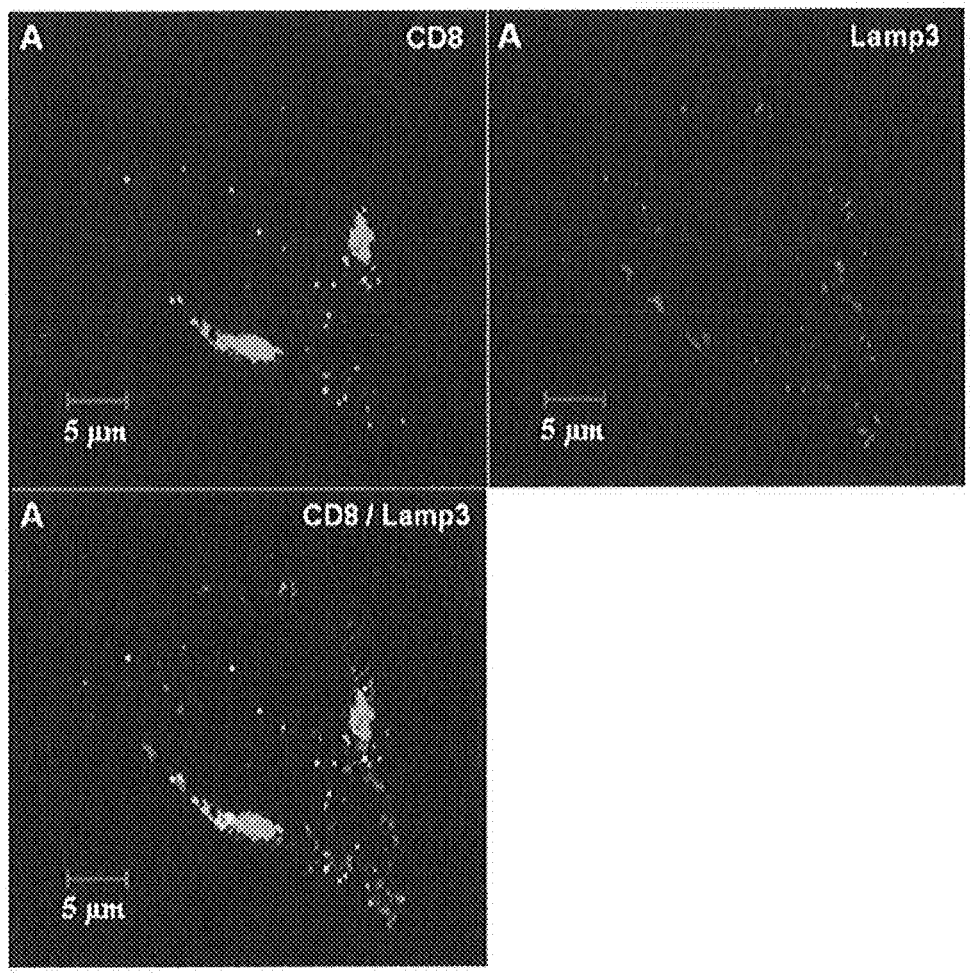

FIG. 13: Analysis by confocal immunofluorescence imagery of general phenotypes—Phenotype A—HEK293 cells transfected with pX2 CAC. This phenotype is found in pX2 mutants conserving Cys 3: pX2 CCC, pX2 ACC, pX2 CAC and pX2 AAC. (see Results section: "localisation by immunofluorescence).

Figure 14:
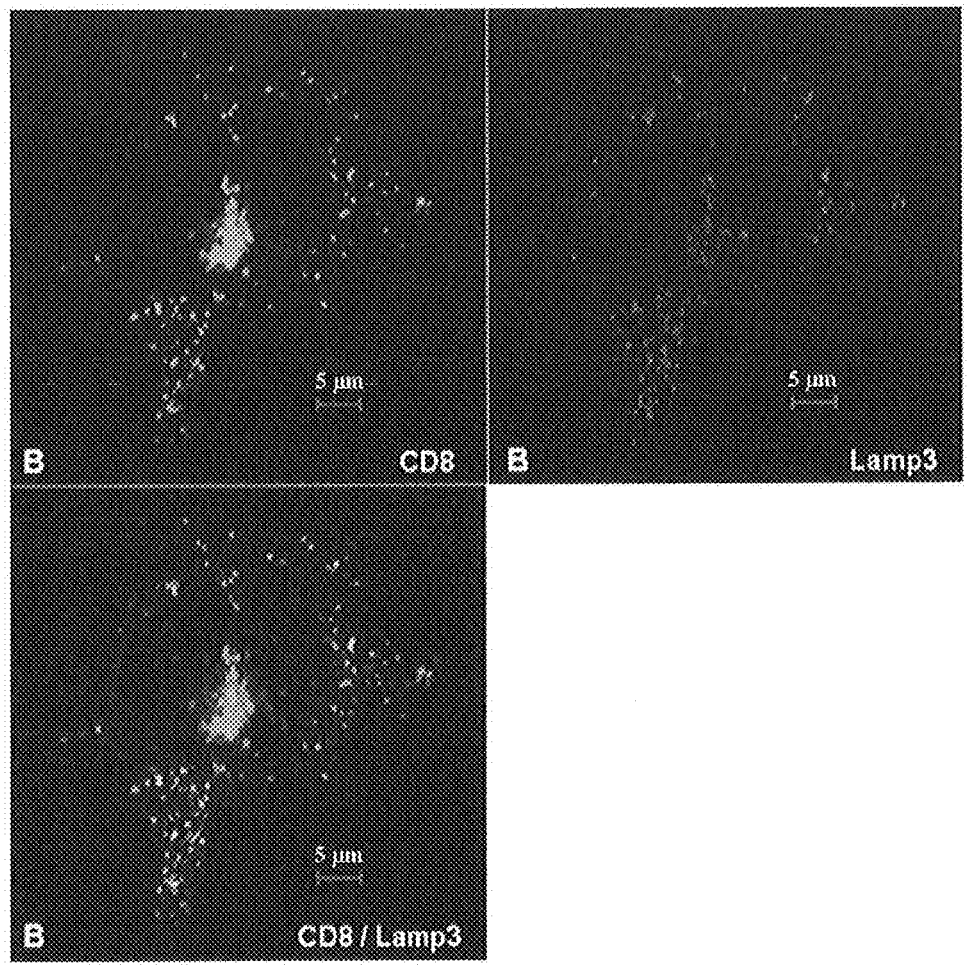

FIG. 14: Analysis by confocal immunofluorescence imagery of general phenotypes—Phenotype B—Cells transfected with pX2 CAA. This phenotype is found in pX2 mutants not conserving Cys 3: pX2 CCA, pX2 ACA, pX2 CAA and pX2 AAA. (see Results section: "localisation by immunofluorescence).

Figure 15:
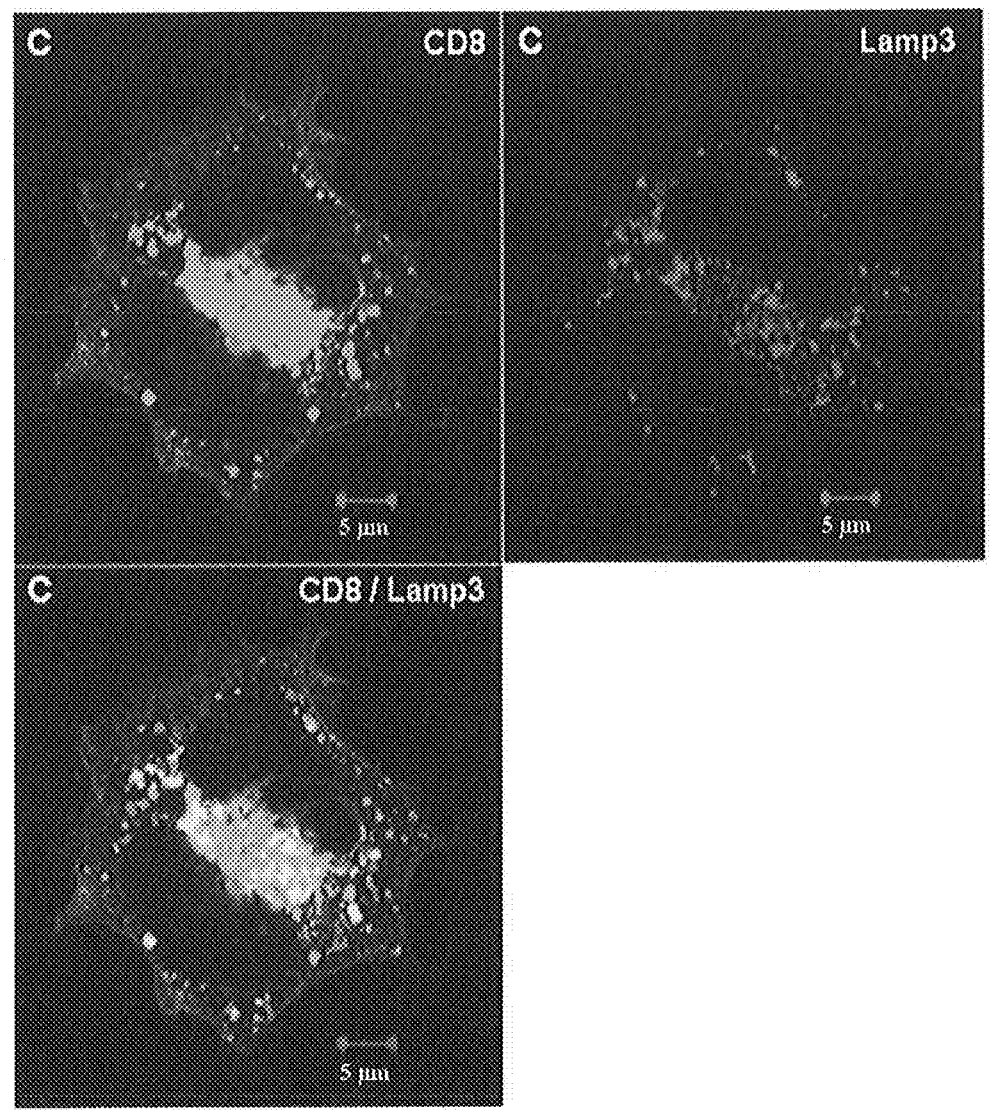

FIG. 15: Analysis by confocal immunofluorescence imagery of general phenotypes—Phenotype C—Cells transfected with pX3 CCC. This phenotype is found in the two pX3 mutants studied : pX3 CCC and pX3 ACC. (see Results section: "localisation by immunofluorescence).

Figure 16:
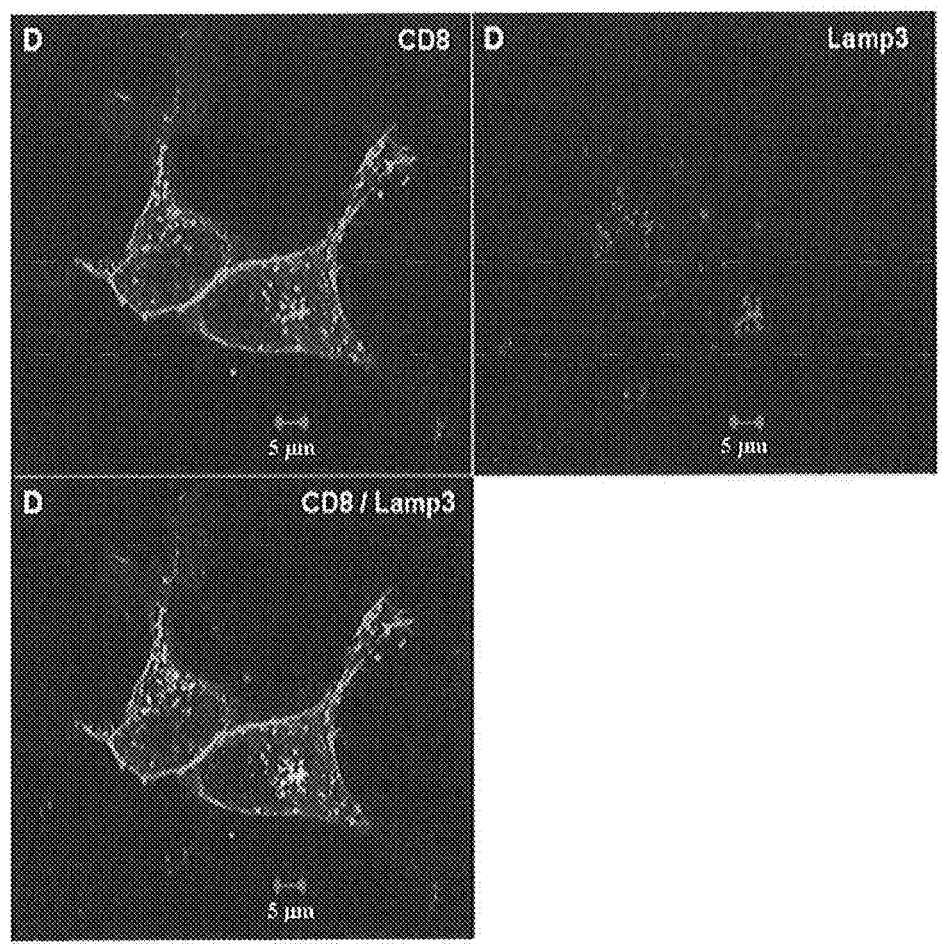

FIG. 16: Analysis by confocal immunofluorescence imagery of general phenotypes—Phenotype D—Cells transfected with pX4-C. This phenotype is found in the two pX4 mutants studied: pX4-C and pX4-A. (see Results section: "localisation by immunofluorescence).

Figure 17:
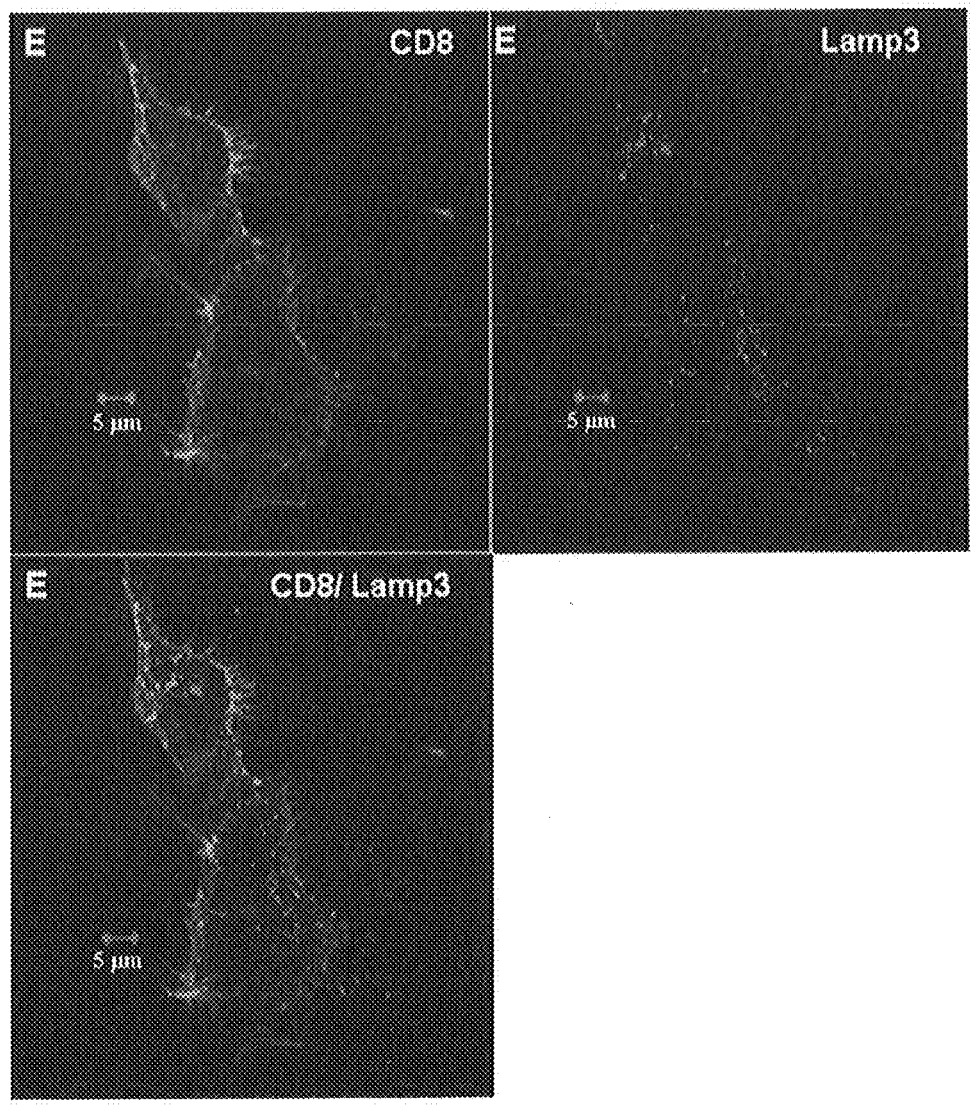

FIG. 17: Analysis by confocal immunofluorescence imagery of general phenotypes—Phenotype E—Cells transfected with pX4 stp. This phenotype is found only in pX4 stp. (see Results section: "localisation by immunofluorescence).

Figure 18:
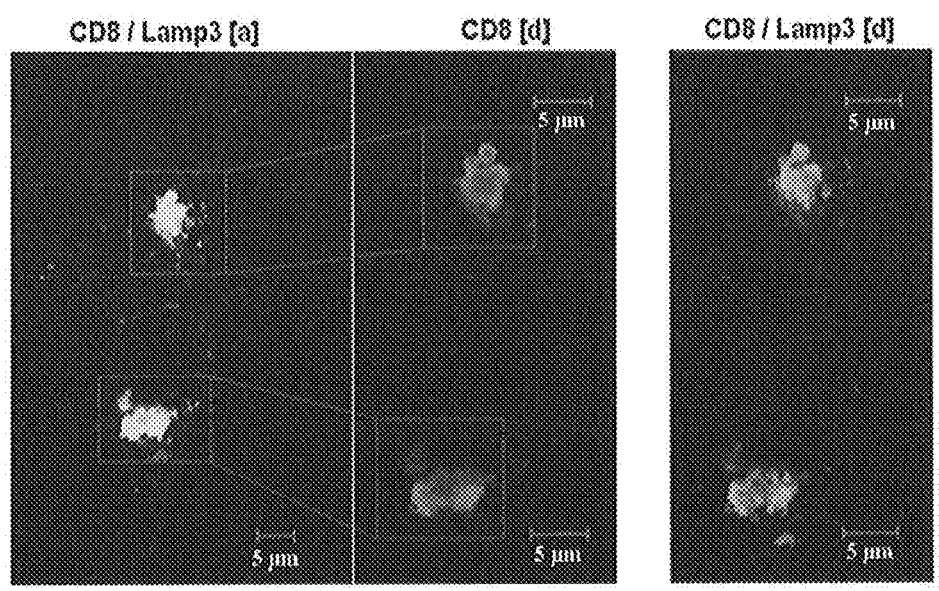

FIG. 18: Analysis by confocal immunofluorescence imagery of perinuclear zones giving a strong FITC signal. Cells transfected with pX3 CCC.

Figure 19:
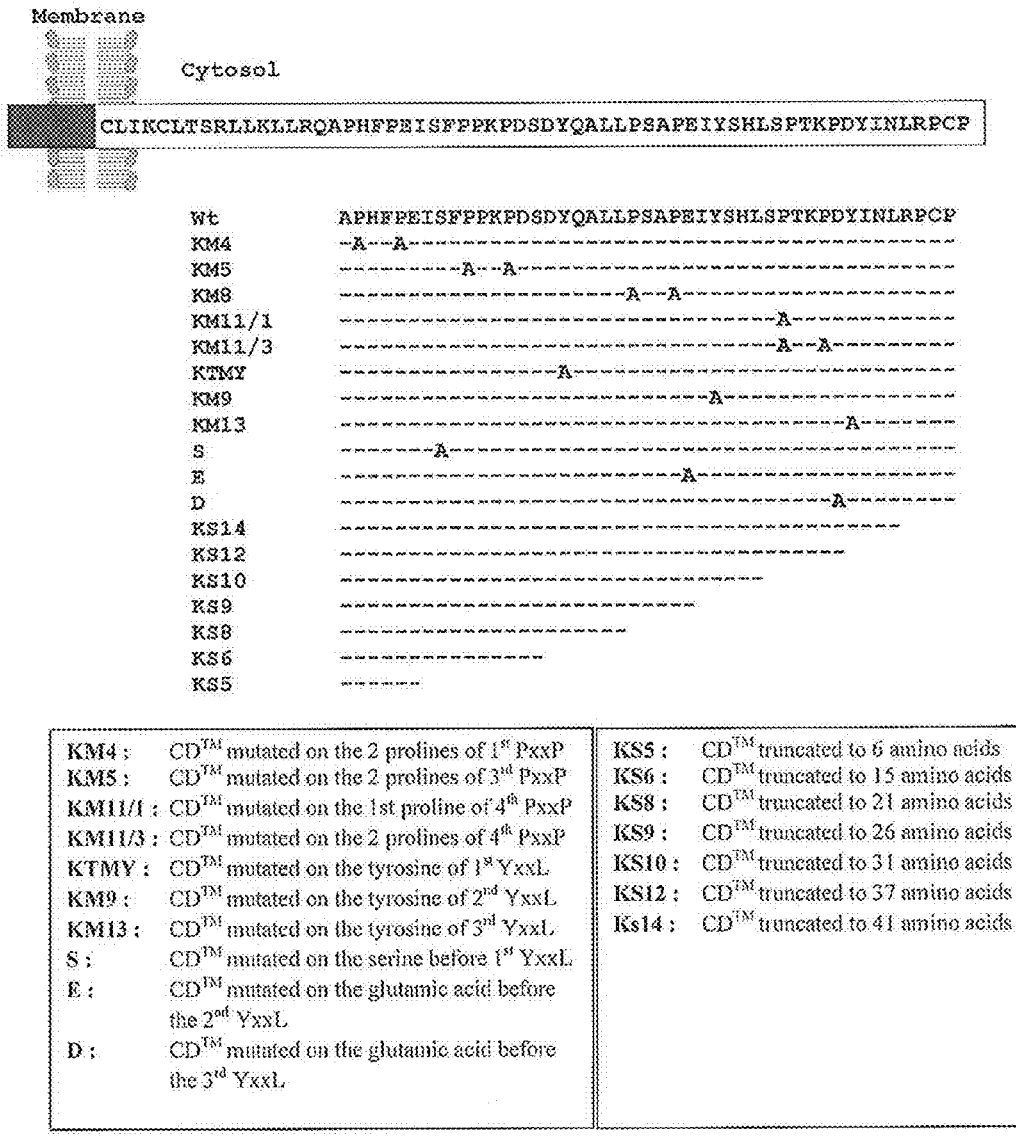

FIG. 19: Representation of mutant CD™ panel.

Figure 20:
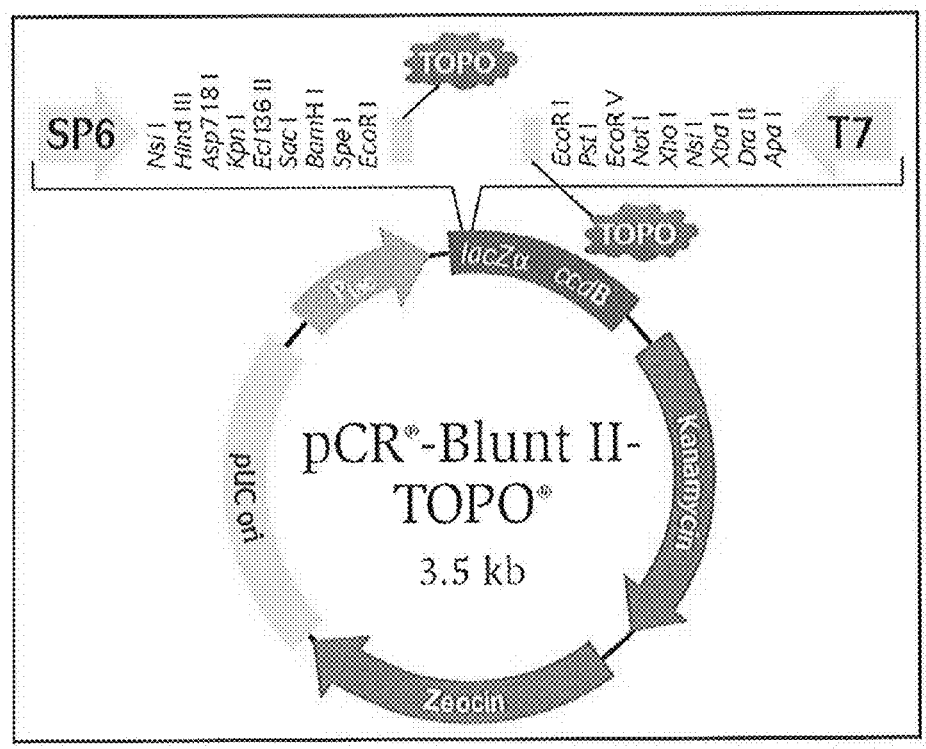

FIG. 20: Map of Topo® (pCR-Blunt II-TOPO) plasmid used to clone the various PCR products. The Topo vector supplied in the Topo-blunt cloning kit (Invitrogen) is linearized and has, at each of its 3'-phosphate ends, the topoisomerase I of the vaccinia virus, which enables ligation of the PCR products with the linearized Topo vector.

Figure 21:
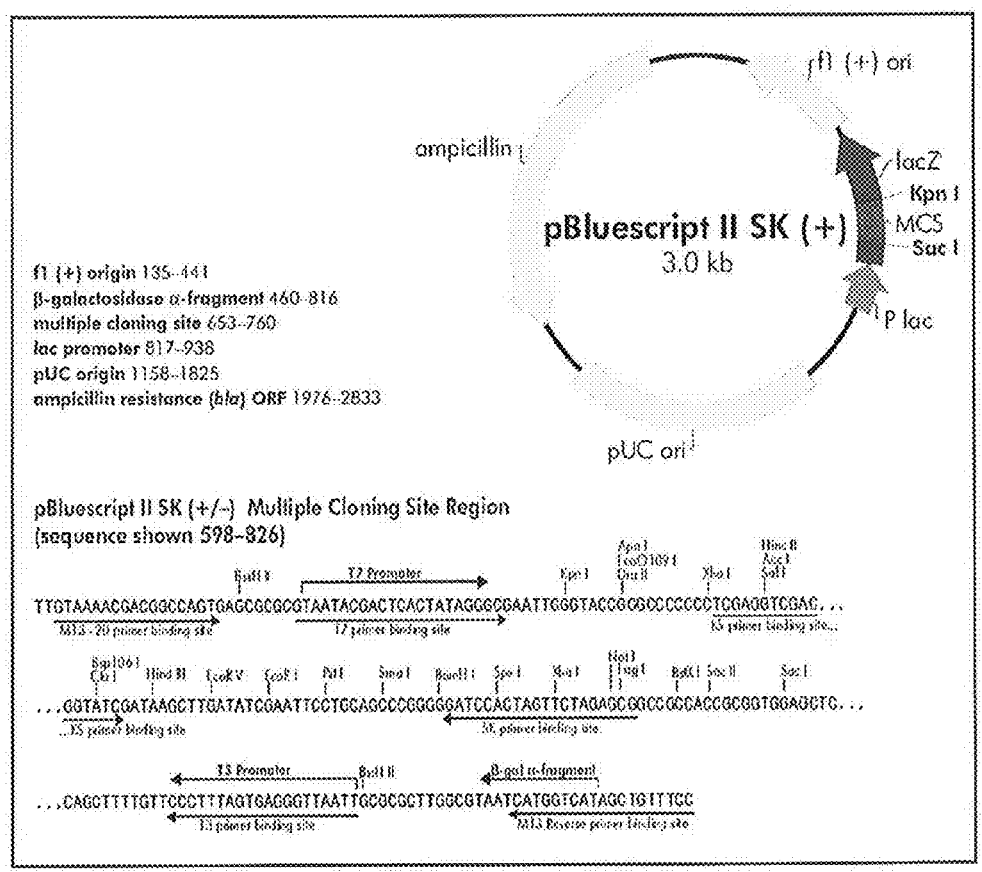

FIG. 21: pBluescript II KS (+) expression vector.

Figure 22:
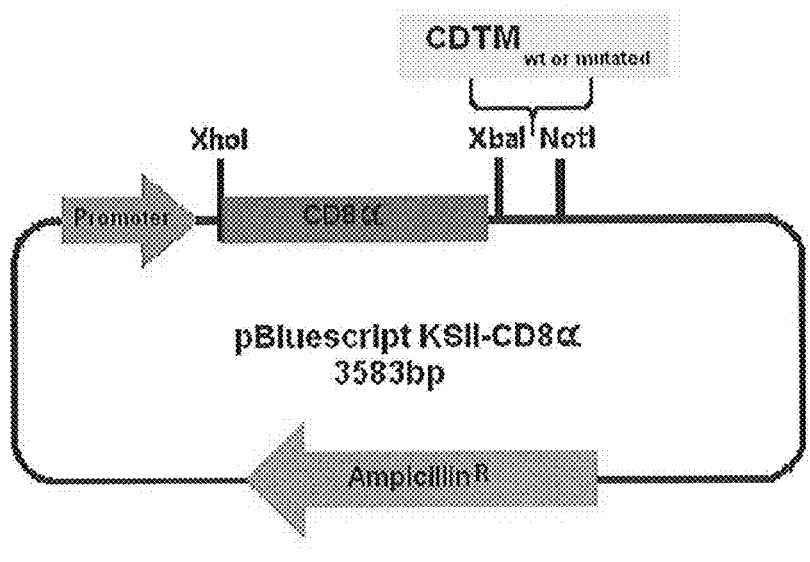

FIG. 22: Map of the pKSII-CD8α plasmid.

Figure 23:
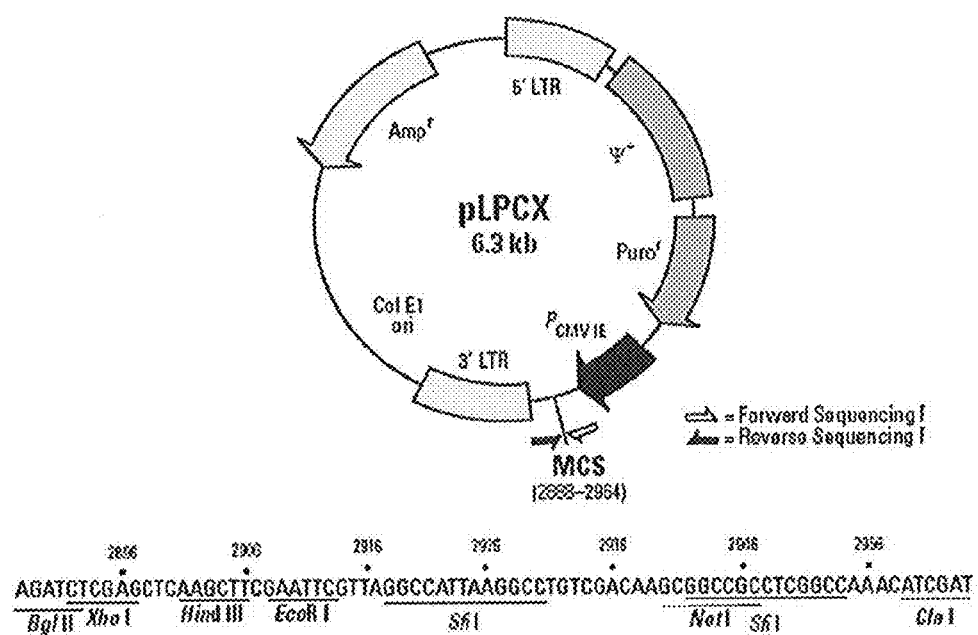

FIG. 23: Map of the retroviral plasmid pLPCX used for the expression of chimeric genes. These genes are introduced to the multiple cloning site.

Figure 24:
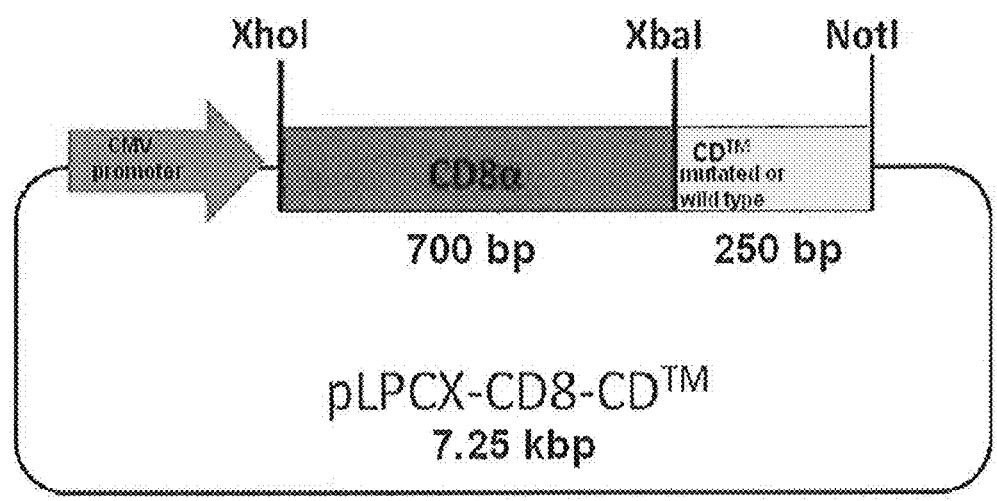

FIG. 24: Map of the final chimeric constructs cloned into the retroviral expression vector pLPCX.

Figure 25:
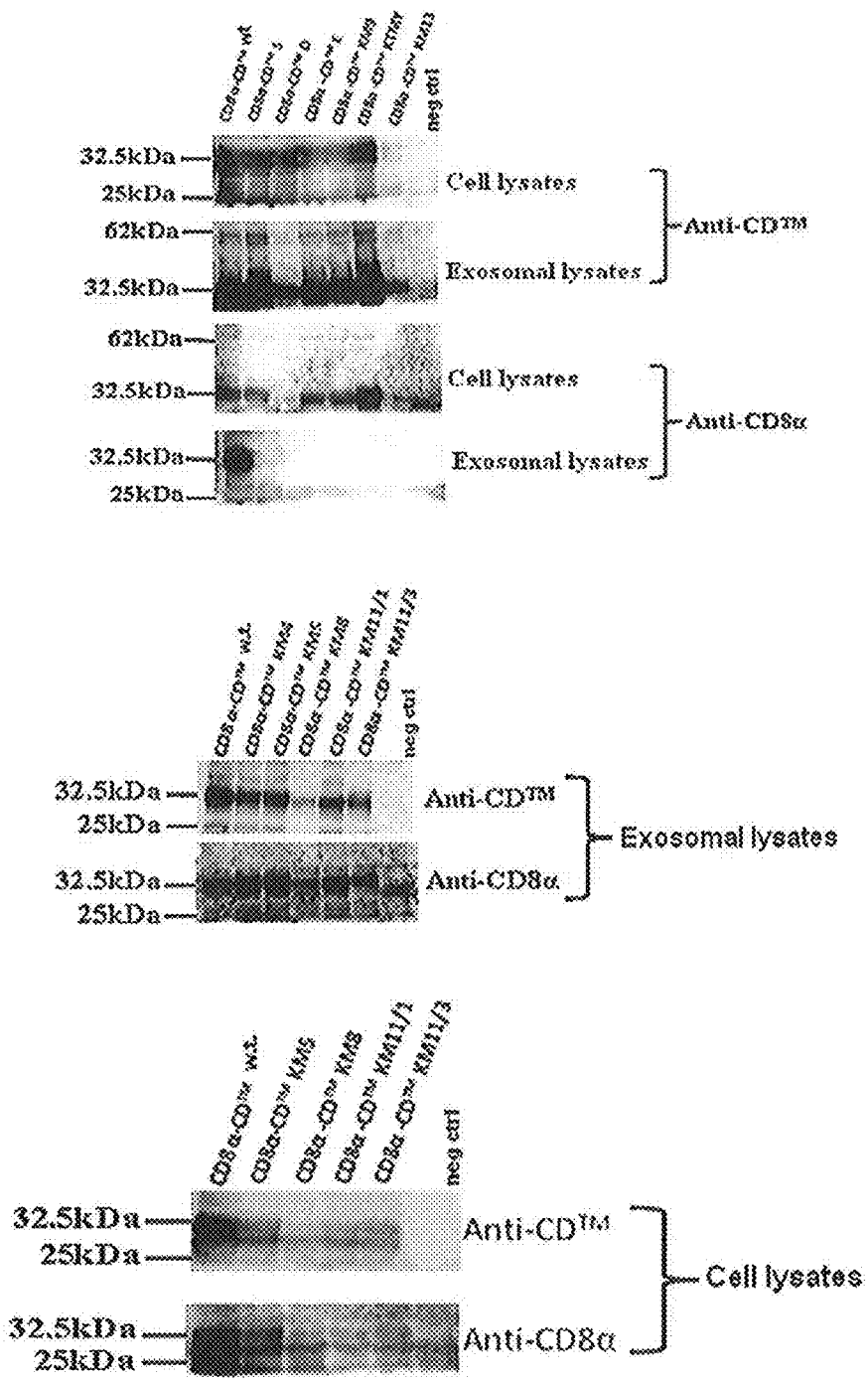

FIG. 25: Visualisation of the expression and exosomal targeting of chimeric proteins. Western Blot anti-CD™ and anti-CD8α for the cellular and exosomal lysates of all of the mutant and wild type CD8α-CD™ proteins (size from 31 kDa to 27 kDa) as well as of the negative control (pLPCX expression vector containing CD8α alone). The anti-CD™ and anti-CD8α rabbit serums were diluted to 1/200$^{th}$. anti-rabbit IgG secondary antibody coupled to peroxidase was diluted to 1/5000th.

Figure 26:
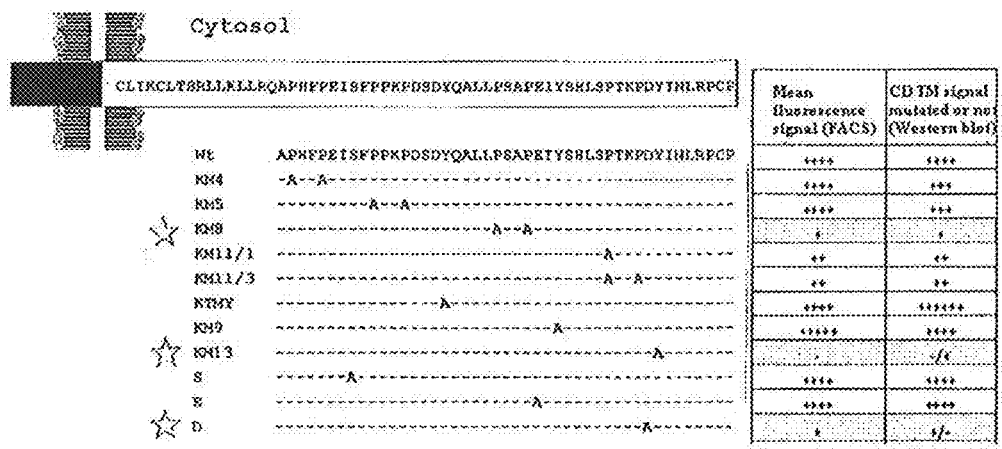

FIG. 26: Comparison of results of experiments for detecting CD8α associated with exosomes by flow cytofluorimetry and Western Blot. Table giving the results of the expression and the targeting to the exosomes of the various chimeric proteins analyzed. The mutants indicated by a star are significant for exosomal targeting. The presence of CD8α on the exosomes was shown by flow cytofluorimetry using a specific fluorescent mouse monoclonal antibody of a conformational epitope of the CD8α protein (53-6.7 antibodies from Pharmingen).

Figure 27:
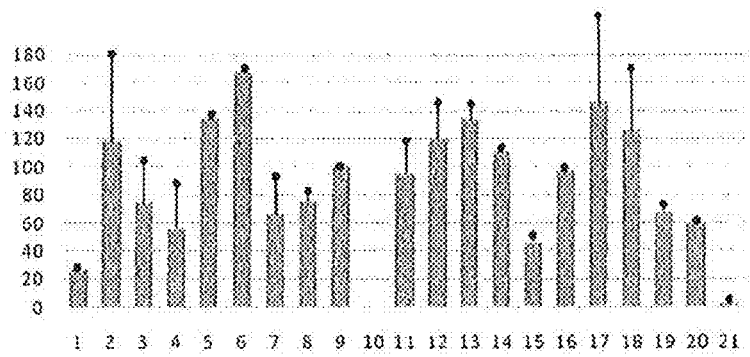

FIG. 27: Expression of CD8 at the surface of exosomes. Histogram representing the mean of exposure measurements of each chimeric protein at the surface of exosomes. These measurements were carried out by flow cytofluorimetry. The exposure of each chimeric protein is expressed as a percentage with respect to the exposure of the wild type CD8a-CD™ chimeric protein (construct no9 on the histogram=100%). The standard deviation is indicated. The chimeric proteins analyzed were: 1: negative control (pLPCX expression vector containing the CD8α alone); 2: KS5; 3: KS6; 4: KS8; 5: KS9; 6: KS10; 7: KS12; 8: KS14; 9: wild type sequence; 10: no construct; 11: KM4; 12: KM5; 13: S; 14: KTMY; 15: KM8; 16: E; 17: KM9; 18: KM11/1; 19: KM11/3; 20: D and 21: KM13. The results observed confirm the results presented in FIGS. 25 and 26.

Figure 28:
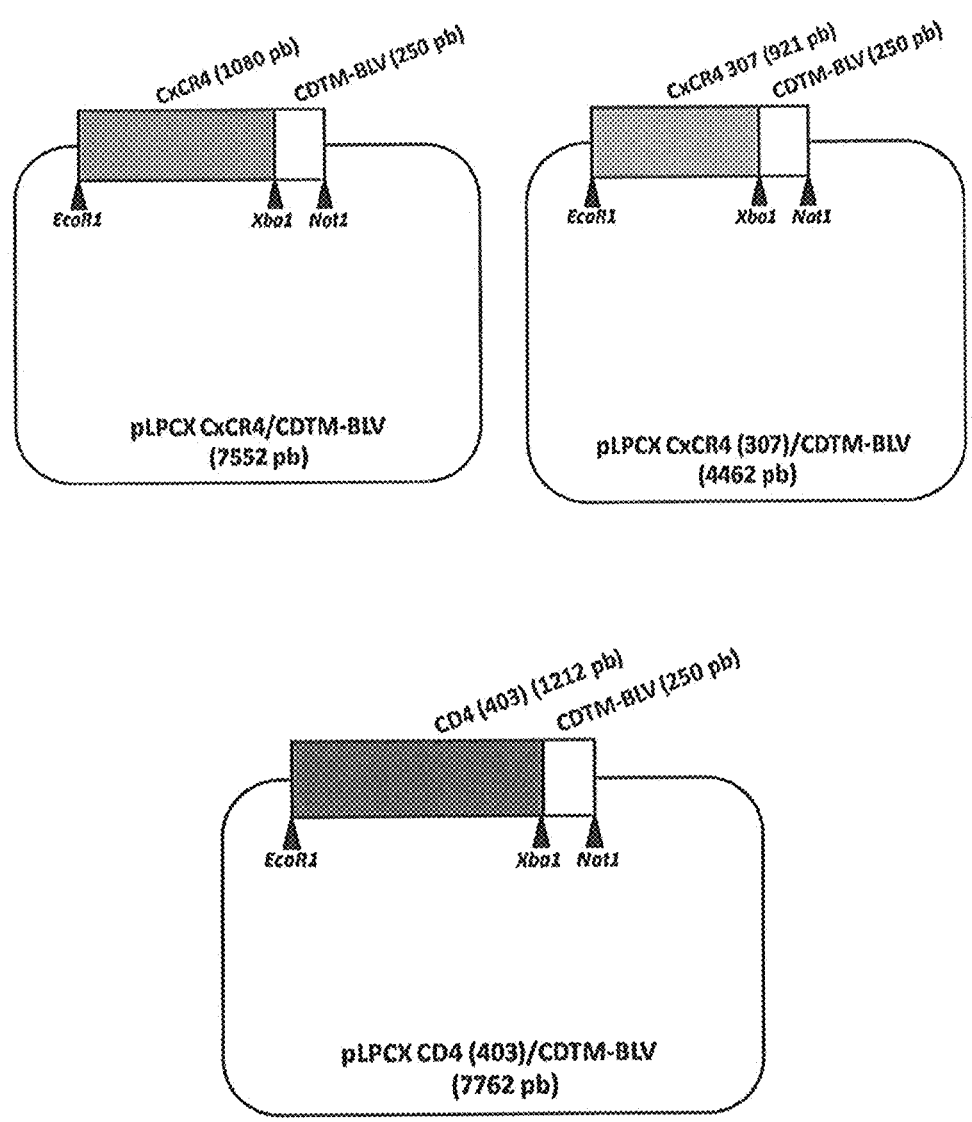

FIG. 28: Representation of various pLPCX expression plasmids obtained after cloning chimeric genes coding for proteins with single or multiple transmembrane domains.

Figure 29:
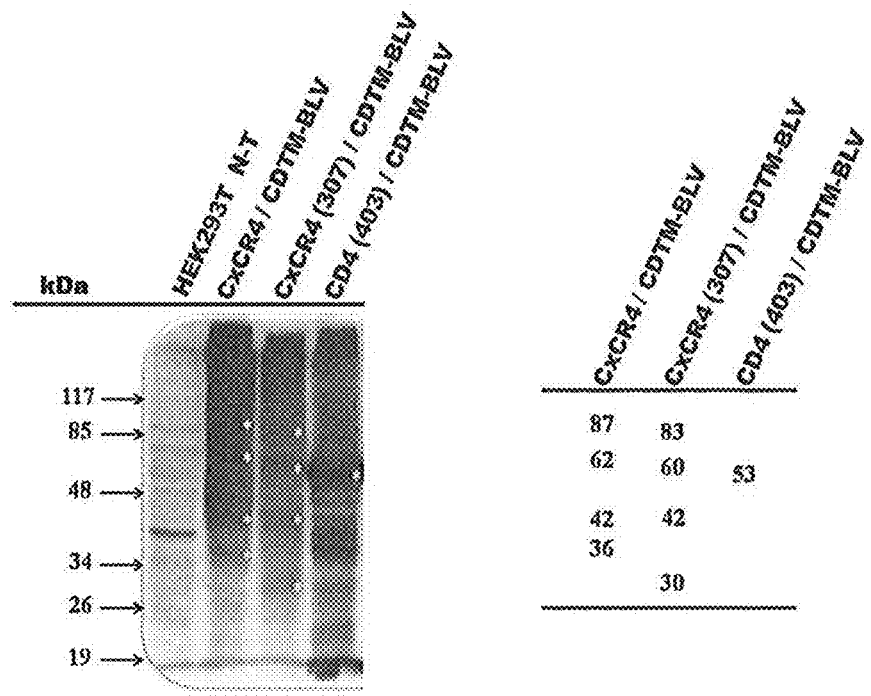

FIG. 29: A. Western Blot anti-CD™-BLV analysis carried out on the cellular protein extracts from non transfected (N-T) HEK293T cells or those transfected with the pLPCX expression vectors containing the three constructs coding for the three chimeric proteins. The anti-rabbit CD™-BLV primary antibody was used, diluted to 1/200. The anti-rabbit IgG secondary antibody coupled to peroxidase was used at 1/2000. B. The sizes of the observed bands corresponded to the expected sizes and are noted on the right.

Figure 30:
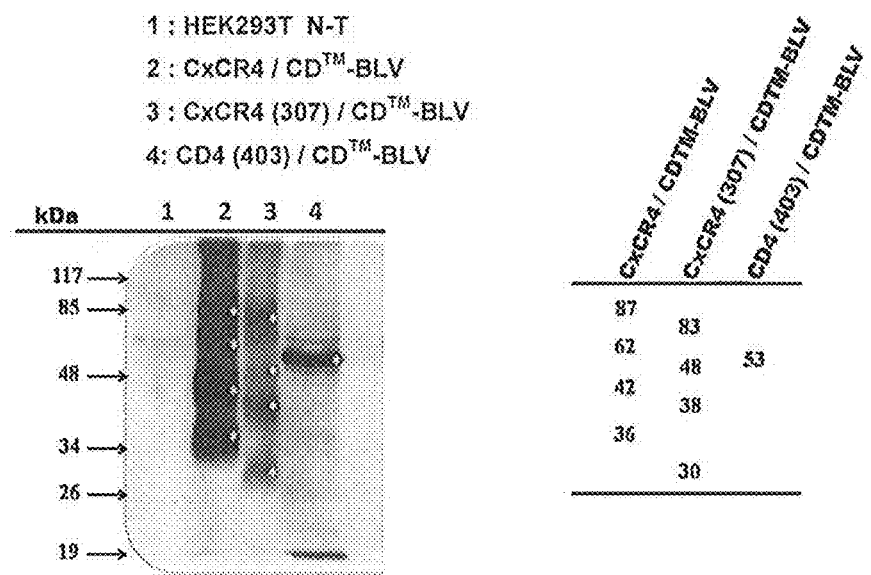

FIG. 30: A. Western Blot anti-CD™-BLV analysis carried out on the exosomal protein extracts produced by non transfected (N-T) HEK293T cells or those transfected with the pLPCX expression vectors containing the three constructs coding for the three chimeric proteins. The anti-rabbit CD™-BLV primary antibody was used, diluted to 1/200. The anti-rabbit IgG secondary antibody coupled to peroxidase was used at 1/2000. B. The sizes of the observed bands corresponded to the expected sizes and are noted on the right.

Figure 31:
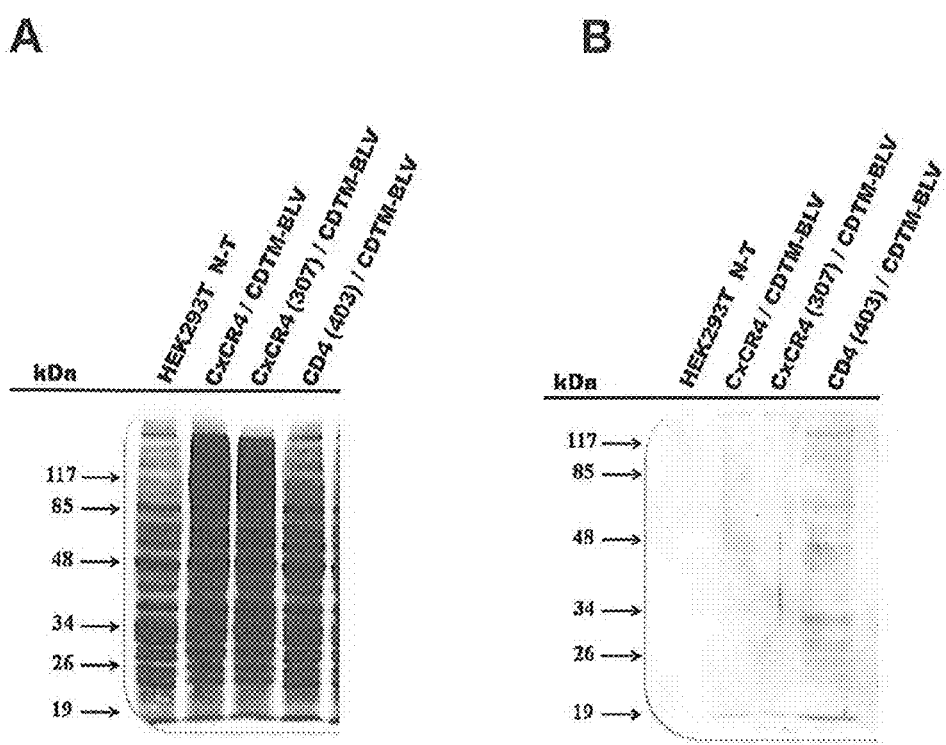

FIG. 31: Coomassie Blue staining of protein fingerprints of the various cellular (A) and exosomal (B) extracts.

EXAMPLES

Example 1

Method and Apparatus
I. Preparations of plasmidic DNA:
  A. Transformation of Bacteria:
  Competent DH5α bacteria (200 µl) were transformed by thermal shock with 12.5 ng of each of the 13 DNAs studied coding for the wild type or mutant CD™ of the BLV virus, as well as by a plasmid devoid of the insert (pLPCX) acting as a negative control.
  The bacteria were then spread onto a LB/Agar medium containing 50 µg/mL of ampicillin, at 37° C. for 16 h. They were then stored at 4° C.
  B. Pre-culture and Culture of Bacteria:
  A colony of each type of bacteria was then pre-cultured in 3 mL of LB medium containing 100 µg/mL of ampicillin, at 37° C. with stirring, for approximately 8 h.
  Each pre culture served to inoculate, at 1/200, two flasks each containing 250 mL of LB/Amp (100 µg/mL). Incubation was carried out at 37° C., with stirring, for 12 to 16 h.
  C. STET Maxipreparation:
  The cultures obtained were centrifuged (GR 412, Jouan) for 20 min at a speed of 3600 rpm and at a temperature of 4° C. The residues were taken up in 25 mL of STET buffer (Sucrose 8%, Triton X100 5%, Tris HCl pH 8, 50 mM, EDTA 50 mM) to which 500 µl of lysozyme (10 mg/mL; Sigma) and 250 µl of RNase (2 mg/mL; Sigma) were added. The tubes were then incubated for 10 min at 100° C. and centrifuged at 16000 rpm for 30 min. The supernatants obtained were incubated for 45 min at 65° C. in the presence of 1 mg/mL of proteinase K (Amresco). The supernatants were removed and the DNA was precipitated with 0.15 volume of sodium acetate (AcNa) 3 M, pH 6 and 0.6 volume of isopropanol. The solutions were centrifuged (Aventi 30, Beckman) at 4° C. for 15 min at 15000 rpm. The residues obtained were washed with 10 mL of ethanol before being centrifuged again using the same parameters. The nucleic acids obtained were dried and taken up in 2 mL of TE 1× then stored at 4° C.

The presence of super-coiled DNA was verified for each Maxipreparation product by electrophoresis of 0.2 µl and 1 µl of the products by 0.8% agarose gel electrophoresis.

D. Column Purification:

STET Maxipreparations can be used to produce large quantities of plasmids, but the degree of purity could be improved. To this end, we purified each of the 14 plasmids by means of two passes over AX100 columns (Kit Nucleobond PC 100, Macherey Nagel). After precipitation with isopropanol, the purified plasmids obtained were taken up in 500 µl of TE1× and stored at 4° C.

The presence of super-coiled DNA was then verified by agarose gel electrophoresis (0.8%) for each eluate obtained as well as for the fraction not retained on the columns (FT=flow-through).

The DNA concentration of the solutions obtained was evaluated by spectrophotometry, at a wavelength of 260 nm.

E. Taking Aliquots and Precipitation with EtOH:

Each DNA type was placed into tubes in aliquots of 50 or 100 µg, then precipitation was carried out with ethanol (EtOH) and NaCl, in a laminar flow hood, in order to sterilize the plasmids. The residues obtained were taken up in an amount of 200 µl of TE1× per 100 µg of plasmids, i.e. a concentration of 500 ng/µl. The presence of DNA in the aliquots was verified by 0.8% agarose gel electrophoresis.

F. Spectrophotometric Assay of Aliquots Obtained:

The aliquots were assayed by spectrophotometry at a wavelength of 260 nm. The samples were diluted to 1/50 and were assayed in a final volume of 500 µl.

G. Enzymatic Digestions:

The identity of each plasmid was checked by digestion of 20 ng of each of them with restriction enzymes (New England Biolabs): the Hind III/Not I pair, Xba I, Aat II, Pac I, Sfo I. The plasmids were differentiated by the number of bands obtained and their molecular weight, after agarose gel electrophoresis (0.8%) of each digestion product.

II. Analysis of the Expression of Chimeras

A. Cell Culture:

HEK293 cells (Human Embryonic Kidney cells) were cultivated in DMEM (Dulbecco's modified Eagle's medium), supplemented with 10% foetal calf serum (FCS) and 20 µg/mL of gentamicin, at 37° C. under 5% $CO_2$.

B. Transfection:

For the transfections, $5 \times 10^5$ cells were plated onto 2 mL of medium per 9.6 $cm^2$ well (6 well plates). After incubating overnight at 37° C. under 5% $CO_2$, the medium was replaced with complete DMEM without antibiotics.

The cells were then transfected by a polyplex formed by complexing, in a NaCl buffer (0.15 M), 6 µl of Jet PEI (Qbiogen) and 3 µg of each test nucleic acid; a plasmid expressing LacZ acted as the positive control for transfection. After 24 h of incubation at 37° C. under 5% $CO_2$, the medium was eliminated and replaced with complete DMEM with 20 µg/mL de gentamicin. Optimum plasmid expression was obtained 48 h after commencing the transfection.

In certain cases, in order to analyze the importance of vesicular transport in the degradation and targeting of CD™, we used vesicular transport inhibitors, namely bafilomycin and Ly 294002. 32 h post-transfection, each inhibitor was added to the culture medium in a concentration of 0.5 µM for bafilomycin and 10 µM for Ly 294002.

C. Protein Extraction:

48 h post-transfection, the cells were lysed by a 0.5% THE-NP40 buffer to which 0.1 mM of PMSF had been added. After clarification by centrifuging (14000 rpm, 15 min, 4° C.; Eppendorf 5417R), the lysates were assayed by spectrophotometry (at 595 nm) using the Bradford technique.

For each sample, 200 µg de proteins was removed which was supplemented with lysis buffer for a final volume of 30 µl to which 10 µl of 4× buffer sample was added (CB 4×: NaOH 200 mM, EDTA 20 mM, SDS 2%, bromocresol green 0.05%, glycerol 10%).

D. Preparation of Exosomes:

Before lysing the cells, the culture media were recovered and pre-centrifuged at 10000 rpm for 20 min at a temperature of 4° C. (Aventi 30, Beckman). The supernatants obtained were then ultracentrifuged (Optima LE-80K, Ti 50 rotor, Beckman) at 100000 g for 2 h at a temperature of 4° C. The residues obtained are taken up in 100 µl of CB 1×.

We also analyzed the exosomes by sedimentation on a sucrose density gradient. The residues obtained after ultracentrifuging the culture media were taken up in 100 µl of a 0.25 M sucrose solution.

The vesicles were then deposited on a sucrose gradient prepared with 8 layers (of 1.2 mL) of different densities (molarity): 0.5/0.75/1/1.25/1.5/1.75/2/2.5. The tubes were then centrifuged (Optima LE-80K, SW 41 rotor, Beckman) at 39 000 rpm for 16 h, at a temperature of 4° C.

After centrifuging, the gradient was recovered in 700 µl fractions. The proteins were precipitated by adding the same volume of 30% TCA. The tubes were stored for 2 h at 4° C. then centrifuged (Eppendorf, 5417R) at a temperature of 4° C. for 20 min at 13000 rpm. The residues were taken up in 500 µl of acetone then centrifuged again, as before.

The residues thus obtained were taken up in 80 µl of CB1× then analyzed by acrylamide-SDS gel migration and Western Blot.

E. Western Blot and Immunoprecipitation:

The protein samples obtained were analyzed by Western Blot: after migration and separation on acrylamide gel (12.5%), the proteins were transferred onto a hydrophobic PVDF membrane (Immobillon-P, Millipore).

The presence of mutants of the TM protein was revealed by immunolabelling using the following antibodies:
  primary antibody: BLV anti-rabbit CD™ antiserum (dilution 1/200).
  secondary antibody: Anti-rabbit IgG labelled with peroxidase (dilution 1/5000; Jackson Immuno Research, JIR)

The presence of transferrin receptors was revealed by immunolabelling using the following antibodies:
  primary antibody: anti-human TFr mouse IgG (dilution 1/200; Zymed)
  secondary antibody: anti-mouse IgG (dilution 1/5000; JIR)

In order to selectively increase the concentration of the protein being studied, we also carried out immunoprecipitations on the protein lysates, prior to gel migration. After normalizing the protein quantities, lysate adsorption was carried out on sepharose 6B, in order to eliminate non-specific reactions and the immunoprecipitation was carried out with protein sepharose 6A in the presence of 2.5 µg of the following antibodies:
primary antibody:
anti-mouse CD8 mouse IgG (19/178) (JIR)
anti-mouse CD8 mouse rat IgG (53/672) (JIR)
secondary antibody:
Anti-mouse IgG (JIR)
Anti-rat IgG (JIR)

The residues obtained were then taken up in 70 µl de CB 1.5×.

III. Localisation by Immunofluorescence

A. Preparation of Slides.

Coverslip type slides were sterilized in absolute EtOH, in a laminar flow hood, then placed in 1.9 cm$^2$ wells (24 well plates) before being coated with poly-L-Lysine (25 µg/mL, Sigma) for 1 h at 37° C. After washing with PBS, the slides were stored at 4° C., in 1 mL of PBS.

B. Cell Culture and Transfection.

The HEK293 cells were cultivated and transfected according to the method described in the section "Analysis of chimeric expression". 24 h post-transfection, the cells were taken up in 35 mL of complete DMEM, then distributed into 1.9 cm$^2$ wells (24 well plates) containing the slides which had been sterilized and coated in an amount of 1 mL of cellular dilution per well. The cells, thus undergoing culture, were incubated for 24 h at 37° C., under 5% $CO_2$.

C. Fixing and Permeabilization.

The cells were then fixed for 30 min with a solution of formaldehyde (4%) then permeabilized with Triton X-100 (0.2% final). After three 10 min rinses with PBS, the slides were stored with 1 mL de PBS, at 4° C.

D. Labels for Immunofluorescence.

The various antibodies at our disposal meant that we could test several labels for localisation by immunofluorescence:

CD8 Labels:
No 1: mouse IgG/anti-mouse CD8 (19/178) (JIR)+anti-mouse IgG FITC (JIR)
No 2: mouse Ascites/anti-mouse CD8 (19/178) (JIR)+anti-mouse IgG FITC (JIR)
No 3: rat IgG/anti-mouse CD8 (53/672) (JIR)+anti-rat IgG FITC (JIR)
No 4: rat IgG (53/6.7)/anti-mouse CD8 FITC (Pharmingen)

Labelling of Intra-Cell Compartments:
No 5: mouse IgG/anti-human CD63 (Lamp3) (Zymed)+anti-mouse IgG Cy3 (Sigma)
No 6: mouse IgG/anti-human Lamp1+anti-mouse IgG Cy3 (Sigma)
No 7: mouse IgG/anti-human Tf2 (Zymed)+anti-mouse IgG Cy3 (Sigma)
No 8: rabbit IgG/anti-caveolin (BD)+anti-rabbit IgG TRITC (JIR)

Results

Knowledge of the exosome formation process is incomplete. Similarly, the functions associated with the cytoplasmic domain of Env are poorly characterized. The present study is based on the hypothesis that the BLV model is a good tool for studying the phenomena of exosome formation and viral particle formation and that the cytoplasmic domain of the TM protein (CD™) of BLV is a potentially important tool for the development of vaccination by "exosome display".

In order to evaluate this potential and in order to characterize the functions responsible for targeting the TM protein of BLV, and more particularly the role of palmitoylated or non palmitoylated cysteine residues, we developed several vectors allowing expression, in eukaryotic cells, of chimeric transmembrane vectors comprising the ectodomain of the mouse CD8 protein and the CD™ domain (CD8-CD™ chimeric proteins). Wild type CD8-CD™ chimeras as well as mutated CD8-CD™ chimeras have been expressed.

In a human cell, the mouse CD8 ectodomain is a neutral element that does not interfere with cell receptors. The chimeras used thus guarantee the absence of interactions between the ectodomain of the proteins and the cell structures.

As a consequence, these chimeras mean that the cytoplasmic and transmembrane domains of the TM protein can be specifically studied, avoiding phenomena caused by the ectodomain of the TM protein and by the SU protein associated therewith.

Figure 1:
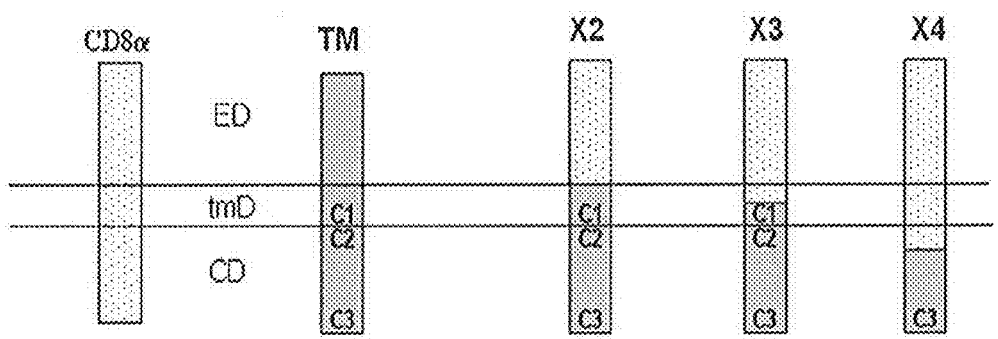
FIG. 1: Representation of the various types of CD8-CD™ constructs studied. Construct X2 (sequences SEQ ID NO: 79 and SEQ ID NO: 80): the ectodomain (ED) of CD8 was fused with the transmembrane (tmD) and cytoplasmic (CD) domains of the TM protein of BLV. This construct conserved the two palmitoylation sites Cys 1 and Cys 2 as well as the non-palmitoylable cysteine residue regulator (Cys 3) of the TM protein of BLV. Construct X3 (sequences SEQ ID NO: 81 and SEQ ID NO: 82): ED and a portion of the tmD of CD8 were fused with a portion of the tmD of BLV and the totality of the CD™ of BLV. The TmD of BLV was thus freed of its first 15 residues. This construct conserved the two palmitoylation sites (the cysteine residues in positions 153 and 158) as well as the non-palmitoylable cysteine residue regulator (the cysteine residue in the C-terminal position; Cys 3) of the TM protein of BLV. Construct X4 (sequences SEQ ID NO: 83 to SEQ ID NO: 86): The major portion of CD™ BLV was conserved. In this construct, the transmembrane domain of mouse CD8 alpha was linked via a linker with the "RSR" sequence to the CD domain of the TM protein of BLV. This construct comprised only the non-palmitoylable cysteine residue regulator (Cys 3) of the TM protein of BLV.
Figure 2:
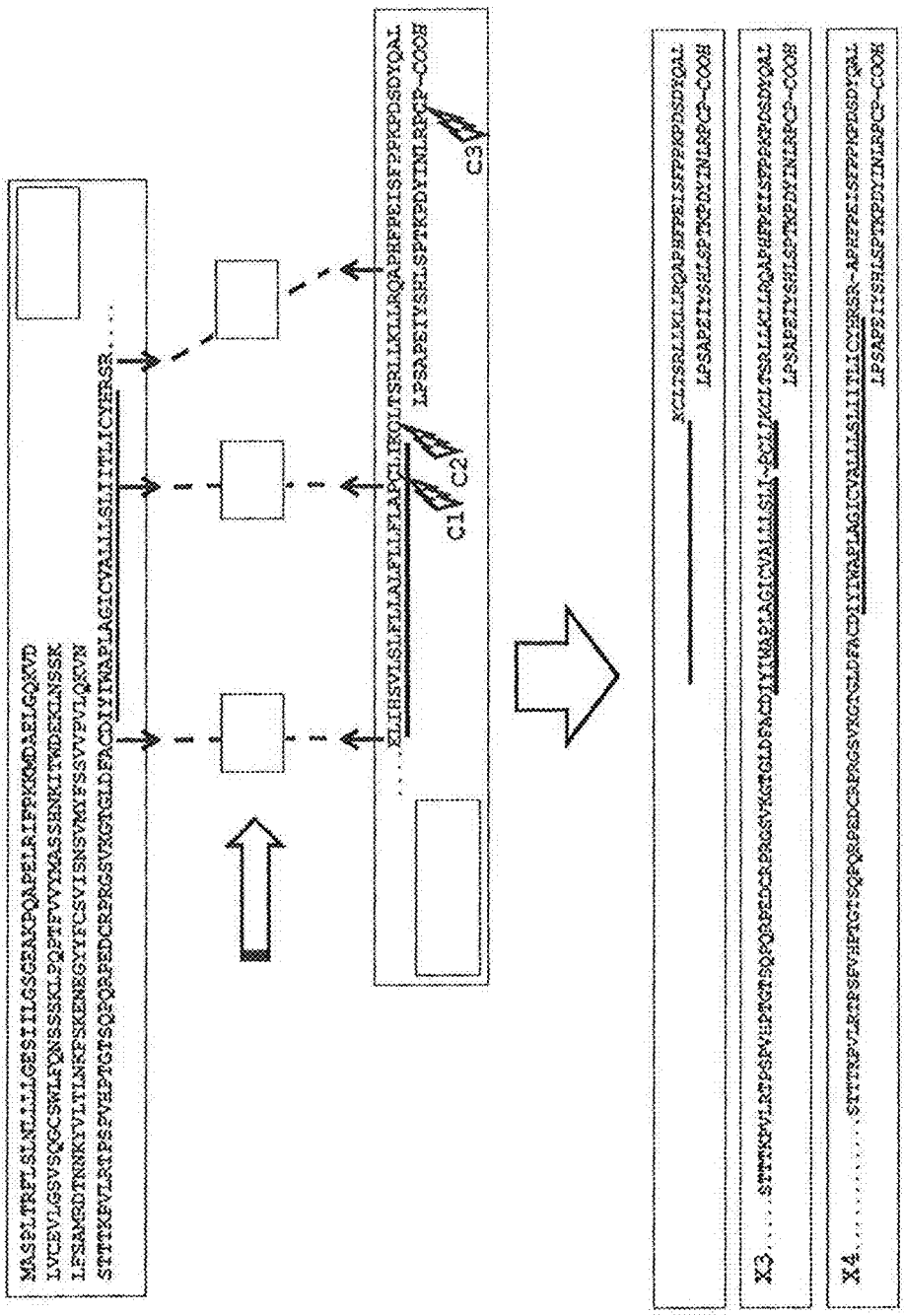
FIG. 2: Summary of the sequences of chimeric proteins obtained from the mouse CD8 alpha protein and from the TM protein of BLV. The underlined residues correspond to residues of the transmembranes helixes of the CD8 alpha and TM proteins. The three cysteine residues of the TM protein of BLV which had been mutated (substitution by an alanine residue) are indicated by C1, C2 and C3. The chimeric proteins created correspond to constructs X2 (sequence SEQ ID NO: 79 and SEQ ID NO: 80), X3 (sequence SEQ ID NO: 81 and SEQ ID NO: 82) and X4 (sequence SEQ ID NO: 83 to SEQ ID NO: 86).

Three types of constructs were used (see FIGS. 1 and 2). Starting from these constructs, we developed different pLPCX expression vectors allowing the expression of wild type or mutated CD8-CD™ at cysteine residues 1, 2 and 3 (abbreviated to: CCC). The cysteine residues were then replaced or not replaced by alanine residues, which cannot be palmitoylated. The wild type or mutated CD8-CD™ proteins studied were:
1: pX2 CCC (wild type phenotype)
2: pX2 ACC
3: pX2 CAC
4: pX2 AAC
5: pX2 CCA
6: pX2 ACA
7: pX2 CAA
8: pX2 AAA
9: pX3 CCC (wild type phenotype)
10: pX3 CAC
11: pX4 - - C (wild type phenotype)
12: pX4 - - A
13: pX4 stp (pX4 stp is composed solely of ED, tmD and a small portion of the CD™ of CD8).

These constructs allowed analysing, at the level of the targeting of the TM protein: the consequences of the mutation of cysteine residues, the importance of the integrity of the trans-membrane domain of the TM protein, and the importance of the cytoplasmic domain of the TM protein (CD™).

I. Preparation of Plasmid DNA:

Initially, we produced large quantities of each of our 13 DNAs as well as a vector with no insert (pLPCX) acting as a negative control. After culture of bacteria transformed by our various plasmids, the DNA obtained was purified in succession by the STET method then on a column. The identity of the plasmids obtained was then checked by enzymatic digestion.

Figure 3:
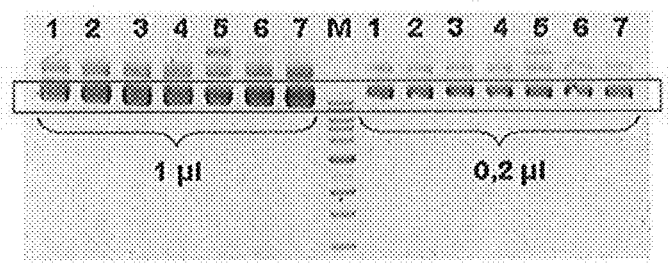
FIG. 3: Preparations of DNAs using the STET method. Numbers 1 to 7 correspond to the sample numbers for the STET products. "M" represents the size marker. The bands corresponding to super-coiled plasmid DNA are surrounded by a box.

A. DNA Preparations by the STET Method:

In order to verify the integrity of the plasmid DNA and the yield of the STET preparations, we carried out a migration of 1 µl and 0.20 µl of each of them on agarose gel (0.8%; see FIG. 3). The non-degradation of the DNA is demonstrated by the presence of distinct bands of super-coiled DNA with homogeneous sizes.

Figure 4:
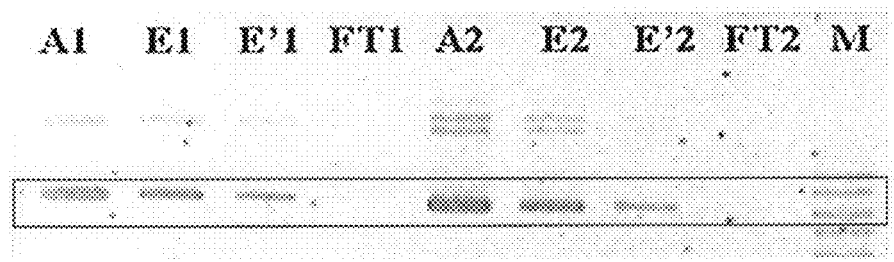
FIG. 4: Monitoring the presence of DNA in the column purification products.

B. Checking the Presence of DNA in the Column Purification Products:

The DNA obtained by the STET method was purified on columns; the retained then eluted fractions as well as the non-retained fractions were then analyzed by gel electrophoresis in order to verify the integrity of the purified DNA obtained. The gel presented in FIG. 4 shows us that super-coiled DNA was indeed present in the pure fractions eluted from columns (E and E') but was undetectable in the non-retained fractions (FT).

C. Spectrometric Assays of Aliquots and Adjustment of DNA Concentrations After Enzymatic Digestion:

The purified DNA was then assayed by spectrophotometry. The concentrations thus obtained varied, as a function of the aliquots, between 149 µg/mL and 584 µg/mL. After precipitation with EtOH, the DNA from the aliquots was taken up in TE1× and adjusted to the same concentration.

In order to verify the concentrations of DNA, we linearized the plasmids by enzymatic digestion using the Hind III/Not I pair, then we analyzed them by gel electrophoresis (see FIG. 5, top profile). It can be seen that the intensity of the bands obtained were still variable. We thus readjusted the concentrations as a function of the spectrometric assays and the intensity of the bands obtained after digestion (see FIG. 5—lower profile). The obtention of bands of equal intensities, in addition to showing the accuracy of the concentrations of our DNA before, transfecting them into cells, will allow achieving a better readability of the electrophoresis measurements following enzymatic digestion when checking the identity of the plasmids.

D. Checking the Identity of the DNA After Enzymatic Digestion.

1) General Principle:

In order to check the identity of the 14 DNA prepared, they were all checked by digestion with the aid of the restriction enzymes Hind III and Not I, Xba I, Aat II, Pac I as well as Sfo I, which should result in different combinations of gel profiles for each DNA. Agarose gel (0.8%) migration of the digestion products allowed the DNA to be differentiated as a function of the number and size of the bands obtained, as indicated in Table 1 (NB: bands smaller than a hundred base pairs in size were not visible on our electrophoresis gels):

Expected Size of Bands (bp):

(a): 7206/49
(b): 6868/311
(c): 7162
(d): 6937
(e): 6822/367/66
(f): 6812/367
(g): 6552/610
(h): 6552/385
(i): 4285/1055/801/498/294/186/83/53
(j): 3423/1055/862/801/294/186/83/53
(k): 4276/2538/310/131
(l): 4276/1839/699/310/131

2) Example:

For the differentiation of mutants pX2 AAC and pX2 CCA, the gels obtained are shown in FIG. 6A.

Interpretation:

Digestion with Hind III/Not I: single band obtained, at approximately 7206 bp, corresponds to the presence of constructs X2 or X4 in each of the two samples.

Digestion with XbaI: obtaining two bands at approximately 6822 (or 6812) and 367 by corresponded to the presence of constructs X2 or X3 in each of the two samples.

These two results cross-check and confirm that we were indeed in the presence of two constructs of type X2.

We then sought to differentiate the X2 mutants among themselves (see FIG. 6B):

Interpretation:

Digestion with AatII:

Sample 4: obtaining one specific band of approximately 3423 by (red), corresponds to the presence of one of the following X2 plasmids: pX2 CAC, pX2 AAC, pX2 CAA or pX2 AAA.

Sample 5: obtaining one specific band of approximately 4285 by (blue) corresponds to the presence of one of the following X2 plasmids: pX2 CCC, pX2 ACC, pX2 CCA or pX2 ACA.

Digestion with Sfo I:

Sample 4: obtaining one specific band of approximately 2538 by (red) corresponds to the presence of one of the

TABLE 1

| N° Plasmid | | Theoretical numbers of bands obtained after digestions | | | | | | | |
|---|---|---|---|---|---|---|---|---|---|
| | | Hind III/Not I | | Xba I | | Aat II | | Sfo I | Pac I |
| 1 | pX2 wt TM | 2 | | 3 | | 8 | (i) | 4 | 0 |
| 2 | pX2 MCA | 2 | | 3 | | 8 | | 4 | 1 |
| 3 | pX2 M2 | 2 | | 3 | | 9 | (j) | 4 | (k) 1 |
| 4 | pX2 M14 | 2 | | 3 | | 9 | | 4 | 0 |
| 5 | pX2 M15 | 2 | (a) | 3 | (e) | 8 | | 5 | 0 |
| 6 | pX2 M16 | 2 | | 3 | | 8 | | 5 | 1 |
| 7 | pX2 M17 | 2 | | 3 | | 9 | | 5 | (l) 1 |
| 8 | pX2 M18 | 2 | | 3 | | 9 | | 5 | 0 |
| 9 | pX3 wt TM | 2 | (b) | 2 | (f) | 8 | | 4 | 0 |
| 10 | pX3 M15 | 2 | | 2 | | 9 | | 4 | 1 |
| 11 | pX4 wt TM | 1 | (c) | 2 | (g) | 8 | | 4 | 0 |
| 12 | pX4 M15 | 1 | | 2 | | 8 | | 5 | 0 |
| 13 | pX4 Stp | 1 | (d) | 2 | (h) | 8 | | 4 | 0 |

Digestion of the constructs studied was used to confirm the identity of each plasmid. The large CD8-CD™ construct types were differentiated by number and size analysis of the bands obtained after digestion with the enzymes Hind III/Not I and Xba I. The various cysteine residue mutants were differentiated after digestion with the enzymes Aat II, Pac I and Sfo I. The number of bands thus obtained was larger than with the digestions with Hind III/Not I and Xba I, and differentiation was principally carried out based on the presence or absence of specific bands (in bold).

following X2 plasmids: pX2 CCC, pX2 ACC, pX2 CAC, pX2 AAC.

This result cross-checks with that of digestion with Aat II, and so we could deduce therefrom we were in the presence of one of the following plasmids: pX2 AAC or pX2 CAC.

Sample 5: obtaining 2 specific bands of approximately 1839 by (black) and 699 (green) by corresponds to the presence of one of the following X2 plasmids: pX2 CCA, pX2 ACA, pX2 CAA, pX2 AAA. This result cross-checks with that of digestion with Aat II, and so we could then deduce that we were in the presence of one of the following plasmids: pX2 CCA or pX2 ACA.

Digestion with Pac I:

For each sample, we obtained one low intensity band corresponding to non super-coiled DNAp as well as a high intensity band corresponding to our super-coiled DNAp (blue), demonstrating the absence of digestion with Pac I for these sample.

Samples 4 and 5 correspond respectively to mutants pX2 AAC and pX2 CCA.

This process was applied to the identification of all of the plasmids.

3) Conclusion:

During this step for preparing DNA, we obtained several milligrams of each of the 14 purified plasmids and their identities were all confirmed after checking by enzymatic digestions and gel analyses. Further, all of the DNA have been adjusted to the same concentration.

II. Analysis of the Expression of Chimeras:

In order to evaluate DNA expression, the same quantity of each of the plasmids was transfected into HEK293 cells. The proteins expressed thereby were analyzed by gel migration followed by a transfer onto PVDF membrane. The membranes were then revealed with the aid of an anti-rabbit CD™ serum and of a secondary Anti-Rabbit antibody labelled with peroxidase.

A. Analysis of the Presence of CD8-CD™ in Cell Lysates:

1) Analyses of Crude Lysates:

After 48 h of transfection, the cells are lysed and the extracts obtained were assayed using the Bradford technique. We analyzed 200 µg of crude proteins brutes, derived from these lysates, by gel migration and Western Blot revealed with an anti-CD™ antibody (see FIG. 7).

Various specific signals could then be observed in the samples:
- a double band at 50 kDa (blue) corresponding to the presence of CD8-CD™. The two bands correspond to two levels of glycosylation of CD8.
- a signal at approximately 20 kDa (red) of indeterminate origin.

The samples pX2 CCC, pX2 ACC, pX2 CAC, pX2 AAC, pX4 stp and pLPCX did not have these bands.

2) Analysis of Lysates After Immunoprecipitation by Anti-CD8 Antibodies:

In order to reduce the detection threshold for CD8-CD™ in cell lysates, we used a large quantity of extract and concentrated the chimeras by immunoprecipitation with specific monoclonal antibodies of a conformational epitope of the ectodomain of CD8.

After 48 h of transfection, the cells were lysed and the extracts obtained were assayed using the Bradford technique. After normalisation of the protein concentrations, the extracts were immunoprecipitated in the presence of Anti-CD8 antibody and protein A sepharose. The products obtained were analyzed by gel migration and Western Blot, and revealed with a anti-CD™ antibody (see FIG. 8). Various signals could then be observed in the samples:
- a double band at 55 kDa (blue), corresponding to the presence of CD8-CD™;
- an unidentified signal, found for each sample, at approximately 66 kDa;
- one or several signals with a molecular weight greater than 66 kDa, probably corresponding to the presence of multimerized CD8-CD™ proteins.

In this case, the pX2 AAC sample had a detectable signal at 50 kDa, in contrast to the analysis carried out without immunoprecipitation. In contrast, no signal was detectable for the samples pX2 CCC, pX2 ACC, pX2 CAC, pX4 stp and pLPCX.

3) Summary of the Analysis of the Expression of CD8-CD™ in Cell Lysates:

By correlating the data obtained by Western Blot on the cell lysates with the characteristics of each chimera (integrity of tmD BLV, presence of third cysteine residue and number of cysteine residues), we could draw up Table 2 below.

It appears that, in addition to CD™ of BLV, two factors may act on the presence of CD8-CD™ chimeras. These factors are: the presence or not of tmD BLV, and the presence or not of the third cysteine residue (Cys 213).

TABLE 2

| Construct | tmD DLV | Number of cysteines | Signal CD ™ BLV |
|---|---|---|---|
| pX2 CCC | Complete | 3 | None |
| pX2 ACC | Complete | 2 | None |
| pX2 CAC | Complete | 2 | None |
| pX2 AAC | Complete | 1 | + |
| pX2 CCA | Complete | 2 | ++++ |
| pX2 ACA | Complete | 1 | ++++ |
| pX2 CAA | Complete | 1 | ++++ |
| pX2 AAA | Complete | 0 | ++ |
| pX3 CCC | - 15 AA | 3 | +++ |
| pX3 CAC | - 15 AA | 2 | +++ |
| pX4 --C | Absent | 1 | ++++ |
| pX4 --A | Absent | 0 | +++++ |
| pX4 stp | Absent | 0 | None |
| pLpcX | Absent | 0 | None |

B. Analysis of the Association of CD8-CD™ with Exosomes:

The various DNA used only varied by a few nucleotides. It is thus probable that the quantities of CD8-CD™ synthesised were equivalent. However, during the analysis of the expression of CD™ in cell lysates, it was observed that certain chimeras were not detectable 48 h post-transfection. This absence of a signal could reflect the disappearance of some of our chimeric proteins. This disappearance could be due either to a rapid degradation of these chimeras, or to their secretion in the form of exosomes.

We thus sought to detect the presence of CD8-CD™ within exosomes.

1) CD8-CD™ Content in Vesicles Isolated by Centrifuging:

After 48 h of transfection, the culture media were recovered and centrifuged in order to isolate the exosomes. The residues obtained were then analyzed by gel migration and Western Blot and revealed with a anti-CD™ antibody (see FIG. 9).

Some samples exhibited a signal at 55 kDa corresponding to the presence of CD8-CD™. This signal is not detectable for the samples pX2 CCC, pX2 ACC, pX2 CAC, pX2 AAC, pX4 stp and pLPCX.

2) CD8-CD™ Content After Sedimentation of Vesicles on Sucrose Density Gradient:

In order to confirm that the signal obtained after ultra-centrifuging the culture media was indeed due to the presence of chimeras in the exosomes and not to the presence of cellular debris containing CD8-CD™, we analyzed the residues of exosomes obtained according to the method described above by sedimentation on a sucrose density gradient. The exosomes floated at a density of 1.13 g/mL to 1.20 g/mL as a function of cells used and the composition of the vesicles. After sedimentation by ultracentrifuging, the gradient was removed in 700 µl fractions. The proteins were precipitated using TCA and analyzed by gel migration then Western Blots and revealed with a anti-CD™ antibody and an anti-transferrin receptor (RTf) antibody to detect the presence of cellular vesicles (endosomes or exosomes). This analysis was carried out for the mutants pX4 -C and pX4 --A. (see FIG. 10).

In pX4 --C and pX4 --A, a signal corresponding to CD8-CD™ was detected in fractions with a density of 1.13 g/mL to 1.25 g/mL. For these same densities, we were also able to detect a signal corresponding to RTf. These results reveal the presence of CD8-CD™ in the fractions containing the exosomes.

3) Summary of the Analysis of the Association of Exosomes with CD8-CD™:

The association of CD8-CD™ with the exosomes was detected for all of the mutants containing CD™ except for the pX2 with Cys 213. The pX4 --C and pX4 --A mutants appeared to have been very efficiently targeted in the exosomes. The pX3 and pX2 mutants without Cys 213 were also found in the exosomes, but in smaller proportions than for the pX4 --C and pX4--A mutants.

It thus appears that, in addition to the presence of viral CD™, two factors may act on the targeting of CD8-CD™ chimeras in exosomes.

These factors are:
the presence or not of the transmembrane domain of BLV.
the presence or not of Cys 3.

C. Influence of Inhibiting Vesicular Transport on the Expression of CD8-CD™ Chimeras:

Since the absence of detection of the chimeras pX2 CCC, pX2 ACC, pX2 CAC and pX2 AAC was not due to increased exosomal secretion, we investigated whether it could be due to degradation by sorting of MVB proteins to the lysosomes.

To this end, we used vesicular transport inhibitors, namely bafilomycin and Ly294002. These inhibitors can block the lysosomal degradation pathway, thereby encouraging the secretion of proteins by the exosomes. The inhibitors were added to the culture media 32 h post-transfection; 16 h later, the cells were lysed and the culture media were recovered then centrifuged to isolate the exosomes. The samples obtained were then analyzed by gel migration and revealed by Western Blot with a anti-CD™ antibody. We thus analyzed the expression of the chimeras pX2 CCC, pX2 CCA, pX3 CCC, pX4 -- C, pX4 -- A and pX4 stp (see FIGS. 11 and 12).

It appears that, for these mutants, the Western Blot profiles for the proteins obtained in the presence of inhibitors were the same as during the analysis without inhibitor, both for the cell lysates and for the exosomes.

The absence of the chimeras pX2 CCC, pX2 ACC, pX2 CAC and pX2 AAC is thus apparently due neither to an accelerated exosomal exit, nor to a degradation in the lysosomes. It is probable that it is the consequence of a very early degradation at the level of the system for controlling folding in the endoplasmic reticulum (RE) and TGN.

III. Localisation by Immunofluorescence:

In order to assess the membrane targeting of CD8-CD™ as well as its localisation in the cell compartments, we carried out observations using confocal immunofluorescence microscopy. 48 h post-transfection, the cells were fixed then labelled using various antibodies.

A. Choice of Antibodies:

Initially, each type of label (see Methods and Apparatus) was tested using variable antibody dilutions on fixed cells expressing pX4 -- C or pLPCX. After observation on a conventional immunofluorescence microscope (ZEISS Axiovert 200 M), we tested the various available antibodies (see "Methods and Apparatus" section) and determined their efficacy as well as their optimum dilutions. It was seen that several anti-intra-cell compartments antibodies had a zero or aspecific signal.

For confocal imagery observation, we could thus use only two types of labels:
CD8-CD™ Label:
rat IgG (53/6.7) anti-mouse CD8 FITC (Pharmingen, dilution 1/50)
Lamp3 Label:
Anti-human CD63 (Lamp3) mouse IgG (Zymed, dilution 1/50)+anti-mouse IgG Cy3 (Sigma, dilution 1/500)

B. Observations of the Distribution of CD8-CD™:

After fixing and labelling the cells using our various antibodies, we observed the distribution of labelling derived from CD8-CD™ as well as its co-localization with Lamp3 with the aid of a confocal microscope (ZEISS LSM 510).

The cells expressing pLPCX (negative control) did not exhibit a FITC signal. This control thus allowed us to confirm that the FITC fluorescence visualised for the other mutants was indeed derived from the presence of CD8-CD™.

Surprisingly, despite an absence of detection by Western Blot, the pX2 constructs comprising Cys 3 were visible, albeit weakly, in immunofluorescence.

Analysis of General Phenotypes:

The HEK293 cells were transfected for 48 h then fixed. Observation was carried out with the aid of a ZEISS LSM 510 confocal microscope (X63 immersion objective).
CD8: FITC label (green) revealed the presence of chimeras containing CD8.
Lamp3: Cy3 label (red) revealed the presence of the Lamp3 protein characteristic of late endosomes.
CD8-CD™/Lamp3: Superimposition of FITC and Cy3 images. The yellow shade obtained proves the co-localization of CD8-CD™ with Lamp3.

From the observations, we can distinguish 5 general phenotypes (see FIGS. 13 to 17) based on the appearance (vesicular, membrane or perinuclear) and intensity of the FITC label. The co-localization of the FITC label for vesicular appearance with Lamp3 cannot be used for the determination of these phenotypes since this exists in all of the mutants. Furthermore, this co-localisation was always partial.

Analysis of Perinuclear Zones Having a Strong FITC Signal:

For all of the samples except pX4 stp, a large homogeneous CD8 perinuclear signal was almost always found at the periphery of the nucleus. The intensity parameters required to visualize the major portion of the FITC fluorescence present in the cells caused saturation of this zone. Such a saturated signal is not very useful, and so we captured weaker intensity parameters by concentrating on an analysis of these zones, in particular in order to determine the pertinence of the co-localizations they have with Lamp3.
CD8-CD™/Lamp3 [a]: Co-localization of CD8-CD™ (green) with Lamp3 (red). The intensity parameters for acquisition, while weak, caused saturation of the perinuclear signal and the appearance of yellow shades at this level, demonstrating partial co-localization between these two labels. Because of the signal saturation, it was impossible to say whether the co-localization occurring was real or artificial.
CD8-CD™ [d]: FITC signal from CD8-CD™. The intensity parameters were substantially reduced in order to eliminate any signal saturation phenomenon. The FITC signal appeared diffuse, homogeneous and not punctuated.

CD8-CD™/Lamp3 [d]: Co-localization of CD8-CD™ (green) with Lamp3 (red). The intensity parameters were substantially reduced in order to eliminate any signal saturation phenomenon. This resulted in an absence of yellow shades, demonstrating the absence of co-localization between FITC and Lamp3.

According to this data, the labelling derived from Lamp3 appeared to be located inside this perinuclear zone, but it was never co localized with the FITC label (see FIG. 18).

Furthermore, the labelling derived from CD8-CD™ of these perinuclear zones appeared diffuse, homogeneous and not punctuated, and appeared to demonstrate the presence of CD8-CD™ within a cellular structure. The localisation and appearance of this labelling, as well as the absence of genuine co-localization with Lamp3, suggest the presence of CD8-CD™ in the Golgi apparatus.

This phenotype is found, to a greater or lesser extent, in all mutants except for pX4 stp. In pX4 --C and pX4 -A mutants, this phenotype is only visible in a minority of cells, in contrast to the mutants pX2 and pX3 in which it is always present.

Thus, the specific observation of perinuclear zones strongly labelled by FITC allowed us to demonstrate the probable presence of CD8-CD™ in TGN.

We used the data obtained to construct the table below (see Table 3).

These observations confirm that, in addition to viral CD™, two factors play a role in the stability and targeting of our chimeras.

These factors are:
the presence or not of tmD BLV;
the presence or not of the N-terminal residues of BLV CD™;
the presence or not of Cys 3.

TABLE 3

| | | Localization of FITC labelling | | |
| --- | --- | --- | --- | --- | --- |
| Phenotype | Mutants | FITC intensity | Vesicular | Membrane | TGN |
| A | pX2 CCC | + | +++ | — | ++ |
| | pX2 ACC | + | +++ | — | ++ |
| | pX2 CAC | + | +++ | — | ++ |
| | pX2 AAC | + | +++ | — | ++ |
| B | pX2 CCA | +++ | ++++ | — | ++ |
| | pX2 ACA | +++ | ++++ | — | ++ |
| | pX2 CAA | +++ | ++++ | — | ++ |
| | PX2 AAA | +++ | ++++ | — | ++ |
| C | pX3 CCC | ++++++ | + | +++ | +++++ |
| | pX3 CAC | ++++++ | + | +++ | +++++ |
| D | pX4 --C | ++++++ | ++ | ++++ | + |
| | pX4 --A | ++++++ | ++ | ++++ | + |
| E | pX4 stp | ++++ | + | +++ | — |

Conclusion:

During our analyses, it has been shown that the chimera pX4 stp, composed solely of the ectodomain and the tmD of CD8, accumulate in HEK293 cells by being efficiently targeted to the plasma membrane.

In the same manner, the chimeras pX4 --C and pX4 --A accumulate and are found in the plasma membrane, but in larger proportions than pX4 stp. These chimeras are secreted very effectively within the exosomes.

The pX3 chimeras are definitely present in the Golgi apparatus, in contrast to the pX4 chimeras. Their targeting in the plasma membrane and in the exosomes appears less effective than in the pX4 chimeras, but remains considerable.

The pX2 chimeras appear less stable and are found in TGN but not in the plasma membrane. The pX2 constructs comprising Cys 3 are much less stable in the cells and are not detected in the exosomes. Substitution of the terminal Cys in this type of construct appears to contribute to a gain in stability of the chimeric proteins. In fact, the pX2 constructs without Cys 3 are detectable in the cells and in the exosomes.

In immunofluorescence, all of the chimeras studied have a vesicular label which is partially co-localized with a marker for late endosomes.

This study has shown the importance of the presence or not of Cys 3 in the stability and in the targeting of CD8-CD™ chimeras. It appears that the absence of this cysteine residue favours stability and the membrane targeting of the chimeras studied as well as their presence in the exosomes. These phenomena could be independent of the hyperpalmitoylation associated with the absence of Cys 3. In fact, the construct pX2 AAC, which is non palmitoylated, is more stable than the three pX2 mutants having Cys 3 as well as Cys 1 and/or Cys 2, which can be palmitoylated. However, a different implication of palmitoylation in the stability and targeting of our chimeras cannot be excluded.

This study has shown the fundamental importance of BLV tmD. In fact, the deletion of all or part of the tmD BLV appears to substantially increase the stability of the chimeras as well as their targeting in the plasma membrane. Thus, surprisingly, the presence of tmD BLV could contribute to the early degradation of the chimeras. This degradation could interfere in the system controlling folding in the cell compartments, namely the RE and TGN, since the lysosomal degradation pathway is not the cause. The absence of vesicular transport inhibitor effects on the stability and exosomal targeting of CD8-CD™ chimeras as well as their very partial co-localization with late endosomes, even for the least stable chimeras, supports this hypothesis.

The principle attraction of our studies resides in the discovery of potentially effective tools for the development of a mode of vaccination based on the concept of "exosome display". In fact, the pX4 --C and especially pX4 --A chimeras appear to have a molecular "machinery" that allows highly effective targeting of the peptide antigen (here CD8) to the exosomes. This "machinery" would thus be located in the cytoplasmic domain of the TM protein of BLV.

Example 2

Identification of Amino Acids Involved in Exosomal Targeting of CD™ Peptide

In order to determine the exact nature of the "machinery" located in the cytoplasmic domain of the BLV TM protein before proceeding to the first immunization trials, we studied the effect of 18 types of mutations in the cytoplasmic domain of the BLV TM protein (see FIG. 19):
deletion of the 13 N-terminal residues and substitution of the 2 proline residues of the first PxxP motif (SEQ ID NO: 13 and SEQ ID NO: 14; mutation KM4);
deletion of the 13 N-terminal residues and substitution of the 2 proline residues of the second motif PxxP (SEQ ID NO: 15 and SEQ ID NO: 16; mutation KM5);
deletion of the 13 N-terminal residues and substitution of the 2 proline residues of the third PxxP motif (SEQ ID NO: 17 and SEQ ID NO: 18; mutation KM8);
deletion of the 13 N-terminal residues and substitution of the first proline residue of the fourth PxxP motif (SEQ ID NO: 19 and SEQ ID NO: 20; mutation KM11/1);

substitution of the 2 proline residues of the fourth PxxP motif (SEQ ID NO: 21 and SEQ ID NO: 22; mutation KM11/3);

deletion of the 13 N-terminal residues and substitution of the tyrosine residue of the first YxxL motif (SEQ ID NO: 23 and SEQ ID NO: 24; mutation KTMY);

deletion of the 13 N-terminal residues and substitution of the tyrosine residue of the second YxxL motif (SEQ ID NO: 25 and SEQ ID NO: 26; mutation KM9);

deletion of the 13 N-terminal residues and substitution of the tyrosine residue of the third YxxL motif (SEQ ID NO: 27 and SEQ ID NO: 28; mutation KM13);

deletion of the 13 N-terminal residues and substitution of the serine residue before the first YxxL motif (SEQ ID NO: 29 and SEQ ID NO: 30; mutation S);

deletion of the 13 N-terminal residues and substitution of the glutamic acid residue located before the second YxxL motif (SEQ ID NO: 31 and SEQ ID NO: 32; mutation E);

deletion of the 13 N-terminal residues and substitution of the aspartic acid residue located before the third YxxL motif (SEQ ID NO: 33 and; SEQ ID NO: 34; mutation D);

sequence truncated to 6 residues—deletion of the 13 N-terminal residues and of the 39 C-terminal residues (SEQ ID NO: 35 and SEQ ID NO: 36; mutation KS5);

sequence truncated to 15 residues—deletion of the 13 N-terminal residues and of the 30 C-terminal residues (SEQ ID NO: 37 and SEQ ID NO: 38; mutation KS6);

sequence truncated to 21 residues—deletion of the 13 N-terminal residues and of the 24 C-terminal residues (SEQ ID NO: 39 and SEQ ID NO: 40; mutation KS8);

sequence truncated to 26 residues—deletion of the 13 N-terminal residues and of the 19 C-terminal residues (SEQ ID NO: 41 and SEQ ID NO: 42; mutation KS9);

sequence truncated to 31 residues—deletion of the 13 N-terminal residues and of the 14 C-terminal residues (SEQ ID NO: 43 and SEQ ID NO: 44; mutation KS10);

sequence truncated to 37 residues—deletion of the 13 N-terminal residues and of the 8 C-terminal residues (SEQ ID NO: 45 and SEQ ID NO: 46; mutation KS12);

sequence truncated to 41 residues—deletion of the 13 N-terminal residues and of the 4 C-terminal residues (SEQ ID NO: 47 and SEQ ID NO: 48; mutation KS14).

The substitution and deletion mutants were obtained by directed mutagenesis; the substituted residues were replaced by an alanine residue. Translation of the deletion mutants was halted by addition of a stop codon (TGA, TAG or TAA codon).

The DNA sequences coding for the 18 mutants, as well as the wild type DNA CD™ sequence in which only the 13 N-terminal residues had been deleted (SEQ ID NO: 7; sequence termed "wild type sequence" hereinafter) were sub-cloned downstream of a sequence coding for the ectodomain of murine CD8α. The 19 chimeric genes obtained were then cloned into a viral expression vector. The recombinant vectors obtained thereby were transfected into eukaryotic cells (HEK cells) in order to analyze targeting to the exosomes of the resulting chimeric proteins. 48 hours later, protein expression in the cells was examined by Western Blot. At the same time, the exosomes were purified by ultracentrifuging in order to evaluate sorting of the chimeric protein in the exosomes by FACS and Western Blot.

The results shown below demonstrate the need for two peptide motifs individually recognized in the literature for their interactions with the proteins associated with the ESCRT machinery and with the intermembrane transfer machinery (in particular adaptins including AP3).

This is the first time that experimental evidence has been provided that these two peptide motifs have a synergistic, determining role in exosomal targeting.

These results provide novel and important information in terms of intercellular signalling using exosomes. Thus, we have a clearly defined tool to hand for targeting proteins with exosomes. From an industrial viewpoint, they will facilitate the production of a new generation of vaccine and provide a unique tool for screening therapeutic molecules or antibodies, for example.

1—Obtaining Molecular Constructs

A—Preparation of Inserts by PCR:

The three substitution mutants S (Ser→Ala), D (Ac. Asp→Ala) and E (Ac.Glut→Ala) were obtained by directed mutagenesis using a double PCR employing the following mutation primers:

```
Primer S to A, sense:
5' CCCTAAACCCGATGCTGATTATCAGGCGTTGCTACCATCC 3'

Primer S to A, anti-sense:
5' CGCGGATGGTAGCAACGCCTGATAATCAGCATCGGGTTTA 3'

Primer D to A, sense:
5' CCACCAAGCCGGCATACATCAACCT 3'

Primer D to A, anti-sense:
5' TCGAAGGTTGATGTATGCCGGCTTGGT 3'

Primer E to A, sense:
5' GCTACCATCCGCGCCAGCGATCTAC 3'

Primer E to A, anti-sense:
5' GTAGATCGCTGGCGCGGATGGTA 3'.
```

The PCR was carried out using the Expand High Fidelity PCR system kit (Roche®) which had an enzymatic mixture containing thermostable Taq DNA polymerase and a thermostable Tgo polymerase provided with a corrective activity (3'-5'-exonuclease) to limit errors during polymerisation and obtain fragments with blunt ends. Two mixtures of reagents were prepared at 4° C.:

A (25 µL):10 ng of DNA to be amplified, 1 µL of 10 mM dNTP (200 µM final each), 1.5 µL of each of the two sense and anti-sense primers, at 10 µM (300 nM final), sterile water (qsp 25 µL); and B (25 µL):5 µL of "Expand High Fidelity" buffer, 10× with 15 mM MgCl$_2$ (1.5 mM final), 0.75 µL of "High Fidelity" enzyme mixture (2.6 U final), sterile water (qsp 25 µL).

A and B were mixed at 4° C. then the following amplification cycles were carried out:

denaturing of the double strand DNA, 2 minutes at 94° C.;

4 cycles of denaturing (94° C., 10 seconds), hybridization (50° C., 15 seconds) and elongation (72° C., 20 seconds);

25 cycles: 10 seconds at 94° C., 15 seconds at 64° C. then 20 seconds at 72° C.;

final elongation for 7 minutes at 72° C.

The PCR product obtained was kept at 4° C.

The DNA sequences coding for the 18 mutants, as well as the wild type DNA sequence were modified by PCR (directed mutagenesis) so that they were framed by particular restriction sites; the protocol indicated above was carried out using two primers having the restriction sites XbaI and NotI.

B—Cloning of PCR Products in TOPO-bluntII and Controls

Each of the 19 DNAs was ligated into a TOPO cloning vector (see FIG. 20) of the Topo-blunt cloning kit (Invitrogen) for introduction into chemocompetent bacteria. The transformed clones were selected and all of the DNA sequences were verified by sequencing.

a) Ligation into the Plasmid and Transformation in Top10

Each of the various PCR products was integrated into a TOPO-BluntII plasmid that was already open and had blunt ends and carried the kanamycin resistance gene. The chemocompetent Top10 bacteria were transformed by these plasmids and cultured on LB/agar dishes (100 μg/mL of kanamycin). The TOPO-BluntII plasmid with no insert acted as a negative control and another control (1 ng of PUC19 plasmid) was used as the positive control for transformation. After culture, only the bacteria transformed by a plasmid containing the insert or PUC19 (positive control) developed in the presence of the selection agent (antibiotic).

b) Targeting of Good Clones and Sequencing:

Depending on the cloning results, 2 to 10 colonies were amplified to carry out extraction of the plasmid DNA. For each construct and each clone, we obtained a plasmid DNA volume of 100 μL at approximately 150 ng/μL. The absorption at 260 nm/absorption at 280 nm ratio for each purification had a value in the range 1.8 to 2, providing evidence of the purity of the preparation (a value of less than 1.8 provides evidence of protein contamination).

In order to confirm the presence of an insert in the plasmid, the plasmid DNA was digested by the EcoRI restriction enzyme which framed the sequences of interest. These digestion were visualized on 2% agarose gel where the presence of a fragment (of approximately 300 pb) constituted proof of recombinant DNA.

Once good clones had been identified, 2 μg to 4 μg of plasmid DNA from each mutant was sequenced to check the integrity of each sequence of interest and thus of the open reading frame. The mutations and restriction sites added were checked at the same time.

C—Obtaining Chimeric Genes in a pKSII Cloning Vector

Each of the 19 sequences (1 wild type and 18 mutated) was placed downstream of a sequence coding for the mouse CD8α ectodomain, to provide 19 constructs.

a) Preparation of a pKSII-CD8 Cloning Vector

The pKSII-CD8α vector (see FIG. 22) was digested in succession with the restriction enzymes XbaI and NotI so that it could accommodate the inserts. Once the digestions had been carried out, the plasmid was dephosphorylated, precipitated with ethanol and purified on 0.8% agarose gel.

b) Preparation of Inserts

The various inserts framed by the XbaI-NotI restriction sites were digested with the same restriction enzymes as the plasmid so that it could integrate them.

c) Obtaining Chimeric Plasmids by Cloning

The DNAs were inserted in the linearized pKSII-CD8α plasmid:

The digested inserts were purified on 2.5% agarose gel. Their reinsertion in the pKSII-CD8α vector was carried out using the gel ligation technique. A fragment of virgin gel acted as the negative ligation control.

Having used the same restriction enzymes for the vector and the inserts, they thus had cohesive, complementary XbaI and NotI sites: the plasmid and inserts should be able to establish bonds between them. One enzyme, ligase, catalyses the formation of a phosphodiester linkage between a 3'-OH end and a 5'-Phosphate end of two nucleic acids.

Once the ligation step is complete, the DH5α bacteria were transformed by these plasmids carrying the ampicillin resistance gene. After culture of the various bacteria transformed at 37° C. on LB/agar (50 μg/mL of ampicillin) and comparison with the negative controls, colony development was observed only on cells transformed by the ligation products in the presence of the CD™ insert. This suggests that the colonies obtained had indeed been transformed by a vector containing an insert between the XbaI and NotI sites.

d) Screening:

In order to confirm that chimeric plasmids had been obtained, various clones of each mutant were screened by digesting plasmid DNA with the two enzymes, XhoI/NotI, and after migration of the digestion products on 0.8% agarose gel. This double digestion excises all of the created chimeric gene, i.e. with the CD8α in phase with the CD™.

For each clone and each construct (mutated or wild type pKSII-CD8α-CD™), a first band at 2.9 kbp corresponding to the size of the linearized pKSII plasmid was observed. A second band was noted at approximately 950 bp; it corresponded to the gene coding for the mutated or non-mutated CD8α-CD™ chimeras.

D—Obtaining Chimeric Genes in the Retroviral Expression Vector pLPCX:

While it is easy to manipulate because of its size and its restriction sites, the expression vector pKSII does not allow protein expression in eukaryotic cells. We therefore selected pLPCX (Clontech Laboratories Inc., see FIG. 23), which meant that a gene could be introduced both by transfection and by transduction using a retroviral vector.

Each chimeric gene was excised from the pKSII plasmid between the XhoI-NotI sites for purification by extraction on 2% agarose gel using the Nucleospin Extract II® kit (Macherey-Nagel).

The expression vector pLPCX had also been digested by the XhoI-NotI enzyme pair, dephosphorylated then precipitated with isopropanol (this step was to eliminate the short fragment of DNA (less than 100 pb) situated between XhoI and NotI liberated during digestion).

The ligation of chimeric genes with pLPCX was carried out using T4 DNA ligase (Biolabs) (insert/vector ratio of approximately 3/1 molecule to molecule). Chemo-competent Stbl2 bacteria (MAX Efficiency® Stbl2™ Competent Cells, Invitrogen) were transformed by these ligation products. A positive control (1 ng of the pUC19 plasmid) and a negative control (pLPCX "ligated" without insert) were prepared at the same time. After bacterial culture at 30° C. on gelose medium containing 50 μg/mL of ampicillin, only the bacteria transformed by the positive control or by the ligation products with inserts had developed.

In order to be able to proceed to screening and have a sufficient quantity of DNA plasmid necessary for the transfections in eukaryotic cells, Midipreparations were carried out. The presence of inserts in the plasmid was verified on 2% agarose gel after digestion with XhoI then NotI. For each construct (mutated and wild type pLPCX-CD8α-CD™; see FIG. 24), a band at 6.3 kpb corresponding to linearized pLPCX and a band at 950 pb corresponding to the chimeric genes excised were observed.

2—Expression and Analysis of Targeting to Exosomes:

A—Transfections in HEH 293T Cells:

In order to confirm the transfection of HEK 293T eukaryotic cells and estimate the percentage of transduced cells, the cells were transfected by the plasmid containing the LacZ gene and incubated in a solution of X-Gal.

Initially by eye and then by observation with an optical microscope (magnification X40), we observed that more than 50% of the cells had been stained blue, which proved that the great majority had been transduced by LacZ plasmid. The same conditions had been applied as for the transfection of our chimeric genes, and so it was probable that more than 50% of the cells had been transduced by the chimeric genes.

At the same time, twenty simultaneous transfections were carried out in HEK 293T cells. They corresponded to each of the plasmids and to a negative control (pLPCX-CD8 without CD™).

B—Expression of Chimeric Proteins in the Cell and Targeting to the Exosomes a) Western Blot Analysis:

The cell and exosomal lysates derived from the transfections were analyzed by 10% SDS-PAGE gel migration, followed by a transfer onto PVDF membrane (polyvinylidene difluoride, Immobilon-P, Millipore). These membranes were then revealed with the aid of a primary anti-rabbit CD™ serum followed by a secondary anti-rabbit IgG antibody coupled to peroxidase. After revealing, these antibodies were eliminated and the transfer membranes were revealed in the same manner but using an anti-rabbit CD8α serum.

The results are presented in FIGS. 25 and 26.

Comparison of Levels of Expression of Chimeras in Cells and Exosomes:

It was observed that the cell lysates exhibited only weak expression of chimeric proteins. In contrast, the presence of certain chimeric proteins in the exosomes was sometimes very strong.

In addition to the levels of expression, the major difference which was noted between the cell proteins and exosome proteins was the presence of 2 or 3 bands for the cells and only one for the exosomes. This was because the cell contains non-glycosylated forms and forms which are glycosylated to a greater or lesser extent. Only the correctly glycosylated form is found in the exosomes.

Western Blot Analysis of Exosomal Targeting of Positive (CD8α-CD™) and Negative (CD8α Alone) Controls:

With the anti-CD™ serum, a band migrating to 31 kDa was present in the exosomal lysate of the wild type CD8α-CD™ control, while it was absent in the lysate from cells transfected by the negative control. This band is characteristic of the expected chimeric protein.

With the anti-CD8α serum, the negative CD8α control alone had a band near 27 kDa which corresponded to expression and to exosomal targeting of CD8α devoid of CD™. As before, a band migrating to 31 kDa was present in the exosomal lysate of the wild type CD8α-CD™ control. The difference in intensity between the 31 kDa and 27 kDa bands indicates that CD8α is much more targeted onto the exosomes when it is fused to CD™.

Western Blot Analysis of Variations in Targeting of Mutated CD8α-CD™:

Only the results obtained with the anti-CD8α serum were mutually comparable. The results obtained with the anti CD™ serum were only used to confirm the preceding results. As a function of the mutation of the sequence coding for the CD™, these results show a variation in expression and targeting of chimeric proteins to exosomes. This is particularly clear for mutations which strongly inhibit targeting of proteins to exosomes. The mutants concerns were the mutants KM8, KM13, D and KS8.

From these observations it may be concluded that the motif PSAP (KM8 mutant) and the motif DY (at the last motif YxxL (mutants KM13 and D)) are important for exosomal targeting.

b) Quantification of Chimeric Proteins on Exosomes by FACs:

The presence of chimeric proteins was also investigated by a cytofluorometric analysis (FACscan) using a fluorescent monoclonal anti-CD8 antibody.

After fixing exosomes on latex beads (IDC (Interfacial Dynamics Corporation) ultraclean aldehyde/sulphate Latex beads), the chimeric proteins present on the surface of the exosomes were labelled with the aid of a monoclonal mouse anti-CD8α antibody coupled to fluorescein (53-6.7 antibodies from Pharmingen) and analyzed by cytofluorimetry (FACScan).

The results obtained are particularly clear for mutants KM8, KM13 and D, which reveal the importance of mutated amino acids in targeting chimeric proteins on exosomes (see FIGS. 26 and 27). These results confirm the impact of the motifs PSAP, D and Y (in the motif DYxxL) in targeting the proteins to the exosomes already revealed by the Western Blot results.

Conclusion:

During this study, we constructed chimeric genes for expressing the mutated or wild type CD™ pilot peptide fused with mouse CD8α. These mutations of the amino acids or remarkable motifs of CD™ were intended to identify amino acids and consensus motifs that are important in exosome targeting.

The various chimeric genes were integrated into a retroviral expression vector in order to transfect HEK 293T eukaryotic cells in order to obtain expression of these chimeric proteins. The bands observed in Western Blot suggest that, like the native CD8α protein, these proteins are glycosylated differently during their passage through the Golgi apparatus. Only correctly glycosylated proteins were found in the exosomes. These proteins have undergone adequate post translational modifications, a condition which is indispensable to the expression of conformational epitopes essential to the future production of vaccine immunity or to screening therapeutic molecules. However, these glycosylations, which are present to a greater or lesser extent, result in multiple diffuse bands which hindered us during comparative protein quantification. To overcome this problem, the lysates had to be treated with an endoglycosylase in order to observe a single band on the gel.

According to these results, the motifs PSAP and DY (from the last YxxL) are indispensable to expression and targeting of chimeric proteins to exosomes. These results are novel and are interesting both on the fundamental front and on the industrial application front.

It is probable that the PSAP motif is responsible for an interaction with the Tsg101 protein of the ESCRT complex. Regarding the motif DYxxL, it could be implicated in the interaction with the ALIX protein of the ESCRT complex. Thus, for the first time, experimental data suggest that the ESCRT complex is involved in the formation of exosomes.

Example 3

Targeting of Receptors with Transmembrane Domains to Exosomes

Membrane receptors are the major targets for the development of therapeutic molecules. In general, high throughput screening of drugs is carried out, in particular with receptors with multiple membrane domains expressed on cells in culture. In addition to difficulties in obtaining strong expression of receptors on the cell surface, this technique causes difficulties for robotic automation. However, it is currently the only solution since the use of purified recombinant receptors is currently technically unenvisageable.

In this context, exosomes carrying receptors, in particular receptors with multiple domains, would constitute a tool which was simple to use and well suited to screening because of their stability and ease of manipulation.

The present study was aimed as producing exosomes carrying receptors with single or multiple transmembrane domains, in particular the receptor CxCR4 (receptor for the chemokine SDS-1 (CXCL-12) and HIV) and the CD4 receptor (HIV receptor).

Three chimeric chimeric genes were synthesized. They comprised, at the 3' end, the CD™-BLV peptide of sequence SEQ ID NO: 8, and at the 5' end, a DNA coding for the CxCR4 human receptor, for a version of the CxCR4 receptor truncated at the C-terminal part comprising 307 amino acids (CxCR4 (307)) or for a version of the CD4 receptor truncated at the C-terminal part comprising 403 amino acids (CD4 (403)).

The CD4 and CxCR4 receptors respectively comprise one and seven transmembrane domains.

The three chimeric genes were cloned into a retroviral expression vector pLPCX. These various plasmids were transfected into HEK293T human eukaryotic cells in order to observe the expression of the various chimeric proteins in these cells as well as their sorting towards the exosomes.

The cloning and sub-cloning strategy used was similar to that described for Example 2:

The DNAs coding for the receptors CxCR4, CxCR4 (307) and CD4 (403) as well as that coding for the pilot peptide CD™ were amplified by PCR using primers comprising the sequences for the restriction sites which were to be integrated at each end of the amplified fragments (the fragments CxCR4, CxCR4 (307) and CD4 (403) will be flanked at the 5' end by the EcoRI site and at the 3' end by the XbaI site, and CD™/BLV will be flanked at the 5' end by the XbaI site and at the 3' end by the NotI site).

The inserts produced were cloned into the Topo amplification vectors (see FIG. 20). The plasmids obtained were then digested by restriction enzymes and analyzed on 1.5% agarose gel, then sequenced in order to verify the integrity of their sequence.

The CD™/BLV insert was then excised from the Topo vector by enzymatic digestion using the XbaI/NotI couple then sub-cloned into the pKS2 amplification vector (see FIG. 21). The recombinant pKS2 vector as well as the recombinant Topo vectors containing the inserts CxCR4, CxCR4 (307) and CD4 (403) were then digested with the restriction enzymes EcoRI and XbaI, in order to be able to sub-clone the fragments CxCR4, CxCR4 (307) and CD4 (403) into the amplification vector pKS2, said fragments being placed at the 5' end of the sequence coding for the CD™ peptide.

The various constructs thus obtained were excised from the recombinant pKS2 plasmids by digestion with the EcoRI/NotI enzyme pair then sub-cloned into the retroviral expression vector pLPCX (see FIG. 22). The vectors obtained (see FIG. 28) were verified by enzymatic digestion using the EcoRI/XbaI enzyme pair.

The various pLPCX plasmids were transfected into HEK293T human eukaryotic cells in order to express the chimeric proteins CxCR4/CD™, CxCR4(307)/CD™ and CD4 (403)/CD™.

An extract of the total cellular proteins (100 µg) and the proteins of a suspension of exosomes produced by each of the batches of transfected cells then underwent SDS-PAGE (10%) migration in the presence or absence of β-mercaptoethanol. The proteins of interest were revealed by Western Blot using a anti-rabbit CD™ primary serum and anti-rabbit IgG secondary antibody coupled to peroxidase. The antibodies were revealed in a dark room using an ECL solution. Finally, the protein fingerprint of each sample was revealed by staining with Coomassie blue.

The results are presented in FIGS. 29-31.

Note that the chimeras CxCR4/CD™, CxCR4 (307)/CD™ and CD4 (403)/CD™ were expressed in the cellular protein extracts (see FIG. 29).

Several bands characterize the chimera CxCR4/CD™: 36, 42, 62 and 87 kDa. The expression of the wild type CxCR4 receptor is characterized by several isoforms, in particular in the HEK293T cells; the 34, 40, 47, 62, 73 and 80 kDa bands may be identified (Sloane J A, et al.). The larger sizes of the bands of the CxCR4/CD™ chimera in the HEK293T were due to the presence of pilot peptide (CD™ domain) in the CxCR4/CD™ chimera. Similarly, the 30, 42, 60 and 83 kDa bands revealed the presence of the CxCR4 (307)/CD™ chimera. The variation in the size of the bands representing the various isoforms of this chimera is explained by the fact that the CxCR4 receptor is truncated. The CD4 (403)/CD™ chimera is characterized by a clearly visible 53 kDa band.

Further, these chimeras are all sorted to the exosomes, as shown by the presence of 36, 42, 62 and 87 kDa (for CxCR4/CD™) bands; 30, 38, 48, and 83 kDa bands (for CxCR4 (307)/CD™) and the 53 kDa band (for CD4 (403)/CD™) (see FIG. 30).

Revealing the various protein fingerprints with Coomassie blue shows that the total quantities of proteins of exosomal origin (FIG. 31B) used during these experiments are much smaller than the total quantities of proteins of cellular origin (FIG. 31A), while the Western Blot signal is equivalent. It can be seen that all of the proteins present in the control cell lysate are not sorted to the exosomes. The CxCR4/CD™ and CD4(403)/CD™ chimeras are addressed very strongly to the exosomes. In contrast, the CD4 (403)/CD™ chimera is almost completely sorted to the exosomes.

Conclusion

Transfection of HEK293T cells with various pLPCX plasmids has been used to express the chimeras CxCR4/CD™-BLV, CxCR4(403) /CD™-BLV and CD4 (403)/CD™-BLV. Western Blot analysis has demonstrated their presence in the cell lysates.

As expected, several isoforms of the chimeras CxCR4/CD™-BLV and CxCR4 (307)/CD™-BLV are expressed in HEK293T cells transfected with the plasmids pLPCX CxCR4/CD™-BLV and pLPCX CxCR4 (307)/CD™-BLV. The chimeras CxCR4/CD™-BLV and CxCR4 (307)/CD™-BLV are effectively sorted towards the exosomes and it appears that these fusion proteins are equally shared between the cells and the exosomes.

Further, the presence of the chimera CD4 (403)/CD™-BLV is observed in HEK293T cells transfected with the plasmid pLPCX CD4 (403)/CD™-BLV. It appears that the pilot peptide CD™-BLV favours major sorting of the chimera CD4 (403)/CD™-BLV towards the exosomes.

The results described above show that the pilot peptide CD™-BLV is equally capable of sorting proteins with single or with multiple transmembrane domains towards the exosomes.

It is known that it is very difficult to work on these receptors in solution as they are not integrated into a plasma membrane, and they do not retain their native structure. Current studies carried out on these proteins are often made using stable cell lines expressing the receptors of interest. However, this is a constraint in terms of the time and the cost of acquiring, cultivating and maintaining those lines which may die at any time if they are maltreated. For this reason, the fact of using exosomes carrying receptors with multiple transmembrane domains represents an interesting solution as the exosomes have all of the advantages of a cell for these studies with none of the disadvantages since they are not alive.

Exosomes with recombinant proteins integrated into their membrane, and in particular proteins comprising multiple transmembrane domains, could be used in vaccinology and as a screening tool.

REFERENCES

Alberts B, Bray D, Lewis J, Raff M, Roberts K, Watson J D (1995). "Molecular Biology of the Cell (3rd Ed.)" Garland, N.Y.

Cann A J, Churcher M J, Boyd M, O'Brien W, Zhao J O, Zack J, Chen I S (1992). "The region of the envelope gene of human immunodeficiency virus type 1 responsible for determination of cell tropism." J Virol. 1992; 66(1):305-9.

Chaput N, Taïeb J, Schartz N, Andre F, Angevin E, Zitvogel L. (2004). "Exosomes-based immunotherapy." Cancer Immunol Immunother; 53:234-239.

Colino, J. and Snapper C. M. (2006). Journal of Immunology, 177:37576

De Gassart A, Geminard C, Hoekstra D, Vidal M. (2004). "Exosome secretion: the art of reutilizing nonrecycled proteins." Traffic.; 5:896-903.

Delamarre L, Rosenberg A R, Pique C, Pham D, Callebaut I, Dokhelar M C. (1996). "The HTLV-I envelope glycoproteins: structure and functions." J Acquir Immune Defic Syndr Hum Retrovirol; 13 Suppl 1:S85-91.

Delcayre, A., et al. 2005, Blood Cells Mol Dis 35:158; Thery C. et al, (2002); Nature Immunology 3:1156.

Delcayre A, Le Pecq J B. (2006) "Exosomes as novel therapeutic nanodevices." Curr Op in Mol Ther.; 8:1464-1471.

Gould S J, Booth A, Hildret J E. (2003) "The Trojan exosome hypothesis." Proc Natl Acad Sci USA.; 100: 10592-10597.

Herbein G, Coaquette A, Perez-Bercoff D, Pancino G. (2002) "Macrophage activation and HIV infection: can the trojan horse turn into a fortress?" Curr Mol Med.; 2:723-738.

Levine A J. (1992). "Viruses" (Scientific American Library, No. 37). W. H. Freeman/Scientific American Library Pornillos O, Garrus J, Sundquist W I. (2002). "Mechanism of enveloped RNA virus budding." Trends Cell Biol. 2; 12:569-579.

Raposo G, Moore M, Innes D, Leijenderkker R, Leigh-Brown A, Benaroch P, Geuze H. (2002). "Human macrophages accumulate HIV-1 particles in MHC II compartments." Traffic.; 3:718-729.

Sloane J A, et al. (2005). Marked structural and functional heterogeneity in CxCR4: separation of HIV-1 and SDF-1alpha responses. Immunology and Cell Biology; 83: 129-143.

Straub O C, Levy D. (1999). "Bovine immunodeficiency virus and analogies with human immunodeficiency virus." Leukemia.;13 Suppl 1:S106-9.

Zitvogel L, Regnault A, Lozier A, Wolfers J, Tenza D, Raposo G, Amigorena S. (1998). "Dendritic cell-derived exosomes elicit potent antitumour immune responses in vivo." Nat. Med.; 4:594-600.

SEQUENCE LISTING

```
<160> NUMBER OF SEQ ID NOS: 131

<210> SEQ ID NO 1
<211> LENGTH: 81
<212> TYPE: DNA
<213> ORGANISM: Mus musculus
<220> FEATURE:
<221> NAME/KEY: CDS
<222> LOCATION: (1)..(81)
<220> FEATURE:
<221> NAME/KEY: misc_feature
<222> LOCATION: (1)..(81)
<223> OTHER INFORMATION: Signal peptide for importation into the
      endoplasmic reticulum, of the CD8 alpha protein

<400> SEQUENCE: 1 atg gcc tca ccg ttg acc cgc ttt ctg tcg ctg aac ctg ctg ctg ctg      48
Met Ala Ser Pro Leu Thr Arg Phe Leu Ser Leu Asn Leu Leu Leu Leu
1               5                   10                  15 ggt gag tcg att atc ctg ggg agt gga gaa gct                           81
Gly Glu Ser Ile Ile Leu Gly Ser Gly Glu Ala
            20                  25

<210> SEQ ID NO 2
<211> LENGTH: 27
<212> TYPE: PRT
<213> ORGANISM: Mus musculus

<400> SEQUENCE: 2

Met Ala Ser Pro Leu Thr Arg Phe Leu Ser Leu Asn Leu Leu Leu Leu
1               5                   10                  15
```

```
Gly Glu Ser Ile Ile Leu Gly Ser Gly Glu Ala
        20                  25

<210> SEQ ID NO 3
<211> LENGTH: 69
<212> TYPE: DNA
<213> ORGANISM: Bovine leukemia virus
<220> FEATURE:
<221> NAME/KEY: misc_feature
<222> LOCATION: (1)..(69)
<223> OTHER INFORMATION: Transmembrane domain of the TM protein of BLV
      (wild type sequence)
<220> FEATURE:
<221> NAME/KEY: CDS
<222> LOCATION: (1)..(69)

<400> SEQUENCE: 3 ctc att cat tct gtt cta agc cta ttc cta tta gcc ctt ttt ttg ctc     48
Leu Ile His Ser Val Leu Ser Leu Phe Leu Leu Ala Leu Phe Leu Leu
1               5                   10                  15 ttc ttg gcc ccc tgc ctg ata                                         69
Phe Leu Ala Pro Cys Leu Ile
            20

<210> SEQ ID NO 4
<211> LENGTH: 23
<212> TYPE: PRT
<213> ORGANISM: Bovine leukemia virus

<400> SEQUENCE: 4

Leu Ile His Ser Val Leu Ser Leu Phe Leu Leu Ala Leu Phe Leu Leu
1               5                   10                  15

Phe Leu Ala Pro Cys Leu Ile
            20

<210> SEQ ID NO 5
<211> LENGTH: 177
<212> TYPE: DNA
<213> ORGANISM: Bovine leukemia virus
<220> FEATURE:
<221> NAME/KEY: misc_feature
<222> LOCATION: (1)..(177)
<223> OTHER INFORMATION: Wild type cytoplasmic domain (CD) of the TM
      protein
<220> FEATURE:
<221> NAME/KEY: CDS
<222> LOCATION: (1)..(177)
<220> FEATURE:
<221> NAME/KEY: misc_feature
<222> LOCATION: (42)..(42)
<223> OTHER INFORMATION: n = t or a

<400> SEQUENCE: 5 aaa tgc ttg acc tct cgc ctt tta aaa ctc ctc cgg cag gcn ccc cac     48
Lys Cys Leu Thr Ser Arg Leu Leu Lys Leu Leu Arg Gln Ala Pro His
1               5                   10                  15 ttc cct gaa atc tcc ttc ccc cct aaa ccc gat tct gat tat cag gcc     96
Phe Pro Glu Ile Ser Phe Pro Pro Lys Pro Asp Ser Asp Tyr Gln Ala
            20                  25                  30 ttg cta cca tcc gcg cca gag atc tac tct cac ctc tcc ccc acc aaa    144
Leu Leu Pro Ser Ala Pro Glu Ile Tyr Ser His Leu Ser Pro Thr Lys
        35                  40                  45 ccc gat tac atc aac ctt cga ccc tgc ccc tag                        177
Pro Asp Tyr Ile Asn Leu Arg Pro Cys Pro
    50                  55

<210> SEQ ID NO 6
```

```
<211> LENGTH: 58
<212> TYPE: PRT
<213> ORGANISM: Bovine leukemia virus

<400> SEQUENCE: 6

Lys Cys Leu Thr Ser Arg Leu Leu Lys Leu Leu Arg Gln Ala Pro His
1               5                   10                  15

Phe Pro Glu Ile Ser Phe Pro Pro Lys Pro Asp Ser Asp Tyr Gln Ala
            20                  25                  30

Leu Leu Pro Ser Ala Pro Glu Ile Tyr Ser His Leu Ser Pro Thr Lys
        35                  40                  45

Pro Asp Tyr Ile Asn Leu Arg Pro Cys Pro
    50                  55

<210> SEQ ID NO 7
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(135)
<223> OTHER INFORMATION: Mutated derivative of the CD of the TM protein
      of bovine leukaemia virus (BLV): deletion of the 13 N-terminal
      residues
<220> FEATURE:
<221> NAME/KEY: CDS
<222> LOCATION: (1)..(135)

<400> SEQUENCE: 7 gca ccc cac ttc cct gaa atc tcc ttc ccc cct aaa ccc gat tct gat      48
Ala Pro His Phe Pro Glu Ile Ser Phe Pro Pro Lys Pro Asp Ser Asp
1               5                   10                  15 tat cag gcc ttg cta cca tcc gcg cca gag atc tac tct cac ctc tcc      96
Tyr Gln Ala Leu Leu Pro Ser Ala Pro Glu Ile Tyr Ser His Leu Ser
            20                  25                  30 ccc acc aaa ccc gat tac atc aac ctt cga ccc tgc ccc                 135
Pro Thr Lys Pro Asp Tyr Ile Asn Leu Arg Pro Cys Pro
        35                  40                  45

<210> SEQ ID NO 8
<211> LENGTH: 45
<212> TYPE: PRT
<213> ORGANISM: Artificial Sequence
<220> FEATURE:
<223> OTHER INFORMATION: Synthetic Construct

<400> SEQUENCE: 8

Ala Pro His Phe Pro Glu Ile Ser Phe Pro Pro Lys Pro Asp Ser Asp
1               5                   10                  15

Tyr Gln Ala Leu Leu Pro Ser Ala Pro Glu Ile Tyr Ser His Leu Ser
            20                  25                  30

Pro Thr Lys Pro Asp Tyr Ile Asn Leu Arg Pro Cys Pro
        35                  40                  45

<210> SEQ ID NO 9
<211> LENGTH: 174
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(174)
<223> OTHER INFORMATION: Mutated derivative of the CD of the TM protein
``` of BLV: substitution of the C residue of the PCT motif by an A
residue
<220> FEATURE:
<221> NAME/KEY: CDS
<222> LOCATION: (1)..(174)

<400> SEQUENCE: 9

```
aaa tgc ttg acc tct cgc ctt tta aaa ctc ctc cgg cag gca ccc cac      48
Lys Cys Leu Thr Ser Arg Leu Leu Lys Leu Leu Arg Gln Ala Pro His
1               5                   10                  15 ttc cct gaa atc tcc ttc ccc cct aaa ccc gat tct gat tat cag gcc      96
Phe Pro Glu Ile Ser Phe Pro Pro Lys Pro Asp Ser Asp Tyr Gln Ala
                20                  25                  30 ttg cta cca tcc gcg cca gag atc tac tct cac ctc tcc ccc acc aaa     144
Leu Leu Pro Ser Ala Pro Glu Ile Tyr Ser His Leu Ser Pro Thr Lys
            35                  40                  45 ccc gat tac atc aac ctt cga ccg gcg ccc                             174
Pro Asp Tyr Ile Asn Leu Arg Pro Ala Pro
        50                  55
```

<210> SEQ ID NO 10
<211> LENGTH: 58
<212> TYPE: PRT
<213> ORGANISM: Artificial Sequence
<220> FEATURE:
<223> OTHER INFORMATION: Synthetic Construct

<400> SEQUENCE: 10

```
Lys Cys Leu Thr Ser Arg Leu Leu Lys Leu Leu Arg Gln Ala Pro His
1               5                   10                  15

Phe Pro Glu Ile Ser Phe Pro Pro Lys Pro Asp Ser Asp Tyr Gln Ala
                20                  25                  30

Leu Leu Pro Ser Ala Pro Glu Ile Tyr Ser His Leu Ser Pro Thr Lys
            35                  40                  45

Pro Asp Tyr Ile Asn Leu Arg Pro Ala Pro
        50                  55
```

<210> SEQ ID NO 11
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(135)
<220> FEATURE:
<221> NAME/KEY: misc_feature
<222> LOCATION: (1)..(135)
<223> OTHER INFORMATION: Mutated derivative of the CD of the TM protein
of BLV: deletion of the 13 N-terminal residues and substitution of
the C residue of the PCP motif by an A residue

<400> SEQUENCE: 11

```
gca ccc cac ttc cct gaa atc tcc ttc ccc cct aaa ccc gat tct gat      48
Ala Pro His Phe Pro Glu Ile Ser Phe Pro Pro Lys Pro Asp Ser Asp
1               5                   10                  15 tat cag gcc ttg cta cca tcc gcg cca gag atc tac tct cac ctc tcc      96
Tyr Gln Ala Leu Leu Pro Ser Ala Pro Glu Ile Tyr Ser His Leu Ser
                20                  25                  30 ccc acc aaa ccc gat tac atc aac ctt cga ccg gcg ccc                 135
Pro Thr Lys Pro Asp Tyr Ile Asn Leu Arg Pro Ala Pro
            35                  40                  45
```

<210> SEQ ID NO 12

<211> LENGTH: 45
<212> TYPE: PRT
<213> ORGANISM: Artificial Sequence
<220> FEATURE:
<223> OTHER INFORMATION: Synthetic Construct

<400> SEQUENCE: 12

Ala Pro His Phe Pro Glu Ile Ser Phe Pro Pro Lys Pro Asp Ser Asp
1               5                   10                  15

Tyr Gln Ala Leu Leu Pro Ser Ala Pro Glu Ile Tyr Ser His Leu Ser
            20                  25                  30

Pro Thr Lys Pro Asp Tyr Ile Asn Leu Arg Pro Ala Pro
        35                  40                  45

<210> SEQ ID NO 13
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(135)
<220> FEATURE:
<221> NAME/KEY: misc_feature
<222> LOCATION: (1)..(135)
<223> OTHER INFORMATION: Mutated derivative of the CD of the TM protein
      of BLV: deletion of the 13 N-terminal residues and substitution of
      the 2 P residues of the first PxxP motif

<400> SEQUENCE: 13 gca gcc cac ttc gct gag ata tcc ttc ccc cct aaa ccc gat tct gat     48
Ala Ala His Phe Ala Glu Ile Ser Phe Pro Pro Lys Pro Asp Ser Asp
1               5                   10                  15 tat cag gcc ttg cta cca tcc gcg cca gag atc tac tct cac ctc tcc     96
Tyr Gln Ala Leu Leu Pro Ser Ala Pro Glu Ile Tyr Ser His Leu Ser
            20                  25                  30 ccc acc aaa ccc gat tac atc aac ctt cga ccc tgc ccc                135
Pro Thr Lys Pro Asp Tyr Ile Asn Leu Arg Pro Cys Pro
        35                  40                  45

<210> SEQ ID NO 14
<211> LENGTH: 45
<212> TYPE: PRT
<213> ORGANISM: Artificial Sequence
<220> FEATURE:
<223> OTHER INFORMATION: Synthetic Construct

<400> SEQUENCE: 14

Ala Ala His Phe Ala Glu Ile Ser Phe Pro Pro Lys Pro Asp Ser Asp
1               5                   10                  15

Tyr Gln Ala Leu Leu Pro Ser Ala Pro Glu Ile Tyr Ser His Leu Ser
            20                  25                  30

Pro Thr Lys Pro Asp Tyr Ile Asn Leu Arg Pro Cys Pro
        35                  40                  45

<210> SEQ ID NO 15
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(135)
<220> FEATURE:
<221> NAME/KEY: misc_feature
<222> LOCATION: (1)..(135)
<223> OTHER INFORMATION: Mutated derivative of the CD of the TM protein
      of BLV: deletion of the 13 N-terminal residues and substitution of
      the 2 P residues of the second PxxP motif

<400> SEQUENCE: 15 gca ccc cac ttc cct gag ata tcc ttc gcc cct aaa gcc gat tct gat     48
Ala Pro His Phe Pro Glu Ile Ser Phe Ala Pro Lys Ala Asp Ser Asp
1               5                   10                  15 tat cag gcc ttg cta cca tcc gcg cca gag atc tac tct cac ctc tcc     96
Tyr Gln Ala Leu Leu Pro Ser Ala Pro Glu Ile Tyr Ser His Leu Ser
            20                  25                  30 ccc acc aaa ccc gat tac atc aac ctt cga ccc tgc ccc                 135
Pro Thr Lys Pro Asp Tyr Ile Asn Leu Arg Pro Cys Pro
        35                  40                  45

<210> SEQ ID NO 16
<211> LENGTH: 45
<212> TYPE: PRT
<213> ORGANISM: Artificial Sequence
<220> FEATURE:
<223> OTHER INFORMATION: Synthetic Construct

<400> SEQUENCE: 16

Ala Pro His Phe Pro Glu Ile Ser Phe Ala Pro Lys Ala Asp Ser Asp
1               5                   10                  15

Tyr Gln Ala Leu Leu Pro Ser Ala Pro Glu Ile Tyr Ser His Leu Ser
            20                  25                  30

Pro Thr Lys Pro Asp Tyr Ile Asn Leu Arg Pro Cys Pro
        35                  40                  45

<210> SEQ ID NO 17
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(135)
<220> FEATURE:
<221> NAME/KEY: misc_feature
<222> LOCATION: (1)..(135)
<223> OTHER INFORMATION: Mutated derivative of the CD of the TM protein
      of BLV: deletion of the 13 N-terminal residues and substitution of
      the 2 Proline residues of the third PxxP motif

<400> SEQUENCE: 17 gca ccc cac ttc cct gaa atc tcc ttc ccc cct aaa ccc gat tct gat     48
Ala Pro His Phe Pro Glu Ile Ser Phe Pro Pro Lys Pro Asp Ser Asp
1               5                   10                  15 tat cag gcc ttg cta gca tcg gcg gca gag att tac tct cac ctc tcc     96
Tyr Gln Ala Leu Leu Ala Ser Ala Ala Glu Ile Tyr Ser His Leu Ser
            20                  25                  30 ccc acc aaa ccc gat tac atc aac ctt cga ccc tgc ccc                 135
Pro Thr Lys Pro Asp Tyr Ile Asn Leu Arg Pro Cys Pro
        35                  40                  45

<210> SEQ ID NO 18
<211> LENGTH: 45
<212> TYPE: PRT
<213> ORGANISM: Artificial Sequence
<220> FEATURE:
<223> OTHER INFORMATION: Synthetic Construct

<400> SEQUENCE: 18

```
Ala Pro His Phe Pro Glu Ile Ser Phe Pro Lys Pro Asp Ser Asp
1               5                   10                  15

Tyr Gln Ala Leu Leu Ala Ser Ala Ala Glu Ile Tyr Ser His Leu Ser
            20                  25                  30

Pro Thr Lys Pro Asp Tyr Ile Asn Leu Arg Pro Cys Pro
        35                  40                  45
```

<210> SEQ ID NO 19
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(135)
<220> FEATURE:
<221> NAME/KEY: misc_feature
<222> LOCATION: (1)..(135)
<223> OTHER INFORMATION: Mutated derivative of the CD of the TM protein of BLV: deletion of the 13 N-terminal residues and substitution of the 1st P residue of the fourth PxxP motif

<400> SEQUENCE: 19

```
gca ccc cac ttc cct gaa atc tcc ttc ccc cct aaa ccc gat tct gat    48
Ala Pro His Phe Pro Glu Ile Ser Phe Pro Lys Pro Asp Ser Asp
1               5                   10                  15 tat cag gcc ttg cta cca tcc gcg cca gag ata tac tct cac ctc tcc    96
Tyr Gln Ala Leu Leu Pro Ser Ala Pro Glu Ile Tyr Ser His Leu Ser
            20                  25                  30 gcc acc aaa ccc gat tac atc aac ctt cga ccc tgc ccc                135
Ala Thr Lys Pro Asp Tyr Ile Asn Leu Arg Pro Cys Pro
        35                  40                  45
```

<210> SEQ ID NO 20
<211> LENGTH: 45
<212> TYPE: PRT
<213> ORGANISM: Artificial Sequence
<220> FEATURE:
<223> OTHER INFORMATION: Synthetic Construct

<400> SEQUENCE: 20

```
Ala Pro His Phe Pro Glu Ile Ser Phe Pro Lys Pro Asp Ser Asp
1               5                   10                  15

Tyr Gln Ala Leu Leu Pro Ser Ala Pro Glu Ile Tyr Ser His Leu Ser
            20                  25                  30

Ala Thr Lys Pro Asp Tyr Ile Asn Leu Arg Pro Cys Pro
        35                  40                  45
```

<210> SEQ ID NO 21
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(135)
<223> OTHER INFORMATION: Mutated derivative of the CD of the TM protein of BLV: deletion of the 13 N-terminal residues and substitution of the 2 P residues of the fourth PxxP motif
<220> FEATURE:
<221> NAME/KEY: misc_feature
<222> LOCATION: (1)..(135)
<223> OTHER INFORMATION: Mutated derivative of the CD of the TM protein of BLV: deletion of the 13 N-terminal residues and substitution of the fourth C motif of the PCP motif by an A residue of the fourth PxxP motif

<220> FEATURE:
<221> NAME/KEY: CDS
<222> LOCATION: (1)..(135)

<400> SEQUENCE: 21 gca ccc cac ttc cct gaa atc tcc ttc ccc cct aaa ccc gat tct gat    48
Ala Pro His Phe Pro Glu Ile Ser Phe Pro Pro Lys Pro Asp Ser Asp
1               5                   10                  15 tat cag gcc ttg cta cca tcc gcg cca gag ata tac tct cac ctc tcc    96
Tyr Gln Ala Leu Leu Pro Ser Ala Pro Glu Ile Tyr Ser His Leu Ser
            20                  25                  30 gcc acc aaa gcc gat tac atc aac ctt cga ccc tgc ccc                135
Ala Thr Lys Ala Asp Tyr Ile Asn Leu Arg Pro Cys Pro
        35                  40                  45

<210> SEQ ID NO 22
<211> LENGTH: 45
<212> TYPE: PRT
<213> ORGANISM: Artificial Sequence
<220> FEATURE:
<223> OTHER INFORMATION: Synthetic Construct

<400> SEQUENCE: 22

Ala Pro His Phe Pro Glu Ile Ser Phe Pro Pro Lys Pro Asp Ser Asp
1               5                   10                  15

Tyr Gln Ala Leu Leu Pro Ser Ala Pro Glu Ile Tyr Ser His Leu Ser
            20                  25                  30

Ala Thr Lys Ala Asp Tyr Ile Asn Leu Arg Pro Cys Pro
        35                  40                  45

<210> SEQ ID NO 23
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(135)
<220> FEATURE:
<221> NAME/KEY: misc_feature
<222> LOCATION: (1)..(135)
<223> OTHER INFORMATION: Mutated derivative of the CD of the TM protein
      of BLV: deletion of the 13 N-terminal residues and substitution of
      the Y residue of the first YxxL motif

<400> SEQUENCE: 23 gca ccc cac ttc cct gaa atc tcc ttc ccc cct aaa ccc gat tct gat    48
Ala Pro His Phe Pro Glu Ile Ser Phe Pro Pro Lys Pro Asp Ser Asp
1               5                   10                  15 gcg cag gca ttg cta cca tcg gcg cca gag atc tac tct cac ctc tcc    96
Ala Gln Ala Leu Leu Pro Ser Ala Pro Glu Ile Tyr Ser His Leu Ser
            20                  25                  30 ccc acc aaa ccc gat tac atc aac ctt cga ccc tgc ccc                135
Pro Thr Lys Pro Asp Tyr Ile Asn Leu Arg Pro Cys Pro
        35                  40                  45

<210> SEQ ID NO 24
<211> LENGTH: 45
<212> TYPE: PRT
<213> ORGANISM: Artificial Sequence
<220> FEATURE:
<223> OTHER INFORMATION: Synthetic Construct

<400> SEQUENCE: 24

Ala Pro His Phe Pro Glu Ile Ser Phe Pro Pro Lys Pro Asp Ser Asp

```
                1               5                  10                  15
Ala Gln Ala Leu Leu Pro Ser Ala Pro Glu Ile Tyr Ser His Leu Ser
                20                  25                  30

Pro Thr Lys Pro Asp Tyr Ile Asn Leu Arg Pro Cys Pro
        35                  40                  45
```

<210> SEQ ID NO 25
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(135)
<220> FEATURE:
<221> NAME/KEY: misc_feature
<222> LOCATION: (1)..(135)
<223> OTHER INFORMATION: Mutated derivative of the CD of the TM protein
      of BLV: deletion of the 13 N-terminal residues and substitution of
      the Y residue of the second YxxL motif

<400> SEQUENCE: 25

```
gca ccc cac ttc cct gaa atc tcc ttc ccc cct aaa ccc gat tct gat       48
Ala Pro His Phe Pro Glu Ile Ser Phe Pro Pro Lys Pro Asp Ser Asp
1               5                  10                  15 tat cag gcc ttg cta cca tcg gcg cca gag atc gca tct cac ctc tcc       96
Tyr Gln Ala Leu Leu Pro Ser Ala Pro Glu Ile Ala Ser His Leu Ser
                20                  25                  30 ccc acc aaa ccc gat tac atc aac ctt cga ccc tgc ccc                   135
Pro Thr Lys Pro Asp Tyr Ile Asn Leu Arg Pro Cys Pro
        35                  40                  45
```

<210> SEQ ID NO 26
<211> LENGTH: 45
<212> TYPE: PRT
<213> ORGANISM: Artificial Sequence
<220> FEATURE:
<223> OTHER INFORMATION: Synthetic Construct

<400> SEQUENCE: 26

```
Ala Pro His Phe Pro Glu Ile Ser Phe Pro Pro Lys Pro Asp Ser Asp
1               5                  10                  15

Tyr Gln Ala Leu Leu Pro Ser Ala Pro Glu Ile Ala Ser His Leu Ser
                20                  25                  30

Pro Thr Lys Pro Asp Tyr Ile Asn Leu Arg Pro Cys Pro
        35                  40                  45
```

<210> SEQ ID NO 27
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(135)
<220> FEATURE:
<221> NAME/KEY: misc_feature
<222> LOCATION: (1)..(135)
<223> OTHER INFORMATION: Mutated derivative of the CD of the TM protein
      of BLV: substitution of the Y residue of the third YxxL motif

<400> SEQUENCE: 27

```
gca ccc cac ttc cct gaa atc tcc ttc ccc cct aaa ccc gat tct gat       48
Ala Pro His Phe Pro Glu Ile Ser Phe Pro Pro Lys Pro Asp Ser Asp
1               5                  10                  15
```

```
tat cag gcc ttg cta cca tcc gcg cca gag atc tac tct cac ctc tcc      96
Tyr Gln Ala Leu Leu Pro Ser Ala Pro Glu Ile Tyr Ser His Leu Ser
         20                  25                  30 ccc acc aaa ccc gat gcc atc aac ctt agg ccc tgc ccc                 135
Pro Thr Lys Pro Asp Ala Ile Asn Leu Arg Pro Cys Pro
         35                  40              45
```

<210> SEQ ID NO 28
<211> LENGTH: 45
<212> TYPE: PRT
<213> ORGANISM: Artificial Sequence
<220> FEATURE:
<223> OTHER INFORMATION: Synthetic Construct

<400> SEQUENCE: 28

```
Ala Pro His Phe Pro Glu Ile Ser Phe Pro Pro Lys Pro Asp Ser Asp
1               5                   10                  15

Tyr Gln Ala Leu Leu Pro Ser Ala Pro Glu Ile Tyr Ser His Leu Ser
            20                  25                  30

Pro Thr Lys Pro Asp Ala Ile Asn Leu Arg Pro Cys Pro
            35                  40              45
```

<210> SEQ ID NO 29
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(135)
<220> FEATURE:
<221> NAME/KEY: misc_feature
<222> LOCATION: (1)..(135)
<223> OTHER INFORMATION: Mutated derivative of the CD of the TM protein
    of BLV: substitution of the 13 Y N-terminal residues and
    substitution of the S residue before the first YxxL motif
<220> FEATURE:
<221> NAME/KEY: misc_feature
<222> LOCATION: (1)..(135)
<223> OTHER INFORMATION: Mutated derivative of the CD of the TM protein
    of BLV: substitution of the 13 N-terminal residues and
    substitution of the S residue before the first YxxL motif

<400> SEQUENCE: 29

```
gca ccc cac ttc cct gaa atc tcc ttc ccc cct aaa ccc gat gct gat      48
Ala Pro His Phe Pro Glu Ile Ser Phe Pro Pro Lys Pro Asp Ala Asp
1               5                   10                  15 tat cag gcg ttg cta cca tcc gcg cca gag atc tac tct cac ctc tcc      96
Tyr Gln Ala Leu Leu Pro Ser Ala Pro Glu Ile Tyr Ser His Leu Ser
            20                  25                  30 ccc acc aaa ccc gat tac atc aac ctt cga ccc tgc ccc                 135
Pro Thr Lys Pro Asp Tyr Ile Asn Leu Arg Pro Cys Pro
            35                  40              45
```

<210> SEQ ID NO 30
<211> LENGTH: 45
<212> TYPE: PRT
<213> ORGANISM: Artificial Sequence
<220> FEATURE:
<223> OTHER INFORMATION: Synthetic Construct

<400> SEQUENCE: 30

```
Ala Pro His Phe Pro Glu Ile Ser Phe Pro Pro Lys Pro Asp Ala Asp
1               5                   10                  15

Tyr Gln Ala Leu Leu Pro Ser Ala Pro Glu Ile Tyr Ser His Leu Ser
```

```
                        20                  25                  30

Pro Thr Lys Pro Asp Tyr Ile Asn Leu Arg Pro Cys Pro
        35                  40                  45

<210> SEQ ID NO 31
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(135)
<220> FEATURE:
<221> NAME/KEY: misc_feature
<222> LOCATION: (1)..(135)
<223> OTHER INFORMATION: Mutated derivative of the CD of the TM protein
      of BLV: deletion of the 13 N-terminal residues and substitution of
      the E residue before the second YxxL motif

<400> SEQUENCE: 31 gca ccc cac ttc cct gaa atc tcc ttc ccc cct aaa ccc gat tct gat        48
Ala Pro His Phe Pro Glu Ile Ser Phe Pro Pro Lys Pro Asp Ser Asp
1               5                   10                  15 tat cag gcc ttg cta cca tcc gcg cca gcg atc tac tct cac ctc tcc        96
Tyr Gln Ala Leu Leu Pro Ser Ala Pro Ala Ile Tyr Ser His Leu Ser
            20                  25                  30 ccc acc aaa ccc gat tac atc aac ctt cga ccc tgc ccc                   135
Pro Thr Lys Pro Asp Tyr Ile Asn Leu Arg Pro Cys Pro
        35                  40                  45

<210> SEQ ID NO 32
<211> LENGTH: 45
<212> TYPE: PRT
<213> ORGANISM: Artificial Sequence
<220> FEATURE:
<223> OTHER INFORMATION: Synthetic Construct

<400> SEQUENCE: 32

Ala Pro His Phe Pro Glu Ile Ser Phe Pro Pro Lys Pro Asp Ser Asp
1               5                   10                  15

Tyr Gln Ala Leu Leu Pro Ser Ala Pro Ala Ile Tyr Ser His Leu Ser
            20                  25                  30

Pro Thr Lys Pro Asp Tyr Ile Asn Leu Arg Pro Cys Pro
        35                  40                  45

<210> SEQ ID NO 33
<211> LENGTH: 135
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(135)
<220> FEATURE:
<221> NAME/KEY: misc_feature
<222> LOCATION: (1)..(135)
<223> OTHER INFORMATION: Mutated derivative of the CD domain of the TM
      protein of BLV: deletion of the 13 N-terminal residues and
      substitution of the D residue before the 3rd YxxL motif

<400> SEQUENCE: 33 gca ccc cac ttc cct gaa atc tcc ttc ccc cct aaa ccc gat tct gat        48
Ala Pro His Phe Pro Glu Ile Ser Phe Pro Pro Lys Pro Asp Ser Asp
1               5                   10                  15 tat cag gcc ttg cta cca tcc gcg cca gag atc tac tct cac ctc tcc        96
```

```
Tyr Gln Ala Leu Leu Pro Ser Ala Pro Glu Ile Tyr Ser His Leu Ser
            20                  25                  30 ccc acc aag ccg gct tac atc aac ctt cga ccc tgc ccc                      135
Pro Thr Lys Pro Ala Tyr Ile Asn Leu Arg Pro Cys Pro
        35                  40                  45

<210> SEQ ID NO 34
<211> LENGTH: 45
<212> TYPE: PRT
<213> ORGANISM: Artificial Sequence
<220> FEATURE:
<223> OTHER INFORMATION: Synthetic Construct

<400> SEQUENCE: 34

Ala Pro His Phe Pro Glu Ile Ser Phe Pro Pro Lys Pro Asp Ser Asp
1               5                   10                  15

Tyr Gln Ala Leu Leu Pro Ser Ala Pro Glu Ile Tyr Ser His Leu Ser
            20                  25                  30

Pro Thr Lys Pro Ala Tyr Ile Asn Leu Arg Pro Cys Pro
        35                  40                  45

<210> SEQ ID NO 35
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(18)
<220> FEATURE:
<221> NAME/KEY: misc_feature
<222> LOCATION: (1)..(18)
<223> OTHER INFORMATION: Mutated derivative of the CD domain of the TM
      protein of BLV: deletion of the 13 N-terminal residues and of the
      39 C-terminal residues

<400> SEQUENCE: 35 gca ccc cac ttc cct gaa                                                   18
Ala Pro His Phe Pro Glu
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic Construct

<400> SEQUENCE: 36

Ala Pro His Phe Pro Glu
1               5

<210> SEQ ID NO 37
<211> LENGTH: 45
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(45)
<220> FEATURE:
<221> NAME/KEY: misc_feature
<222> LOCATION: (1)..(45)
<223> OTHER INFORMATION: Mutated derivative of the CD domain of the TM
      protein of BLV: deletion of the 13 N-terminal residues and of the
      30 C-terminal residues
```

-continued

```
<400> SEQUENCE: 37 gca ccc cac ttc cct gaa atc tcc ttc ccc cct aaa ccc gat tct      45
Ala Pro His Phe Pro Glu Ile Ser Phe Pro Pro Lys Pro Asp Ser
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Synthetic Construct

<400> SEQUENCE: 38

Ala Pro His Phe Pro Glu Ile Ser Phe Pro Pro Lys Pro Asp Ser
1               5                   10                  15

<210> SEQ ID NO 39
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(63)
<220> FEATURE:
<221> NAME/KEY: misc_feature
<222> LOCATION: (1)..(63)
<223> OTHER INFORMATION: Mutated derivative of the CD domain of the TM
      protein of BLV: deletion of the 13 N-terminal residues and of the
      24 C-terminal residues

<400> SEQUENCE: 39 gca ccc cac ttc cct gaa atc tcc ttc ccc cct aaa ccc gat tct gat     48
Ala Pro His Phe Pro Glu Ile Ser Phe Pro Pro Lys Pro Asp Ser Asp
1               5                   10                  15 tat cag gcc ttg cta                                                 63
Tyr Gln Ala Leu Leu
            20

<210> SEQ ID NO 40
<211> LENGTH: 21
<212> TYPE: PRT
<213> ORGANISM: Artificial Sequence
<220> FEATURE:
<223> OTHER INFORMATION: Synthetic Construct

<400> SEQUENCE: 40

Ala Pro His Phe Pro Glu Ile Ser Phe Pro Pro Lys Pro Asp Ser Asp
1               5                   10                  15

Tyr Gln Ala Leu Leu
            20

<210> SEQ ID NO 41
<211> LENGTH: 78
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(78)
<220> FEATURE:
<221> NAME/KEY: misc_feature
<222> LOCATION: (1)..(78)
<223> OTHER INFORMATION: Mutated derivative of the CD domain of the TM
      protein of BLV: deletion of the 13 N-terminal residues and of the
      19 C-terminal residues
```

<400> SEQUENCE: 41

```
gca ccc cac ttc cct gaa atc tcc ttc ccc cct aaa ccc gat tct gat      48
Ala Pro His Phe Pro Glu Ile Ser Phe Pro Pro Lys Pro Asp Ser Asp
1               5                   10                  15 tat cag gcc ttg cta cca tcc gcg cca gag                              78
Tyr Gln Ala Leu Leu Pro Ser Ala Pro Glu
            20                  25
```

<210> SEQ ID NO 42
<211> LENGTH: 26
<212> TYPE: PRT
<213> ORGANISM: Artificial Sequence
<220> FEATURE:
<223> OTHER INFORMATION: Synthetic Construct

<400> SEQUENCE: 42

```
Ala Pro His Phe Pro Glu Ile Ser Phe Pro Pro Lys Pro Asp Ser Asp
1               5                   10                  15

Tyr Gln Ala Leu Leu Pro Ser Ala Pro Glu
            20                  25
```

<210> SEQ ID NO 43
<211> LENGTH: 93
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(93)
<220> FEATURE:
<221> NAME/KEY: misc_feature
<222> LOCATION: (1)..(93)
<223> OTHER INFORMATION: Mutated derivative of the CD domain of the TM
      protein of BLV: deletion of the 13 N-terminal residues and of the
      14 C-terminal residues

<400> SEQUENCE: 43

```
gca ccc cac ttc cct gaa atc tcc ttc ccc cct aaa ccc gat tct gat      48
Ala Pro His Phe Pro Glu Ile Ser Phe Pro Pro Lys Pro Asp Ser Asp
1               5                   10                  15 tat cag gcc ttg cta cca tcc gcg cca gag atc tac tct cac ctc          93
Tyr Gln Ala Leu Leu Pro Ser Ala Pro Glu Ile Tyr Ser His Leu
            20                  25                  30
```

<210> SEQ ID NO 44
<211> LENGTH: 31
<212> TYPE: PRT
<213> ORGANISM: Artificial Sequence
<220> FEATURE:
<223> OTHER INFORMATION: Synthetic Construct

<400> SEQUENCE: 44

```
Ala Pro His Phe Pro Glu Ile Ser Phe Pro Pro Lys Pro Asp Ser Asp
1               5                   10                  15

Tyr Gln Ala Leu Leu Pro Ser Ala Pro Glu Ile Tyr Ser His Leu
            20                  25                  30
```

<210> SEQ ID NO 45
<211> LENGTH: 111
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(111)

```
<220> FEATURE:
<221> NAME/KEY: misc_feature
<222> LOCATION: (1)..(111)
<223> OTHER INFORMATION: Mutated derivative of the CD domain of the TM
      protein of BLV: deletion of the 13 N-terminal residues and of the
      8 C-terminal residues

<400> SEQUENCE: 45 gca ccc cac ttc cct gaa atc tcc ttc ccc cct aaa ccc gat tct gat      48
Ala Pro His Phe Pro Glu Ile Ser Phe Pro Pro Lys Pro Asp Ser Asp
1               5                   10                  15 tat cag gcc ttg cta cca tcc gcg cca gag atc tac tct cac ctc tcc      96
Tyr Gln Ala Leu Leu Pro Ser Ala Pro Glu Ile Tyr Ser His Leu Ser
            20                  25                  30 ccc acc aaa ccc gat                                                 111
Pro Thr Lys Pro Asp
        35

<210> SEQ ID NO 46
<211> LENGTH: 37
<212> TYPE: PRT
<213> ORGANISM: Artificial Sequence
<220> FEATURE:
<223> OTHER INFORMATION: Synthetic Construct

<400> SEQUENCE: 46

Ala Pro His Phe Pro Glu Ile Ser Phe Pro Pro Lys Pro Asp Ser Asp
1               5                   10                  15

Tyr Gln Ala Leu Leu Pro Ser Ala Pro Glu Ile Tyr Ser His Leu Ser
            20                  25                  30

Pro Thr Lys Pro Asp
        35

<210> SEQ ID NO 47
<211> LENGTH: 123
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(123)
<220> FEATURE:
<221> NAME/KEY: misc_feature
<222> LOCATION: (1)..(123)
<223> OTHER INFORMATION: Mutated derivative of the CD domain of the TM
      protein of BLV: deletion of the 13 N-terminal residues and of the
      4 C-terminal residues

<400> SEQUENCE: 47 gca ccc cac ttc cct gaa atc tcc ttc ccc cct aaa ccc gat tct gat      48
Ala Pro His Phe Pro Glu Ile Ser Phe Pro Pro Lys Pro Asp Ser Asp
1               5                   10                  15 tat cag gcc ttg cta cca tcc gcg cca gag atc tac tct cac ctc tcc      96
Tyr Gln Ala Leu Leu Pro Ser Ala Pro Glu Ile Tyr Ser His Leu Ser
            20                  25                  30 ccc acc aaa ccc gat tac atc aac ctt                                 123
Pro Thr Lys Pro Asp Tyr Ile Asn Leu
        35                  40

<210> SEQ ID NO 48
<211> LENGTH: 41
<212> TYPE: PRT
<213> ORGANISM: Artificial Sequence
<220> FEATURE:
<223> OTHER INFORMATION: Synthetic Construct
```

```
<400> SEQUENCE: 48

Ala Pro His Phe Pro Glu Ile Ser Phe Pro Pro Lys Pro Asp Ser Asp
1               5                   10                  15

Tyr Gln Ala Leu Leu Pro Ser Ala Pro Glu Ile Tyr Ser His Leu Ser
            20                  25                  30

Pro Thr Lys Pro Asp Tyr Ile Asn Leu
            35                  40

<210> SEQ ID NO 49
<211> LENGTH: 25
<212> TYPE: PRT
<213> ORGANISM: Homo sapiens
<220> FEATURE:
<221> NAME/KEY: MISC_FEATURE
<222> LOCATION: (1)..(24)
<223> OTHER INFORMATION: CD4

<400> SEQUENCE: 49

Met Asn Arg Gly Val Pro Phe Arg His Leu Leu Leu Val Leu Gln Leu
1               5                   10                  15

Ala Leu Leu Pro Ala Ala Thr Gln Gly
            20                  25

<210> SEQ ID NO 50
<211> LENGTH: 22
<212> TYPE: PRT
<213> ORGANISM: Mus musculus
<220> FEATURE:
<221> NAME/KEY: MISC_FEATURE
<222> LOCATION: (1)..(22)
<223> OTHER INFORMATION: CD4

<400> SEQUENCE: 50

Met Cys Arg Ala Ile Ser Leu Arg Arg Leu Leu Leu Leu Leu Leu Gln
1               5                   10                  15

Leu Ser Gln Leu Leu Ala
            20

<210> SEQ ID NO 51
<211> LENGTH: 27
<212> TYPE: PRT
<213> ORGANISM: Mus musculus
<220> FEATURE:
<221> NAME/KEY: MISC_FEATURE
<222> LOCATION: (1)..(27)
<223> OTHER INFORMATION: CD8 alpha

<400> SEQUENCE: 51

Met Ala Ser Pro Leu Thr Arg Phe Leu Ser Leu Asn Leu Leu Leu Leu
1               5                   10                  15

Gly Glu Ser Ile Ile Leu Gly Ser Gly Glu Ala
            20                  25

<210> SEQ ID NO 52
<211> LENGTH: 25
<212> TYPE: PRT
<213> ORGANISM: Artificial Sequence
<220> FEATURE:
<223> OTHER INFORMATION: bovine CD8 alpha protein

<400> SEQUENCE: 52

Met Ala Ser Leu Leu Thr Ala Leu Ile Leu Pro Leu Ala Leu Leu Leu
1               5                   10                  15

Leu Asp Ala Ala Lys Val Leu Gly Ser
            20
```

```
                    20                  25

<210> SEQ ID NO 53
<211> LENGTH: 21
<212> TYPE: PRT
<213> ORGANISM: Homo sapiens
<220> FEATURE:
<221> NAME/KEY: MISC_FEATURE
<222> LOCATION: (1)..(21)
<223> OTHER INFORMATION: CD8 alpha

<400> SEQUENCE: 53

Met Ala Leu Pro Val Thr Ala Leu Leu Leu Pro Leu Ala Leu Leu Leu
1               5                   10                  15

His Ala Ala Arg Pro
            20

<210> SEQ ID NO 54
<211> LENGTH: 26
<212> TYPE: PRT
<213> ORGANISM: Rattus norvegicus
<220> FEATURE:
<221> NAME/KEY: MISC_FEATURE
<222> LOCATION: (1)..(26)
<223> OTHER INFORMATION: CD8 alpha

<400> SEQUENCE: 54

Met Ala Leu Pro Val Thr Ala Leu Leu Leu Pro Leu Ala Leu Leu Leu
1               5                   10                  15

His Ala Ala Arg Pro Ser Gln Phe Arg Val
            20                  25

<210> SEQ ID NO 55
<211> LENGTH: 27
<212> TYPE: PRT
<213> ORGANISM: Homo sapiens
<220> FEATURE:
<221> NAME/KEY: MISC_FEATURE
<222> LOCATION: (1)..(27)
<223> OTHER INFORMATION: IL1R1

<400> SEQUENCE: 55

Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu
            20                  25

<210> SEQ ID NO 56
<211> LENGTH: 24
<212> TYPE: PRT
<213> ORGANISM: Homo sapiens
<220> FEATURE:
<221> NAME/KEY: MISC_FEATURE
<222> LOCATION: (1)..(24)
<223> OTHER INFORMATION: EGFR 1, HER 1

<400> SEQUENCE: 56

Met Arg Pro Ser Gly Thr Ala Gly Ala Ala Leu Leu Ala Leu Leu Ala
1               5                   10                  15

Ala Leu Cys Pro Ala Ser Arg Ala
            20

<210> SEQ ID NO 57
<211> LENGTH: 22
<212> TYPE: PRT
<213> ORGANISM: Homo sapiens
```

```
<220> FEATURE:
<221> NAME/KEY: MISC_FEATURE
<222> LOCATION: (1)..(22)
<223> OTHER INFORMATION: HER 2

<400> SEQUENCE: 57

Met Glu Leu Ala Ala Leu Cys Arg Trp Gly Leu Leu Leu Ala Leu Leu
1               5                   10                  15

Pro Pro Gly Ala Ala Ser
            20

<210> SEQ ID NO 58
<211> LENGTH: 19
<212> TYPE: PRT
<213> ORGANISM: Homo sapiens
<220> FEATURE:
<221> NAME/KEY: MISC_FEATURE
<222> LOCATION: (1)..(19)
<223> OTHER INFORMATION: HER 3

<400> SEQUENCE: 58

Met Arg Ala Asn Asp Ala Leu Gln Val Leu Gly Leu Leu Phe Ser Leu
1               5                   10                  15

Ala Arg Gly

<210> SEQ ID NO 59
<211> LENGTH: 25
<212> TYPE: PRT
<213> ORGANISM: Homo sapiens
<220> FEATURE:
<221> NAME/KEY: MISC_FEATURE
<222> LOCATION: (1)..(25)
<223> OTHER INFORMATION: HER 4

<400> SEQUENCE: 59

Met Lys Pro Ala Thr Gly Leu Trp Val Trp Val Ser Leu Leu Val Ala
1               5                   10                  15

Ala Gly Thr Val Gln Pro Ser Asp Ser
            20                  25

<210> SEQ ID NO 60
<211> LENGTH: 20
<212> TYPE: PRT
<213> ORGANISM: Mus musculus
<220> FEATURE:
<221> NAME/KEY: MISC_FEATURE
<222> LOCATION: (1)..(20)
<223> OTHER INFORMATION: IL-2

<400> SEQUENCE: 60

Met Tyr Ser Met Gln Leu Ala Ser Cys Val Thr Leu Thr Leu Val Leu
1               5                   10                  15

Leu Val Asn Ser
            20

<210> SEQ ID NO 61
<211> LENGTH: 24
<212> TYPE: PRT
<213> ORGANISM: Mus musculus
<220> FEATURE:
<221> NAME/KEY: MISC_FEATURE
<222> LOCATION: (1)..(24)
<223> OTHER INFORMATION: IL-6

<400> SEQUENCE: 61

Met Lys Phe Leu Ser Ala Arg Asp Phe His Pro Val Ala Phe Leu Gly
```

```
1               5                   10                  15
Leu Met Leu Val Thr Thr Thr Ala
            20
```

<210> SEQ ID NO 62
<211> LENGTH: 25
<212> TYPE: PRT
<213> ORGANISM: Homo sapiens
<220> FEATURE:
<221> NAME/KEY: MISC_FEATURE
<222> LOCATION: (1)..(25)
<223> OTHER INFORMATION: IL-7

<400> SEQUENCE: 62

```
Met Phe His Val Ser Phe Arg Tyr Ile Phe Gly Leu Pro Pro Leu Ile
1               5                   10                  15

Leu Val Leu Leu Pro Val Ala Ser Ser
            20                  25
```

<210> SEQ ID NO 63
<211> LENGTH: 18
<212> TYPE: PRT
<213> ORGANISM: Mus musculus
<220> FEATURE:
<221> NAME/KEY: MISC_FEATURE
<222> LOCATION: (1)..(18)
<223> OTHER INFORMATION: IL-10

<400> SEQUENCE: 63

```
Met Pro Gly Ser Ala Leu Leu Cys Cys Leu Leu Leu Leu Thr Gly Met
1               5                   10                  15

Arg Ile
```

<210> SEQ ID NO 64
<211> LENGTH: 23
<212> TYPE: PRT
<213> ORGANISM: Homo sapiens
<220> FEATURE:
<221> NAME/KEY: MISC_FEATURE
<222> LOCATION: (1)..(23)
<223> OTHER INFORMATION: MIP-1-alpha chemokine

<400> SEQUENCE: 64

```
Met Gln Val Ser Thr Ala Ala Leu Ala Val Leu Leu Cys Thr Met Ala
1               5                   10                  15

Leu Cys Asn Gln Phe Ser Ala
            20
```

<210> SEQ ID NO 65
<211> LENGTH: 15
<212> TYPE: PRT
<213> ORGANISM: Influenza B virus
<220> FEATURE:
<221> NAME/KEY: MISC_FEATURE
<222> LOCATION: (1)..(15)
<223> OTHER INFORMATION: Haemagglutinin Influenza B virus

<400> SEQUENCE: 65

```
Met Lys Ala Ile Ile Val Leu Leu Met Val Val Thr Ser Asn Ala
1               5                   10                  15
```

<210> SEQ ID NO 66
<211> LENGTH: 16
<212> TYPE: PRT
<213> ORGANISM: Influenza A virus
<220> FEATURE:

```
<221> NAME/KEY: MISC_FEATURE
<222> LOCATION: (1)..(16)
<223> OTHER INFORMATION: Haemagglutinin Influenza A H1N1 virus

<400> SEQUENCE: 66

Met Lys Ala Lys Leu Leu Val Leu Leu Cys Ala Leu Ser Ala Thr Asp
1               5                   10                  15

<210> SEQ ID NO 67
<211> LENGTH: 15
<212> TYPE: PRT
<213> ORGANISM: Influenza A virus
<220> FEATURE:
<221> NAME/KEY: MISC_FEATURE
<222> LOCATION: (1)..(15)
<223> OTHER INFORMATION: Haemagglutinin Influenza A H2N2 virus

<400> SEQUENCE: 67

Met Ala Ile Ile Tyr Leu Ile Leu Leu Phe Thr Ala Val Arg Gly
1               5                   10                  15

<210> SEQ ID NO 68
<211> LENGTH: 16
<212> TYPE: PRT
<213> ORGANISM: Influenza A virus
<220> FEATURE:
<221> NAME/KEY: MISC_FEATURE
<222> LOCATION: (1)..(16)
<223> OTHER INFORMATION: Haemagglutinin Influenza A H3N2 virus

<400> SEQUENCE: 68

Met Lys Thr Ile Ile Ala Leu Ser Tyr Ile Phe Cys Leu Ala Leu Gly
1               5                   10                  15

<210> SEQ ID NO 69
<211> LENGTH: 16
<212> TYPE: PRT
<213> ORGANISM: Influenza A virus
<220> FEATURE:
<221> NAME/KEY: MISC_FEATURE
<222> LOCATION: (1)..(16)
<223> OTHER INFORMATION: Haemagglutinin Influenza A H4N6 virus

<400> SEQUENCE: 69

Met Leu Ser Ile Val Ile Leu Phe Leu Leu Ile Ala Glu Asn Ser Ser
1               5                   10                  15

<210> SEQ ID NO 70
<211> LENGTH: 16
<212> TYPE: PRT
<213> ORGANISM: Influenza A virus
<220> FEATURE:
<221> NAME/KEY: MISC_FEATURE
<222> LOCATION: (1)..(16)
<223> OTHER INFORMATION: Haemagglutinin Influenza A H5N1 virus

<400> SEQUENCE: 70

Met Glu Lys Ile Val Leu Leu Leu Ala Ile Ile Ser Leu Val Lys Ser
1               5                   10                  15

<210> SEQ ID NO 71
<211> LENGTH: 16
<212> TYPE: PRT
<213> ORGANISM: Influenza A virus
<220> FEATURE:
<221> NAME/KEY: MISC_FEATURE
<222> LOCATION: (1)..(16)
<223> OTHER INFORMATION: Haemagglutinin Influenza A H6N5 virus
```

```
<400> SEQUENCE: 71

Met Ile Ala Ile Ile Val Val Ala Ile Leu Ala Thr Ala Gly Arg Ser
1               5                   10                  15

<210> SEQ ID NO 72
<211> LENGTH: 18
<212> TYPE: PRT
<213> ORGANISM: Influenza A virus
<220> FEATURE:
<221> NAME/KEY: MISC_FEATURE
<222> LOCATION: (1)..(18)
<223> OTHER INFORMATION: Haemagglutinin Influenza A H7N7 virus

<400> SEQUENCE: 72

Met Asn Thr Gln Ile Leu Ile Leu Thr Leu Val Ala Ala Ile His Thr
1               5                   10                  15

Asn Ala

<210> SEQ ID NO 73
<211> LENGTH: 16
<212> TYPE: PRT
<213> ORGANISM: Influenza A virus
<220> FEATURE:
<221> NAME/KEY: MISC_FEATURE
<222> LOCATION: (1)..(16)
<223> OTHER INFORMATION: Haemagglutinin Influenza A H8N4 virus

<400> SEQUENCE: 73

Met Glu Lys Phe Ile Ala Ile Ala Thr Leu Ala Ser Thr Asn Ala Tyr
1               5                   10                  15

<210> SEQ ID NO 74
<211> LENGTH: 18
<212> TYPE: PRT
<213> ORGANISM: Influenza A virus
<220> FEATURE:
<221> NAME/KEY: MISC_FEATURE
<222> LOCATION: (1)..(18)
<223> OTHER INFORMATION: Haemagglutinin Influenza A H9N2 virus

<400> SEQUENCE: 74

Met Glu Thr Lys Ala Ile Ile Ala Ala Leu Leu Met Val Thr Ala Ala
1               5                   10                  15

Asn Ala

<210> SEQ ID NO 75
<211> LENGTH: 16
<212> TYPE: PRT
<213> ORGANISM: Influenza A virus
<220> FEATURE:
<221> NAME/KEY: MISC_FEATURE
<222> LOCATION: (1)..(16)
<223> OTHER INFORMATION: Haemagglutinin Influenza A H10N7 virus

<400> SEQUENCE: 75

Met Tyr Lys Val Val Val Ile Ile Ala Leu Leu Gly Ala Val Lys Gly
1               5                   10                  15

<210> SEQ ID NO 76
<211> LENGTH: 16
<212> TYPE: PRT
<213> ORGANISM: Influenza A virus
<220> FEATURE:
<221> NAME/KEY: MISC_FEATURE
<222> LOCATION: (1)..(16)
<223> OTHER INFORMATION: Haemagglutinin Influenza A H11N6 virus
```

<400> SEQUENCE: 76

Met Glu Lys Thr Leu Leu Phe Ala Ala Ile Phe Leu Cys Val Lys Ala
1               5                   10                  15

<210> SEQ ID NO 77
<211> LENGTH: 17
<212> TYPE: PRT
<213> ORGANISM: Influenza A virus
<220> FEATURE:
<221> NAME/KEY: MISC_FEATURE
<222> LOCATION: (1)..(17)
<223> OTHER INFORMATION: Haemagglutinin Influenza A H12N5 virus

<400> SEQUENCE: 77

Met Glu Lys Phe Ile Ile Leu Ser Thr Val Leu Ala Ala Ser Phe Ala
1               5                   10                  15

Tyr

<210> SEQ ID NO 78
<211> LENGTH: 18
<212> TYPE: PRT
<213> ORGANISM: Influenza A virus
<220> FEATURE:
<221> NAME/KEY: MISC_FEATURE
<222> LOCATION: (1)..(18)
<223> OTHER INFORMATION: Haemagglutinin Influenza A H13N6 virus

<400> SEQUENCE: 78

Met Ala Leu Asn Val Ile Ala Thr Leu Thr Leu Ile Ser Val Cys Val
1               5                   10                  15

His Ala

<210> SEQ ID NO 79
<211> LENGTH: 246
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(246)
<223> OTHER INFORMATION: Construct X2
<220> FEATURE:
<221> NAME/KEY: CDS
<222> LOCATION: (1)..(246)

<400> SEQUENCE: 79 ctc att cat tct gtt cta agc cta ttc cta tta gcc ctt ttt ttg ctc    48
Leu Ile His Ser Val Leu Ser Leu Phe Leu Leu Ala Leu Phe Leu Leu
1               5                   10                  15 ttc ttg gcc ccc tgc ctg ata aaa tgc ttg acc tct cgc ctt tta aaa    96
Phe Leu Ala Pro Cys Leu Ile Lys Cys Leu Thr Ser Arg Leu Leu Lys
            20                  25                  30 ctc ctc cgg cag gct ccc cac ttc cct gaa atc tcc ttc ccc cct aaa   144
Leu Leu Arg Gln Ala Pro His Phe Pro Glu Ile Ser Phe Pro Pro Lys
        35                  40                  45 ccc gat tct gat tat cag gcc ttg cta cca tcc gcg cca gag atc tac   192
Pro Asp Ser Asp Tyr Gln Ala Leu Leu Pro Ser Ala Pro Glu Ile Tyr
    50                  55                  60 tct cac ctc tcc ccc acc aaa ccc gat tac atc aac ctt cga ccc tgc   240
Ser His Leu Ser Pro Thr Lys Pro Asp Tyr Ile Asn Leu Arg Pro Cys
65                  70                  75                  80 ccc tag                                                            246
Pro

<210> SEQ ID NO 80
<211> LENGTH: 81
<212> TYPE: PRT
<213> ORGANISM: Artificial Sequence
<220> FEATURE:
<223> OTHER INFORMATION: Synthetic Construct

<400> SEQUENCE: 80

Leu Ile His Ser Val Leu Ser Leu Phe Leu Ala Leu Phe Leu Leu
1               5                   10                  15

Phe Leu Ala Pro Cys Leu Ile Lys Cys Leu Thr Ser Arg Leu Leu Lys
            20                  25                  30

Leu Leu Arg Gln Ala Pro His Phe Pro Glu Ile Ser Phe Pro Pro Lys
        35                  40                  45

Pro Asp Ser Asp Tyr Gln Ala Leu Leu Pro Ser Ala Pro Glu Ile Tyr
    50                  55                  60

Ser His Leu Ser Pro Thr Lys Pro Asp Tyr Ile Asn Leu Arg Pro Cys
65                  70                  75                  80

Pro

<210> SEQ ID NO 81
<211> LENGTH: 246
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(246)
<223> OTHER INFORMATION: Construct X3
<220> FEATURE:
<221> NAME/KEY: CDS
<222> LOCATION: (1)..(246)

<400> SEQUENCE: 81 att tac atc tgg gca ccc ttg gcc gga atc tgc gtg gcc ctt ctg cta      48
Ile Tyr Ile Trp Ala Pro Leu Ala Gly Ile Cys Val Ala Leu Leu Leu
1               5                   10                  15 agc ttg atc ccc tgc ctg ata aaa tgc ctg acc tct cgc ctt tta aaa      96
Ser Leu Ile Pro Cys Leu Ile Lys Cys Leu Thr Ser Arg Leu Leu Lys
            20                  25                  30 ctc ctc cgg cag gct ccc cac ttc cct gaa atc tcc ttc ccc cct aaa     144
Leu Leu Arg Gln Ala Pro His Phe Pro Glu Ile Ser Phe Pro Pro Lys
        35                  40                  45 ccc gat tct gat tat cag gcc ttg cta cca tcc gcg cca gag atc tac     192
Pro Asp Ser Asp Tyr Gln Ala Leu Leu Pro Ser Ala Pro Glu Ile Tyr
    50                  55                  60 tct cac ctc tcc ccc acc aaa ccc gat tac atc aac ctt cga ccc tgc     240
Ser His Leu Ser Pro Thr Lys Pro Asp Tyr Ile Asn Leu Arg Pro Cys
65                  70                  75                  80 ccc tag                                                             246
Pro

<210> SEQ ID NO 82
<211> LENGTH: 81
<212> TYPE: PRT
<213> ORGANISM: Artificial Sequence
<220> FEATURE:
<223> OTHER INFORMATION: Synthetic Construct

<400> SEQUENCE: 82

Ile Tyr Ile Trp Ala Pro Leu Ala Gly Ile Cys Val Ala Leu Leu Leu
1               5                   10                  15

```
Ser Leu Ile Pro Cys Leu Ile Lys Cys Leu Thr Ser Arg Leu Leu Lys
         20                  25                  30

Leu Leu Arg Gln Ala Pro His Phe Pro Glu Ile Ser Phe Pro Pro Lys
         35                  40                  45

Pro Asp Ser Asp Tyr Gln Ala Leu Leu Pro Ser Ala Pro Glu Ile Tyr
     50                  55                  60

Ser His Leu Ser Pro Thr Lys Pro Asp Tyr Ile Asn Leu Arg Pro Cys
 65                  70                  75                  80

Pro
```

<210> SEQ ID NO 83
<211> LENGTH: 225
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(225)
<223> OTHER INFORMATION: Construct X4
<220> FEATURE:
<221> NAME/KEY: CDS
<222> LOCATION: (1)..(225)

<400> SEQUENCE: 83

```
att tac atc tgg gca ccc ttg gcc gga atc tgc gtg gcc ctt ctg ctg      48
Ile Tyr Ile Trp Ala Pro Leu Ala Gly Ile Cys Val Ala Leu Leu Leu
 1               5                  10                  15 tcc ttg atc atc act ctc atc tgc tac cac agg tct aga gct ccc cac      96
Ser Leu Ile Ile Thr Leu Ile Cys Tyr His Arg Ser Arg Ala Pro His
             20                  25                  30 ttc cct gaa atc tcc ttc ccc cct aaa ccc gat tct gat tat cag gcc     144
Phe Pro Glu Ile Ser Phe Pro Pro Lys Pro Asp Ser Asp Tyr Gln Ala
         35                  40                  45 ttg cta cca tcc gcg cca gag atc tac tct cac ctc tcc ccc acc aaa     192
Leu Leu Pro Ser Ala Pro Glu Ile Tyr Ser His Leu Ser Pro Thr Lys
     50                  55                  60 ccc gat tac atc aac ctt cga ccc tgc ccc tag                         225
Pro Asp Tyr Ile Asn Leu Arg Pro Cys Pro
 65                  70
```

<210> SEQ ID NO 84
<211> LENGTH: 74
<212> TYPE: PRT
<213> ORGANISM: Artificial Sequence
<220> FEATURE:
<223> OTHER INFORMATION: Synthetic Construct

<400> SEQUENCE: 84

```
Ile Tyr Ile Trp Ala Pro Leu Ala Gly Ile Cys Val Ala Leu Leu Leu
 1               5                  10                  15

Ser Leu Ile Ile Thr Leu Ile Cys Tyr His Arg Ser Arg Ala Pro His
             20                  25                  30

Phe Pro Glu Ile Ser Phe Pro Pro Lys Pro Asp Ser Asp Tyr Gln Ala
         35                  40                  45

Leu Leu Pro Ser Ala Pro Glu Ile Tyr Ser His Leu Ser Pro Thr Lys
     50                  55                  60

Pro Asp Tyr Ile Asn Leu Arg Pro Cys Pro
 65                  70
```

<210> SEQ ID NO 85

```
<211> LENGTH: 947
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(947)
<223> OTHER INFORMATION: Chimera mouse CD8 alpha protein/CD domain of TM
      of BLV
<220> FEATURE:
<221> NAME/KEY: CDS
<222> LOCATION: (28)..(831)

<400> SEQUENCE: 85
ggatcccttg ctggtggaga gcacacc atg gcc tca ccg ttg acc cgc ttt ctg      54
                               Met Ala Ser Pro Leu Thr Arg Phe Leu
                                 1               5 tcg ctg aac ctg ctg ctg ctg ggt gag tcg att atc ctg ggg agt gga      102
Ser Leu Asn Leu Leu Leu Leu Gly Glu Ser Ile Ile Leu Gly Ser Gly
 10              15                  20                  25 gaa gct aag cca cag gca ccc gaa ctc cga atc ttt cca aag aaa atg      150
Glu Ala Lys Pro Gln Ala Pro Glu Leu Arg Ile Phe Pro Lys Lys Met
                 30                  35                  40 gac gcc gaa ctt ggt cag aag gtg gac ctg gta tgt gaa gtg ttg ggg      198
Asp Ala Glu Leu Gly Gln Lys Val Asp Leu Val Cys Glu Val Leu Gly
             45                  50                  55 tcc gtt tcg caa gga tgc tct tgg ctc ttc cag aac tcc agc tcc aaa      246
Ser Val Ser Gln Gly Cys Ser Trp Leu Phe Gln Asn Ser Ser Ser Lys
         60                  65                  70 ctc ccc cag ccc acc ttc gtt gtc tat atg gct tca tcc cac aac aag      294
Leu Pro Gln Pro Thr Phe Val Val Tyr Met Ala Ser Ser His Asn Lys
     75                  80                  85 ata acg tgg gac gag aag ctg aat tcg tcg aaa ctg ttt tct gcc atg      342
Ile Thr Trp Asp Glu Lys Leu Asn Ser Ser Lys Leu Phe Ser Ala Met
 90                  95                 100                 105 agg gac acg aat aat aag tac gtt ctc acc ctg aac aag ttc agc aag      390
Arg Asp Thr Asn Asn Lys Tyr Val Leu Thr Leu Asn Lys Phe Ser Lys
                110                 115                 120 gaa aac gaa ggc tac tat ttc tgc tca gtc atc agc aac tcg gtg atg      438
Glu Asn Glu Gly Tyr Tyr Phe Cys Ser Val Ile Ser Asn Ser Val Met
            125                 130                 135 tac ttc agt tct gtc gtg cca gtc ctt cag aaa gtg aac tct act act      486
Tyr Phe Ser Ser Val Val Pro Val Leu Gln Lys Val Asn Ser Thr Thr
        140                 145                 150 acc aag cca gtg ctg cga act ccc tca cct gtg cac cct acc ggg aca      534
Thr Lys Pro Val Leu Arg Thr Pro Ser Pro Val His Pro Thr Gly Thr
    155                 160                 165 tct cag ccc cag aga cca gaa gat tgt cgg ccc cgt ggc tca gtg aag      582
Ser Gln Pro Gln Arg Pro Glu Asp Cys Arg Pro Arg Gly Ser Val Lys
170                 175                 180                 185 ggg acc gga ttg gac ttc gcc tgt gat att tac atc tgg gca ccc ttg      630
Gly Thr Gly Leu Asp Phe Ala Cys Asp Ile Tyr Ile Trp Ala Pro Leu
                190                 195                 200 gcc gga atc tgc gtg gcc ctt ctg ctg tcc ttg atc atc act ctc atc      678
Ala Gly Ile Cys Val Ala Leu Leu Leu Ser Leu Ile Ile Thr Leu Ile
            205                 210                 215 tgc tac cac agg tct aga gct ccc cac ttc cct gaa atc tcc ttc ccc      726
Cys Tyr His Arg Ser Arg Ala Pro His Phe Pro Glu Ile Ser Phe Pro
        220                 225                 230 cct aaa ccc gat tct gat tat cag gcc ttg cta cca tcc gcg cca gag      774
Pro Lys Pro Asp Ser Asp Tyr Gln Ala Leu Leu Pro Ser Ala Pro Glu
    235                 240                 245
```

```
atc tac tct cac ctc tcc ccc acc aaa ccc gat tac atc aac ctt cga    822
Ile Tyr Ser His Leu Ser Pro Thr Lys Pro Asp Tyr Ile Asn Leu Arg
250                 255                 260                 265 ccc tgc ccc taggaccccc atgtttcacg caccctcagg ctgtggtggg             871
Pro Cys Pro gcactggctt agtggaatag tcagtgtacc atcacaagcc tcttcttgct gccagcaccg   931
agttcgaagc ggccgc                                                   947
```

```
<210> SEQ ID NO 86
<211> LENGTH: 268
<212> TYPE: PRT
<213> ORGANISM: Artificial Sequence
<220> FEATURE:
<223> OTHER INFORMATION: Synthetic Construct

<400> SEQUENCE: 86
```

| | | | | | | | | | | | | | | |
|---|---|---|---|---|---|---|---|---|---|---|---|---|---|---|
| Met | Ala | Ser | Pro | Leu | Thr | Arg | Phe | Leu | Ser | Leu | Asn | Leu | Leu | Leu |
| 1 | | | | 5 | | | | | 10 | | | | | 15 |

Gly Glu Ser Ile Ile Leu Gly Ser Glu Ala Lys Pro Gln Ala Pro
             20                  25                  30

Glu Leu Arg Ile Phe Pro Lys Lys Met Asp Ala Glu Leu Gly Gln Lys
         35                  40                  45

Val Asp Leu Val Cys Glu Val Leu Gly Ser Val Ser Gln Gly Cys Ser
50                  55                  60

Trp Leu Phe Gln Asn Ser Ser Lys Leu Pro Gln Pro Thr Phe Val
65                  70                  75                  80

Val Tyr Met Ala Ser Ser His Asn Lys Ile Thr Trp Asp Glu Lys Leu
                 85                  90                  95

Asn Ser Ser Lys Leu Phe Ser Ala Met Arg Asp Thr Asn Asn Lys Tyr
             100                 105                 110

Val Leu Thr Leu Asn Lys Phe Ser Lys Glu Asn Glu Gly Tyr Tyr Phe
             115                 120                 125

Cys Ser Val Ile Ser Asn Ser Val Met Tyr Phe Ser Ser Val Val Pro
         130                 135                 140

Val Leu Gln Lys Val Asn Ser Thr Thr Thr Lys Pro Val Leu Arg Thr
145                 150                 155                 160

Pro Ser Pro Val His Pro Thr Gly Thr Ser Gln Pro Gln Arg Pro Glu
                 165                 170                 175

Asp Cys Arg Pro Arg Gly Ser Val Lys Gly Thr Gly Leu Asp Phe Ala
             180                 185                 190

Cys Asp Ile Tyr Ile Trp Ala Pro Leu Ala Gly Ile Cys Val Ala Leu
         195                 200                 205

Leu Leu Ser Leu Ile Ile Thr Leu Ile Cys Tyr His Arg Ser Arg Ala
    210                 215                 220

Pro His Phe Pro Glu Ile Ser Phe Pro Pro Lys Pro Asp Ser Asp Tyr
225                 230                 235                 240

Gln Ala Leu Leu Pro Ser Ala Pro Glu Ile Tyr Ser His Leu Ser Pro
                 245                 250                 255

Thr Lys Pro Asp Tyr Ile Asn Leu Arg Pro Cys Pro
             260                 265

```
<210> SEQ ID NO 87
<211> LENGTH: 12
<212> TYPE: DNA
<213> ORGANISM: Artificial Sequence
<220> FEATURE:
```

```
<223> OTHER INFORMATION: Synthetic oligonucleotide
<220> FEATURE:
<221> NAME/KEY: CDS
<222> LOCATION: (1)..(12)

<400> SEQUENCE: 87 cca tcc gcg cca                                                          12
Pro Ser Ala Pro
1

<210> SEQ ID NO 88
<211> LENGTH: 4
<212> TYPE: PRT
<213> ORGANISM: Artificial Sequence
<220> FEATURE:
<223> OTHER INFORMATION: Synthetic Construct

<400> SEQUENCE: 88

Pro Ser Ala Pro
1

<210> SEQ ID NO 89
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 89

Pro Thr Ala Pro
1

<210> SEQ ID NO 90
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: CDS
<222> LOCATION: (1)..(12)

<400> SEQUENCE: 90 tac atc aac ctt                                                          12
Tyr Ile Asn Leu
1

<210> SEQ ID NO 91
<211> LENGTH: 4
<212> TYPE: PRT
<213> ORGANISM: Artificial Sequence
<220> FEATURE:
<223> OTHER INFORMATION: Synthetic Construct

<400> SEQUENCE: 91

Tyr Ile Asn Leu
1

<210> SEQ ID NO 92
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: CDS
<222> LOCATION: (1)..(15)

<400> SEQUENCE: 92
```

```
gat tac atc aac ctt                                          15
Asp Tyr Ile Asn Leu
1               5

<210> SEQ ID NO 93
<211> LENGTH: 5
<212> TYPE: PRT
<213> ORGANISM: Artificial Sequence
<220> FEATURE:
<223> OTHER INFORMATION: Synthetic Construct

<400> SEQUENCE: 93

Asp Tyr Ile Asn Leu
1               5

<210> SEQ ID NO 94
<211> LENGTH: 60
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: CDS
<222> LOCATION: (1)..(60)
<220> FEATURE:
<221> NAME/KEY: misc_feature
<222> LOCATION: (1)..(60)
<223> OTHER INFORMATION: Mutated derivative of the CD of the TM protein
      of BLV

<400> SEQUENCE: 94 cca tcc gcg cca gag atc tac tct cac ctc tcc ccc acc aaa ccc gat    48
Pro Ser Ala Pro Glu Ile Tyr Ser His Leu Ser Pro Thr Lys Pro Asp
1               5                   10                  15 tac atc aac ctt                                              60
Tyr Ile Asn Leu
            20

<210> SEQ ID NO 95
<211> LENGTH: 20
<212> TYPE: PRT
<213> ORGANISM: Artificial Sequence
<220> FEATURE:
<223> OTHER INFORMATION: Synthetic Construct

<400> SEQUENCE: 95

Pro Ser Ala Pro Glu Ile Tyr Ser His Leu Ser Pro Thr Lys Pro Asp
1               5                   10                  15

Tyr Ile Asn Leu
            20

<210> SEQ ID NO 96
<211> LENGTH: 12
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(12)

<400> SEQUENCE: 96 tac tct cac ctc                                              12
Tyr Ser His Leu
1

<210> SEQ ID NO 97
```

```
<211> LENGTH: 4
<212> TYPE: PRT
<213> ORGANISM: Artificial Sequence
<220> FEATURE:
<223> OTHER INFORMATION: Synthetic Construct

<400> SEQUENCE: 97

Tyr Ser His Leu
1

<210> SEQ ID NO 98
<211> LENGTH: 40
<212> TYPE: DNA
<213> ORGANISM: Artificial Sequence
<220> FEATURE:
<223> OTHER INFORMATION: Primer S to A, sense

<400> SEQUENCE: 98
ccctaaaccc gatgctgatt atcaggcgtt gctaccatcc                              40

<210> SEQ ID NO 99
<211> LENGTH: 40
<212> TYPE: DNA
<213> ORGANISM: Artificial Sequence
<220> FEATURE:
<223> OTHER INFORMATION: Primer S to A, anti-sense

<400> SEQUENCE: 99
cgcggatggt agcaacgcct gataatcagc atcgggttta                              40

<210> SEQ ID NO 100
<211> LENGTH: 25
<212> TYPE: DNA
<213> ORGANISM: Artificial Sequence
<220> FEATURE:
<223> OTHER INFORMATION: Primer D to A, sense

<400> SEQUENCE: 100
ccaccaagcc ggcatacatc aacct                                              25

<210> SEQ ID NO 101
<211> LENGTH: 27
<212> TYPE: DNA
<213> ORGANISM: Artificial Sequence
<220> FEATURE:
<223> OTHER INFORMATION: Primer D to A, anti-sense

<400> SEQUENCE: 101
tcgaaggttg atgtatgccg gcttggt                                            27

<210> SEQ ID NO 102
<211> LENGTH: 25
<212> TYPE: DNA
<213> ORGANISM: Artificial Sequence
<220> FEATURE:
<223> OTHER INFORMATION: Primer E to A, sense

<400> SEQUENCE: 102
gctaccatcc gcgccagcga tctac                                              25

<210> SEQ ID NO 103
<211> LENGTH: 23
<212> TYPE: DNA
<213> ORGANISM: Artificial Sequence
<220> FEATURE:
<223> OTHER INFORMATION: Primer E to A, anti-sense
```

-continued

```
<400> SEQUENCE: 103
gtagatcgct ggcgcggatg gta                                             23

<210> SEQ ID NO 104
<211> LENGTH: 20
<212> TYPE: PRT
<213> ORGANISM: Artificial Sequence
<220> FEATURE:
<223> OTHER INFORMATION: mutated derivative of CD domain
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (5)..(16)
<223> OTHER INFORMATION: Xaa can be any amino acid
<220> FEATURE:
<221> NAME/KEY: misc_feature
<222> LOCATION: (18)..(19)
<223> OTHER INFORMATION: Xaa can be any amino acid

<400> SEQUENCE: 104

Pro Xaa Xaa Pro Xaa Xaa Xaa Xaa Xaa Xaa Xaa Xaa Xaa Xaa Xaa
1               5                   10                  15

Tyr Xaa Xaa Leu
            20

<210> SEQ ID NO 105
<211> LENGTH: 20
<212> TYPE: PRT
<213> ORGANISM: Artificial Sequence
<220> FEATURE:
<223> OTHER INFORMATION: mutated derivative of CD domain
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (5)..(15)
<223> OTHER INFORMATION: Xaa can be any amino acid
<220> FEATURE:
<221> NAME/KEY: misc_feature
<222> LOCATION: (18)..(19)
<223> OTHER INFORMATION: Xaa can be any amino acid

<400> SEQUENCE: 105

Pro Xaa Xaa Pro Xaa Xaa Xaa Xaa Xaa Xaa Xaa Xaa Xaa Xaa Asp
1               5                   10                  15

Tyr Xaa Xaa Leu
            20

<210> SEQ ID NO 106
<211> LENGTH: 20
<212> TYPE: PRT
<213> ORGANISM: Artificial Sequence
<220> FEATURE:
<223> OTHER INFORMATION: mutated derivative of CD domain
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (5)..(6)
<223> OTHER INFORMATION: Xaa can be any amino acid
<220> FEATURE:
<221> NAME/KEY: misc_feature
<222> LOCATION: (8)..(16)
<223> OTHER INFORMATION: Xaa can be any amino acid
```

```
<220> FEATURE:
<221> NAME/KEY: misc_feature
<222> LOCATION: (18)..(19)
<223> OTHER INFORMATION: Xaa can be any amino acid

<400> SEQUENCE: 106

Pro Xaa Xaa Pro Xaa Xaa Tyr Xaa Xaa Xaa Xaa Xaa Xaa Xaa Xaa
1               5                   10                  15

Tyr Xaa Xaa Leu
            20

<210> SEQ ID NO 107
<211> LENGTH: 20
<212> TYPE: PRT
<213> ORGANISM: Artificial Sequence
<220> FEATURE:
<223> OTHER INFORMATION: mutated derivative of CD domain
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (5)..(6)
<223> OTHER INFORMATION: Xaa can be any amino acid
<220> FEATURE:
<221> NAME/KEY: misc_feature
<222> LOCATION: (8)..(15)
<223> OTHER INFORMATION: Xaa can be any amino acid
<220> FEATURE:
<221> NAME/KEY: misc_feature
<222> LOCATION: (18)..(19)
<223> OTHER INFORMATION: Xaa can be any amino acid

<400> SEQUENCE: 107

Pro Xaa Xaa Pro Xaa Xaa Tyr Xaa Xaa Xaa Xaa Xaa Xaa Xaa Asp
1               5                   10                  15

Tyr Xaa Xaa Leu
            20

<210> SEQ ID NO 108
<211> LENGTH: 20
<212> TYPE: PRT
<213> ORGANISM: Artificial Sequence
<220> FEATURE:
<223> OTHER INFORMATION: mutated derivative of CD domain
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (6)..(6)
<223> OTHER INFORMATION: Xaa can be any amino acid
<220> FEATURE:
<221> NAME/KEY: misc_feature
<222> LOCATION: (8)..(9)
<223> OTHER INFORMATION: Xaa can be any amino acid
<220> FEATURE:
<221> NAME/KEY: misc_feature
<222> LOCATION: (11)..(11)
<223> OTHER INFORMATION: Xaa can be any amino acid
<220> FEATURE:
<221> NAME/KEY: misc_feature
<222> LOCATION: (13)..(14)
<223> OTHER INFORMATION: Xaa can be any amino acid
<220> FEATURE:
<221> NAME/KEY: misc_feature
<222> LOCATION: (18)..(19)
<223> OTHER INFORMATION: Xaa can be any amino acid

<400> SEQUENCE: 108
```

Pro Xaa Xaa Pro Glu Xaa Tyr Xaa Xaa Leu Xaa Pro Xaa Xaa Pro Asp
1               5                   10                  15

Tyr Xaa Xaa Leu
            20

<210> SEQ ID NO 109
<211> LENGTH: 57
<212> TYPE: PRT
<213> ORGANISM: Artificial Sequence
<220> FEATURE:
<223> OTHER INFORMATION: mutated derivative of CD domain
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (5)..(53)
<223> OTHER INFORMATION: Xaa, if present, can be any amino acid
<220> FEATURE:
<221> NAME/KEY: misc_feature
<222> LOCATION: (55)..(56)
<223> OTHER INFORMATION: Xaa can be any amino acid

<400> SEQUENCE: 109

Pro Xaa Xaa Pro Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Tyr Xaa Xaa Leu
    50                  55

<210> SEQ ID NO 110
<211> LENGTH: 58
<212> TYPE: PRT
<213> ORGANISM: Artificial Sequence
<220> FEATURE:
<223> OTHER INFORMATION: mutated derivative of CD domain
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (5)..(53)
<223> OTHER INFORMATION: Xaa, if present, can be any amino acid
<220> FEATURE:
<221> NAME/KEY: misc_feature
<222> LOCATION: (56)..(57)
<223> OTHER INFORMATION: Xaa can be any amino acid

<400> SEQUENCE: 110

Pro Xaa Xaa Pro Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Asp Tyr Xaa Xaa Leu
    50                  55

<210> SEQ ID NO 111
<211> LENGTH: 107
<212> TYPE: PRT
<213> ORGANISM: Artificial Sequence

```
<220> FEATURE:
<223> OTHER INFORMATION: mutated derivative of CD domain
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (5)..(53)
<223> OTHER INFORMATION: Xaa, if present, can be any amino acid
<220> FEATURE:
<221> NAME/KEY: misc_feature
<222> LOCATION: (55)..(103)
<223> OTHER INFORMATION: Xaa, if present, can be any amino acid
<220> FEATURE:
<221> NAME/KEY: misc_feature
<222> LOCATION: (105)..(106)
<223> OTHER INFORMATION: Xaa can be any amino acid

<400> SEQUENCE: 111

Pro Xaa Xaa Pro Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Tyr Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa
             85                  90                  95

Xaa Xaa Xaa Xaa Xaa Xaa Xaa Tyr Xaa Xaa Leu
            100                 105

<210> SEQ ID NO 112
<211> LENGTH: 108
<212> TYPE: PRT
<213> ORGANISM: Artificial Sequence
<220> FEATURE:
<223> OTHER INFORMATION: mutated derivative of CD domain
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (5)..(53)
<223> OTHER INFORMATION: Xaa, if present, can be any amino acid
<220> FEATURE:
<221> NAME/KEY: misc_feature
<222> LOCATION: (55)..(103)
<223> OTHER INFORMATION: Xaa, if present, can be any amino acid
<220> FEATURE:
<221> NAME/KEY: misc_feature
<222> LOCATION: (106)..(107)
<223> OTHER INFORMATION: Xaa can be any amino acid

<400> SEQUENCE: 112

Pro Xaa Xaa Pro Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Tyr Xaa Xaa Xaa Xaa Xaa Xaa Xaa Xaa Xaa
     50                  55                  60
```

```
Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Asp Tyr Xaa Xaa Leu
        100                 105

<210> SEQ ID NO 113
<211> LENGTH: 116
<212> TYPE: PRT
<213> ORGANISM: Artificial Sequence
<220> FEATURE:
<223> OTHER INFORMATION: mutated derivative of CD domain
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (6)..(54)
<223> OTHER INFORMATION: Xaa, if present, can be any amino acid
<220> FEATURE:
<221> NAME/KEY: misc_feature
<222> LOCATION: (56)..(57)
<223> OTHER INFORMATION: Xaa can be any amino acid
<220> FEATURE:
<221> NAME/KEY: misc_feature
<222> LOCATION: (59)..(107)
<223> OTHER INFORMATION: Xaa, if present, can be any amino acid
<220> FEATURE:
<221> NAME/KEY: misc_feature
<222> LOCATION: (109)..(110)
<223> OTHER INFORMATION: Xaa can be any amino acid
<220> FEATURE:
<221> NAME/KEY: misc_feature
<222> LOCATION: (114)..(115)
<223> OTHER INFORMATION: Xaa can be any amino acid

<400> SEQUENCE: 113

Pro Xaa Xaa Pro Glu Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Tyr Xaa Xaa Leu Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Pro Xaa Xaa Pro Asp
            100                 105                 110

Tyr Xaa Xaa Leu
        115

<210> SEQ ID NO 114
<211> LENGTH: 40
<212> TYPE: PRT
<213> ORGANISM: Artificial Sequence
<220> FEATURE:
<223> OTHER INFORMATION: mutated derivative of CD domain
<220> FEATURE:
<221> NAME/KEY: misc_feature
<222> LOCATION: (2)..(3)
<223> OTHER INFORMATION: Xaa can be any amino acid
```

```
<220> FEATURE:
<221> NAME/KEY: misc_feature
<222> LOCATION: (5)..(8)
<223> OTHER INFORMATION: Xaa can be any amino acid
<220> FEATURE:
<221> NAME/KEY: misc_feature
<222> LOCATION: (10)..(11)
<223> OTHER INFORMATION: Xaa can be any amino acid
<220> FEATURE:
<221> NAME/KEY: misc_feature
<222> LOCATION: (13)..(15)
<223> OTHER INFORMATION: Xaa can be any amino acid
<220> FEATURE:
<221> NAME/KEY: misc_feature
<222> LOCATION: (17)..(18)
<223> OTHER INFORMATION: Xaa can be any amino acid
<220> FEATURE:
<221> NAME/KEY: misc_feature
<222> LOCATION: (20)..(20)
<223> OTHER INFORMATION: Xaa can be any amino acid
<220> FEATURE:
<221> NAME/KEY: misc_feature
<222> LOCATION: (22)..(23)
<223> OTHER INFORMATION: Xaa can be any amino acid
<220> FEATURE:
<221> NAME/KEY: misc_feature
<222> LOCATION: (26)..(26)
<223> OTHER INFORMATION: Xaa can be any amino acid
<220> FEATURE:
<221> NAME/KEY: misc_feature
<222> LOCATION: (28)..(29)
<223> OTHER INFORMATION: Xaa can be any amino acid
<220> FEATURE:
<221> NAME/KEY: misc_feature
<222> LOCATION: (31)..(31)
<223> OTHER INFORMATION: Xaa can be any amino acid
<220> FEATURE:
<221> NAME/KEY: misc_feature
<222> LOCATION: (33)..(34)
<223> OTHER INFORMATION: Xaa can be any amino acid
<220> FEATURE:
<221> NAME/KEY: misc_feature
<222> LOCATION: (38)..(39)
<223> OTHER INFORMATION: Xaa can be any amino acid

<400> SEQUENCE: 114

Pro Xaa Xaa Pro Xaa Xaa Xaa Xaa Pro Xaa Xaa Pro Xaa Xaa Xaa Tyr
1               5                   10                  15

Xaa Xaa Leu Xaa Pro Xaa Xaa Pro Glu Xaa Tyr Xaa Xaa Leu Xaa Pro
            20                  25                  30

Xaa Xaa Pro Asp Tyr Xaa Xaa Leu
        35                  40

<210> SEQ ID NO 115
<211> LENGTH: 275
<212> TYPE: PRT
<213> ORGANISM: Artificial Sequence
<220> FEATURE:
<223> OTHER INFORMATION: mutated derivative of CD domain
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (5)..(53)
<223> OTHER INFORMATION: Xaa, if present, can be any amino acid
<220> FEATURE:
<221> NAME/KEY: misc_feature
<222> LOCATION: (55)..(56)
<223> OTHER INFORMATION: Xaa can be any amino acid
<220> FEATURE:
<221> NAME/KEY: misc_feature
<222> LOCATION: (58)..(106)
<223> OTHER INFORMATION: Xaa, if present, can be any amino acid
```

```
<220> FEATURE:
<221> NAME/KEY: misc_feature
<222> LOCATION: (108)..(109)
<223> OTHER INFORMATION: Xaa can be any amino acid
<220> FEATURE:
<221> NAME/KEY: misc_feature
<222> LOCATION: (111)..(159)
<223> OTHER INFORMATION: Xaa, if present, can be any amino acid
<220> FEATURE:
<221> NAME/KEY: misc_feature
<222> LOCATION: (161)..(162)
<223> OTHER INFORMATION: Xaa can be any amino acid
<220> FEATURE:
<221> NAME/KEY: misc_feature
<222> LOCATION: (165)..(213)
<223> OTHER INFORMATION: Xaa, if present, can be any amino acid
<220> FEATURE:
<221> NAME/KEY: misc_feature
<222> LOCATION: (215)..(216)
<223> OTHER INFORMATION: Xaa can be any amino acid
<220> FEATURE:
<221> NAME/KEY: misc_feature
<222> LOCATION: (218)..(266)
<223> OTHER INFORMATION: Xaa, if present, can be any amino acid
<220> FEATURE:
<221> NAME/KEY: misc_feature
<222> LOCATION: (268)..(269)
<223> OTHER INFORMATION: Xaa can be any amino acid
<220> FEATURE:
<221> NAME/KEY: misc_feature
<222> LOCATION: (273)..(274)
<223> OTHER INFORMATION: Xaa can be any amino acid

<400> SEQUENCE: 115

Pro Xaa Xaa Pro Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Pro Xaa Xaa Pro Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Tyr Xaa Xaa Leu Xaa Xaa
            100                 105                 110

Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa Xaa
            130                 135                 140

Xaa Xaa Xaa Xaa Xaa Xaa Xaa Xaa Xaa Xaa Xaa Xaa Xaa Xaa Pro
145                 150                 155                 160

Xaa Xaa Pro Glu Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
            195                 200                 205

Xaa Xaa Xaa Xaa Xaa Tyr Xaa Xaa Leu Xaa Xaa Xaa Xaa Xaa Xaa
            210                 215                 220

Xaa Xaa Xaa Xaa Xaa Xaa Xaa Xaa Xaa Xaa Xaa Xaa Xaa Xaa Xaa
225                 230                 235                 240
```

```
Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Pro Xaa Xaa Pro Asp Tyr
        260                 265                 270

Xaa Xaa Leu
    275

<210> SEQ ID NO 116
<211> LENGTH: 44
<212> TYPE: PRT
<213> ORGANISM: Artificial Sequence
<220> FEATURE:
<223> OTHER INFORMATION: mutated derivative of CD domain
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (5)..(8)
<223> OTHER INFORMATION: Xaa can be any amino acid
<220> FEATURE:
<221> NAME/KEY: misc_feature
<222> LOCATION: (10)..(11)
<223> OTHER INFORMATION: Xaa can be any amino acid
<220> FEATURE:
<221> NAME/KEY: misc_feature
<222> LOCATION: (13)..(15)
<223> OTHER INFORMATION: Xaa can be any amino acid
<220> FEATURE:
<221> NAME/KEY: misc_feature
<222> LOCATION: (17)..(18)
<223> OTHER INFORMATION: Xaa can be any amino acid
<220> FEATURE:
<221> NAME/KEY: misc_feature
<222> LOCATION: (20)..(20)
<223> OTHER INFORMATION: Xaa can be any amino acid
<220> FEATURE:
<221> NAME/KEY: misc_feature
<222> LOCATION: (22)..(23)
<223> OTHER INFORMATION: Xaa can be any amino acid
<220> FEATURE:
<221> NAME/KEY: misc_feature
<222> LOCATION: (26)..(26)
<223> OTHER INFORMATION: Xaa can be any amino acid
<220> FEATURE:
<221> NAME/KEY: misc_feature
<222> LOCATION: (28)..(29)
<223> OTHER INFORMATION: Xaa can be any amino acid
<220> FEATURE:
<221> NAME/KEY: misc_feature
<222> LOCATION: (31)..(31)
<223> OTHER INFORMATION: Xaa can be any amino acid
<220> FEATURE:
<221> NAME/KEY: misc_feature
<222> LOCATION: (33)..(34)
<223> OTHER INFORMATION: Xaa can be any amino acid
<220> FEATURE:
<221> NAME/KEY: misc_feature
<222> LOCATION: (38)..(39)
<223> OTHER INFORMATION: Xaa can be any amino acid
<220> FEATURE:
<221> NAME/KEY: misc_feature
<222> LOCATION: (41)..(44)
<223> OTHER INFORMATION: Xaa can be any amino acid

<400> SEQUENCE: 116

Pro Xaa Xaa Pro Xaa Xaa Xaa Xaa Pro Xaa Xaa Pro Xaa Xaa Xaa Tyr
1               5                   10                  15

Xaa Xaa Leu Xaa Pro Xaa Xaa Pro Glu Xaa Tyr Xaa Xaa Leu Xaa Pro
            20                  25                  30

Xaa Xaa Pro Asp Tyr Xaa Xaa Leu Xaa Xaa Xaa Xaa
```

-continued

<210> SEQ ID NO 117
<211> LENGTH: 279
<212> TYPE: PRT
<213> ORGANISM: Artificial Sequence
<220> FEATURE:
<223> OTHER INFORMATION: mutated derivative of CD domain
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (5)..(53)
<223> OTHER INFORMATION: Xaa, if present, can be any amino acid
<220> FEATURE:
<221> NAME/KEY: misc_feature
<222> LOCATION: (55)..(56)
<223> OTHER INFORMATION: Xaa can be any amino acid
<220> FEATURE:
<221> NAME/KEY: misc_feature
<222> LOCATION: (58)..(106)
<223> OTHER INFORMATION: Xaa, if present, can be any amino acid
<220> FEATURE:
<221> NAME/KEY: misc_feature
<222> LOCATION: (108)..(109)
<223> OTHER INFORMATION: Xaa can be any amino acid
<220> FEATURE:
<221> NAME/KEY: misc_feature
<222> LOCATION: (111)..(159)
<223> OTHER INFORMATION: Xaa, if present, can be any amino acid
<220> FEATURE:
<221> NAME/KEY: misc_feature
<222> LOCATION: (161)..(162)
<223> OTHER INFORMATION: Xaa can be any amino acid
<220> FEATURE:
<221> NAME/KEY: misc_feature
<222> LOCATION: (165)..(213)
<223> OTHER INFORMATION: Xaa, if present, can be any amino acid
<220> FEATURE:
<221> NAME/KEY: misc_feature
<222> LOCATION: (215)..(216)
<223> OTHER INFORMATION: Xaa can be any amino acid
<220> FEATURE:
<221> NAME/KEY: misc_feature
<222> LOCATION: (218)..(266)
<223> OTHER INFORMATION: Xaa, if present, can be any amino acid
<220> FEATURE:
<221> NAME/KEY: misc_feature
<222> LOCATION: (268)..(269)
<223> OTHER INFORMATION: Xaa can be any amino acid
<220> FEATURE:
<221> NAME/KEY: misc_feature
<222> LOCATION: (273)..(274)
<223> OTHER INFORMATION: Xaa can be any amino acid
<220> FEATURE:
<221> NAME/KEY: misc_feature
<222> LOCATION: (276)..(279)
<223> OTHER INFORMATION: Xaa can be any amino acid

<400> SEQUENCE: 117

Pro Xaa Xaa Pro Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Pro Xaa Xaa Pro Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

```
Xaa Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Tyr Xaa Xaa Leu Xaa Xaa
        100                 105                 110

Xaa Xaa Xaa Xaa Xaa Xaa Xaa Xaa Xaa Xaa Xaa Xaa Xaa Xaa Xaa Xaa
    115                 120                 125

Xaa Xaa Xaa Xaa Xaa Xaa Xaa Xaa Xaa Xaa Xaa Xaa Xaa Xaa Xaa Xaa
130                 135                 140

Xaa Xaa Xaa Xaa Xaa Xaa Xaa Xaa Xaa Xaa Xaa Xaa Xaa Xaa Xaa Pro
145                 150                 155                 160

Xaa Xaa Pro Glu Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa Xaa Xaa Xaa
    195                 200                 205

Xaa Xaa Xaa Xaa Xaa Tyr Xaa Xaa Leu Xaa Xaa Xaa Xaa Xaa Xaa Xaa
210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Pro Xaa Xaa Pro Asp Tyr
                260                 265                 270

Xaa Xaa Leu Xaa Xaa Xaa Xaa
        275

<210> SEQ ID NO 118
<211> LENGTH: 41
<212> TYPE: PRT
<213> ORGANISM: Artificial Sequence
<220> FEATURE:
<223> OTHER INFORMATION: mutated derivative of CD domain
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (6)..(8)
<223> OTHER INFORMATION: Xaa can be any amino acid
<220> FEATURE:
<221> NAME/KEY: misc_feature
<222> LOCATION: (10)..(10)
<223> OTHER INFORMATION: Xaa can be any amino acid
<220> FEATURE:
<221> NAME/KEY: misc_feature
<222> LOCATION: (14)..(14)
<223> OTHER INFORMATION: Xaa can be any amino acid
<220> FEATURE:
<221> NAME/KEY: misc_feature
<222> LOCATION: (17)..(18)
<223> OTHER INFORMATION: Xaa can be any amino acid
<220> FEATURE:
<221> NAME/KEY: misc_feature
<222> LOCATION: (20)..(20)
<223> OTHER INFORMATION: Xaa can be any amino acid
<220> FEATURE:
<221> NAME/KEY: misc_feature
<222> LOCATION: (22)..(23)
<223> OTHER INFORMATION: Xaa can be any amino acid
<220> FEATURE:
<221> NAME/KEY: misc_feature
<222> LOCATION: (26)..(26)
<223> OTHER INFORMATION: Xaa can be any amino acid
<220> FEATURE:
```

```
<221> NAME/KEY: misc_feature
<222> LOCATION: (28)..(29)
<223> OTHER INFORMATION: Xaa can be any amino acid
<220> FEATURE:
<221> NAME/KEY: misc_feature
<222> LOCATION: (31)..(31)
<223> OTHER INFORMATION: Xaa can be any amino acid
<220> FEATURE:
<221> NAME/KEY: misc_feature
<222> LOCATION: (33)..(34)
<223> OTHER INFORMATION: Xaa can be any amino acid
<220> FEATURE:
<221> NAME/KEY: misc_feature
<222> LOCATION: (38)..(39)
<223> OTHER INFORMATION: Xaa can be any amino acid

<400> SEQUENCE: 118

Pro Xaa Xaa Pro Glu Xaa Xaa Xaa Pro Xaa Lys Pro Asp Xaa Asp Tyr
1               5                   10                  15

Xaa Xaa Leu Xaa Pro Xaa Xaa Pro Glu Xaa Tyr Xaa Xaa Leu Xaa Pro
            20                  25                  30

Xaa Xaa Pro Asp Tyr Xaa Xaa Leu Arg
        35                  40

<210> SEQ ID NO 119
<211> LENGTH: 279
<212> TYPE: PRT
<213> ORGANISM: Artificial Sequence
<220> FEATURE:
<223> OTHER INFORMATION: mutated derivative of CD domain
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (6)..(54)
<223> OTHER INFORMATION: Xaa, if present, can be any amino acid
<220> FEATURE:
<221> NAME/KEY: misc_feature
<222> LOCATION: (56)..(56)
<223> OTHER INFORMATION: Xaa can be any amino acid
<220> FEATURE:
<221> NAME/KEY: misc_feature
<222> LOCATION: (60)..(108)
<223> OTHER INFORMATION: Xaa, if present, can be any amino acid
<220> FEATURE:
<221> NAME/KEY: misc_feature
<222> LOCATION: (111)..(112)
<223> OTHER INFORMATION: Xaa can be any amino acid
<220> FEATURE:
<221> NAME/KEY: misc_feature
<222> LOCATION: (114)..(162)
<223> OTHER INFORMATION: Xaa, if present, can be any amino acid
<220> FEATURE:
<221> NAME/KEY: misc_feature
<222> LOCATION: (164)..(165)
<223> OTHER INFORMATION: Xaa can be any amino acid
<220> FEATURE:
<221> NAME/KEY: misc_feature
<222> LOCATION: (168)..(216)
<223> OTHER INFORMATION: Xaa, if present, can be any amino acid
<220> FEATURE:
<221> NAME/KEY: misc_feature
<222> LOCATION: (218)..(219)
<223> OTHER INFORMATION: Xaa can be any amino acid
<220> FEATURE:
<221> NAME/KEY: misc_feature
<222> LOCATION: (221)..(269)
<223> OTHER INFORMATION: Xaa, if present, can be any amino acid
<220> FEATURE:
<221> NAME/KEY: misc_feature
<222> LOCATION: (271)..(272)
<223> OTHER INFORMATION: Xaa can be any amino acid
<220> FEATURE:
```

<221> NAME/KEY: misc_feature
<222> LOCATION: (276)..(277)
<223> OTHER INFORMATION: Xaa can be any amino acid

<400> SEQUENCE: 119

Pro Xaa Xaa Pro Glu Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Pro Xaa Lys Pro Asp Xaa Xaa Xaa Xaa
50                          55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Asp Tyr Xaa Xaa
                100                 105                 110

Leu Xaa Xaa Xaa Xaa Xaa Xaa Xaa Xaa Xaa Xaa Xaa Xaa Xaa
    115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160

Xaa Xaa Pro Xaa Xaa Pro Glu Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Tyr Xaa Xaa Leu Xaa Xaa Xaa Xaa
        210                 215                 220

Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
            245                 250                 255

Xaa Xaa Xaa Xaa Xaa Xaa Xaa Xaa Xaa Xaa Xaa Pro Xaa Xaa
            260                 265                 270

Pro Asp Tyr Xaa Xaa Leu Arg
        275

<210> SEQ ID NO 120
<211> LENGTH: 45
<212> TYPE: PRT
<213> ORGANISM: Artificial Sequence
<220> FEATURE:
<223> OTHER INFORMATION: mutated derivative of CD domain
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (6)..(8)
<223> OTHER INFORMATION: Xaa can be any amino acid
<220> FEATURE:
<221> NAME/KEY: misc_feature
<222> LOCATION: (10)..(10)
<223> OTHER INFORMATION: Xaa can be any amino acid

```
<220> FEATURE:
<221> NAME/KEY: misc_feature
<222> LOCATION: (14)..(14)
<223> OTHER INFORMATION: Xaa can be any amino acid
<220> FEATURE:
<221> NAME/KEY: misc_feature
<222> LOCATION: (17)..(18)
<223> OTHER INFORMATION: Xaa can be any amino acid
<220> FEATURE:
<221> NAME/KEY: misc_feature
<222> LOCATION: (20)..(20)
<223> OTHER INFORMATION: Xaa can be any amino acid
<220> FEATURE:
<221> NAME/KEY: misc_feature
<222> LOCATION: (22)..(23)
<223> OTHER INFORMATION: Xaa can be any amino acid
<220> FEATURE:
<221> NAME/KEY: misc_feature
<222> LOCATION: (26)..(26)
<223> OTHER INFORMATION: Xaa can be any amino acid
<220> FEATURE:
<221> NAME/KEY: misc_feature
<222> LOCATION: (28)..(29)
<223> OTHER INFORMATION: Xaa can be any amino acid
<220> FEATURE:
<221> NAME/KEY: misc_feature
<222> LOCATION: (31)..(31)
<223> OTHER INFORMATION: Xaa can be any amino acid
<220> FEATURE:
<221> NAME/KEY: misc_feature
<222> LOCATION: (33)..(34)
<223> OTHER INFORMATION: Xaa can be any amino acid
<220> FEATURE:
<221> NAME/KEY: misc_feature
<222> LOCATION: (38)..(39)
<223> OTHER INFORMATION: Xaa can be any amino acid
<220> FEATURE:
<221> NAME/KEY: misc_feature
<222> LOCATION: (42)..(45)
<223> OTHER INFORMATION: Xaa can be any amino acid

<400> SEQUENCE: 120

Pro Xaa Xaa Pro Glu Xaa Xaa Xaa Pro Xaa Lys Pro Asp Xaa Asp Tyr
1               5                   10                  15

Xaa Xaa Leu Xaa Pro Xaa Xaa Pro Glu Xaa Tyr Xaa Xaa Leu Xaa Pro
            20                  25                  30

Xaa Xaa Pro Asp Tyr Xaa Xaa Leu Arg Xaa Xaa Xaa Xaa
        35                  40                  45

<210> SEQ ID NO 121
<211> LENGTH: 283
<212> TYPE: PRT
<213> ORGANISM: Artificial Sequence
<220> FEATURE:
<223> OTHER INFORMATION: mutated derivative of CD domain
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (6)..(54)
<223> OTHER INFORMATION: Xaa, if present, can be any amino acid
<220> FEATURE:
<221> NAME/KEY: misc_feature
<222> LOCATION: (56)..(56)
<223> OTHER INFORMATION: Xaa can be any amino acid
<220> FEATURE:
<221> NAME/KEY: misc_feature
<222> LOCATION: (60)..(108)
<223> OTHER INFORMATION: Xaa, if present, can be any amino acid
<220> FEATURE:
<221> NAME/KEY: misc_feature
<222> LOCATION: (111)..(112)
<223> OTHER INFORMATION: Xaa can be any amino acid
```

```
<220> FEATURE:
<221> NAME/KEY: misc_feature
<222> LOCATION: (114)..(162)
<223> OTHER INFORMATION: Xaa, if present, can be any amino acid
<220> FEATURE:
<221> NAME/KEY: misc_feature
<222> LOCATION: (164)..(165)
<223> OTHER INFORMATION: Xaa can be any amino acid
<220> FEATURE:
<221> NAME/KEY: misc_feature
<222> LOCATION: (168)..(216)
<223> OTHER INFORMATION: Xaa, if present, can be any amino acid
<220> FEATURE:
<221> NAME/KEY: misc_feature
<222> LOCATION: (218)..(219)
<223> OTHER INFORMATION: Xaa can be any amino acid
<220> FEATURE:
<221> NAME/KEY: misc_feature
<222> LOCATION: (221)..(269)
<223> OTHER INFORMATION: Xaa, if present, can be any amino acid
<220> FEATURE:
<221> NAME/KEY: misc_feature
<222> LOCATION: (271)..(272)
<223> OTHER INFORMATION: Xaa can be any amino acid
<220> FEATURE:
<221> NAME/KEY: misc_feature
<222> LOCATION: (276)..(277)
<223> OTHER INFORMATION: Xaa can be any amino acid
<220> FEATURE:
<221> NAME/KEY: misc_feature
<222> LOCATION: (280)..(283)
<223> OTHER INFORMATION: Xaa can be any amino acid

<400> SEQUENCE: 121

Pro Xaa Xaa Pro Glu Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa
             35                  40                  45

Xaa Xaa Xaa Xaa Xaa Xaa Pro Xaa Lys Pro Asp Xaa Xaa Xaa Xaa
         50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
             85                  90                  95

Xaa Xaa Xaa Xaa Xaa Xaa Xaa Xaa Xaa Xaa Xaa Asp Tyr Xaa Xaa
            100                 105                 110

Leu Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa Xaa
            130                 135                 140

Xaa Xaa Xaa Xaa Xaa Xaa Xaa Xaa Xaa Xaa Xaa Xaa Xaa Xaa Xaa
145                 150                 155                 160

Xaa Xaa Pro Xaa Xaa Pro Glu Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
            195                 200                 205

Xaa Xaa Xaa Xaa Xaa Xaa Xaa Tyr Xaa Xaa Leu Xaa Xaa Xaa Xaa
            210                 215                 220

Xaa Xaa Xaa Xaa Xaa Xaa Xaa Xaa Xaa Xaa Xaa Xaa Xaa Xaa Xaa
225                 230                 235                 240
```

```
Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Pro Xaa Xaa
                260                 265                 270

Pro Asp Tyr Xaa Xaa Leu Arg Xaa Xaa Xaa Xaa
        275                 280

<210> SEQ ID NO 122
<211> LENGTH: 40
<212> TYPE: PRT
<213> ORGANISM: Artificial Sequence
<220> FEATURE:
<223> OTHER INFORMATION: mutated derivative of CD domain
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (5)..(8)
<223> OTHER INFORMATION: Xaa can be any amino acid
<220> FEATURE:
<221> NAME/KEY: misc_feature
<222> LOCATION: (10)..(11)
<223> OTHER INFORMATION: Xaa can be any amino acid
<220> FEATURE:
<221> NAME/KEY: misc_feature
<222> LOCATION: (13)..(13)
<223> OTHER INFORMATION: Xaa can be any amino acid
<220> FEATURE:
<221> NAME/KEY: misc_feature
<222> LOCATION: (15)..(15)
<223> OTHER INFORMATION: Xaa can be any amino acid
<220> FEATURE:
<221> NAME/KEY: misc_feature
<222> LOCATION: (17)..(18)
<223> OTHER INFORMATION: Xaa can be any amino acid
<220> FEATURE:
<221> NAME/KEY: misc_feature
<222> LOCATION: (20)..(20)
<223> OTHER INFORMATION: Xaa can be any amino acid
<220> FEATURE:
<221> NAME/KEY: misc_feature
<222> LOCATION: (22)..(23)
<223> OTHER INFORMATION: Xaa can be any amino acid
<220> FEATURE:
<221> NAME/KEY: misc_feature
<222> LOCATION: (26)..(26)
<223> OTHER INFORMATION: Xaa can be any amino acid
<220> FEATURE:
<221> NAME/KEY: misc_feature
<222> LOCATION: (28)..(29)
<223> OTHER INFORMATION: Xaa can be any amino acid
<220> FEATURE:
<221> NAME/KEY: misc_feature
<222> LOCATION: (31)..(31)
<223> OTHER INFORMATION: Xaa can be any amino acid
<220> FEATURE:
<221> NAME/KEY: misc_feature
<222> LOCATION: (33)..(34)
<223> OTHER INFORMATION: Xaa can be any amino acid
<220> FEATURE:
<221> NAME/KEY: misc_feature
<222> LOCATION: (38)..(39)
<223> OTHER INFORMATION: Xaa can be any amino acid

<400> SEQUENCE: 122

Pro Xaa Xaa Pro Xaa Xaa Xaa Xaa Pro Xaa Xaa Pro Xaa Ser Xaa Tyr
1               5                   10                  15

Xaa Xaa Leu Xaa Pro Xaa Xaa Pro Glu Xaa Tyr Xaa Xaa Leu Xaa Pro
            20                  25                  30

Xaa Xaa Pro Asp Tyr Xaa Xaa Leu
```

-continued

```
                    35                  40

<210> SEQ ID NO 123
<211> LENGTH: 277
<212> TYPE: PRT
<213> ORGANISM: Artificial Sequence
<220> FEATURE:
<223> OTHER INFORMATION: mutated derivative of CD domain
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (5)..(53)
<223> OTHER INFORMATION: Xaa, if present, can be any amino acid
<220> FEATURE:
<221> NAME/KEY: misc_feature
<222> LOCATION: (55)..(56)
<223> OTHER INFORMATION: Xaa can be any amino acid
<220> FEATURE:
<221> NAME/KEY: misc_feature
<222> LOCATION: (58)..(106)
<223> OTHER INFORMATION: Xaa, if present, can be any amino acid
<220> FEATURE:
<221> NAME/KEY: misc_feature
<222> LOCATION: (108)..(108)
<223> OTHER INFORMATION: Xaa can be any amino acid
<220> FEATURE:
<221> NAME/KEY: misc_feature
<222> LOCATION: (110)..(111)
<223> OTHER INFORMATION: Xaa can be any amino acid
<220> FEATURE:
<221> NAME/KEY: misc_feature
<222> LOCATION: (113)..(161)
<223> OTHER INFORMATION: Xaa, if present, can be any amino acid
<220> FEATURE:
<221> NAME/KEY: misc_feature
<222> LOCATION: (163)..(164)
<223> OTHER INFORMATION: Xaa can be any amino acid
<220> FEATURE:
<221> NAME/KEY: misc_feature
<222> LOCATION: (167)..(215)
<223> OTHER INFORMATION: Xaa, if present, can be any amino acid
<220> FEATURE:
<221> NAME/KEY: misc_feature
<222> LOCATION: (217)..(218)
<223> OTHER INFORMATION: Xaa can be any amino acid
<220> FEATURE:
<221> NAME/KEY: misc_feature
<222> LOCATION: (220)..(268)
<223> OTHER INFORMATION: Xaa, if present, can be any amino acid
<220> FEATURE:
<221> NAME/KEY: misc_feature
<222> LOCATION: (270)..(271)
<223> OTHER INFORMATION: Xaa can be any amino acid
<220> FEATURE:
<221> NAME/KEY: misc_feature
<222> LOCATION: (275)..(276)
<223> OTHER INFORMATION: Xaa can be any amino acid

<400> SEQUENCE: 123

Pro Xaa Xaa Pro Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Pro Xaa Xaa Pro Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80
```

```
Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Ser Xaa Tyr Xaa Xaa Leu
            100                 105                 110

Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa
        130                 135                 140

Xaa Xaa Xaa Xaa Xaa Xaa Xaa Xaa Xaa Xaa Xaa Xaa Xaa Xaa Xaa Xaa
145                 150                 155                 160

Xaa Pro Xaa Xaa Pro Glu Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Tyr Xaa Xaa Leu Xaa Xaa Xaa Xaa Xaa
        210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa
            245                 250                 255

Xaa Xaa Xaa Xaa Xaa Xaa Xaa Xaa Xaa Pro Xaa Xaa Pro
            260                 265                 270

Asp Tyr Xaa Xaa Leu
        275

<210> SEQ ID NO 124
<211> LENGTH: 44
<212> TYPE: PRT
<213> ORGANISM: Artificial Sequence
<220> FEATURE:
<223> OTHER INFORMATION: mutated derivative of CD domain
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (5)..(8)
<223> OTHER INFORMATION: Xaa can be any amino acid
<220> FEATURE:
<221> NAME/KEY: misc_feature
<222> LOCATION: (10)..(11)
<223> OTHER INFORMATION: Xaa can be any amino acid
<220> FEATURE:
<221> NAME/KEY: misc_feature
<222> LOCATION: (13)..(13)
<223> OTHER INFORMATION: Xaa can be any amino acid
<220> FEATURE:
<221> NAME/KEY: misc_feature
<222> LOCATION: (15)..(15)
<223> OTHER INFORMATION: Xaa can be any amino acid
<220> FEATURE:
<221> NAME/KEY: misc_feature
<222> LOCATION: (17)..(18)
<223> OTHER INFORMATION: Xaa can be any amino acid
<220> FEATURE:
<221> NAME/KEY: misc_feature
<222> LOCATION: (20)..(20)
<223> OTHER INFORMATION: Xaa can be any amino acid
<220> FEATURE:
<221> NAME/KEY: misc_feature
<222> LOCATION: (22)..(23)
<223> OTHER INFORMATION: Xaa can be any amino acid
<220> FEATURE:
```

```
<221> NAME/KEY: misc_feature
<222> LOCATION: (26)..(26)
<223> OTHER INFORMATION: Xaa can be any amino acid
<220> FEATURE:
<221> NAME/KEY: misc_feature
<222> LOCATION: (28)..(29)
<223> OTHER INFORMATION: Xaa can be any amino acid
<220> FEATURE:
<221> NAME/KEY: misc_feature
<222> LOCATION: (31)..(31)
<223> OTHER INFORMATION: Xaa can be any amino acid
<220> FEATURE:
<221> NAME/KEY: misc_feature
<222> LOCATION: (33)..(34)
<223> OTHER INFORMATION: Xaa can be any amino acid
<220> FEATURE:
<221> NAME/KEY: misc_feature
<222> LOCATION: (38)..(39)
<223> OTHER INFORMATION: Xaa can be any amino acid
<220> FEATURE:
<221> NAME/KEY: misc_feature
<222> LOCATION: (41)..(44)
<223> OTHER INFORMATION: Xaa can be any amino acid

<400> SEQUENCE: 124

Pro Xaa Xaa Pro Xaa Xaa Xaa Xaa Pro Xaa Xaa Pro Xaa Ser Xaa Tyr
1               5                   10                  15

Xaa Xaa Leu Xaa Pro Xaa Xaa Pro Glu Xaa Tyr Xaa Xaa Leu Xaa Pro
            20                  25                  30

Xaa Xaa Pro Asp Tyr Xaa Xaa Leu Xaa Xaa Xaa Xaa
            35                  40

<210> SEQ ID NO 125
<211> LENGTH: 281
<212> TYPE: PRT
<213> ORGANISM: Artificial Sequence
<220> FEATURE:
<223> OTHER INFORMATION: mutated derivative of CD domain
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (5)..(53)
<223> OTHER INFORMATION: Xaa, if present, can be any amino acid
<220> FEATURE:
<221> NAME/KEY: misc_feature
<222> LOCATION: (55)..(56)
<223> OTHER INFORMATION: Xaa can be any amino acid
<220> FEATURE:
<221> NAME/KEY: misc_feature
<222> LOCATION: (58)..(106)
<223> OTHER INFORMATION: Xaa, if present, can be any amino acid
<220> FEATURE:
<221> NAME/KEY: misc_feature
<222> LOCATION: (108)..(108)
<223> OTHER INFORMATION: Xaa can be any amino acid
<220> FEATURE:
<221> NAME/KEY: misc_feature
<222> LOCATION: (110)..(111)
<223> OTHER INFORMATION: Xaa can be any amino acid
<220> FEATURE:
<221> NAME/KEY: misc_feature
<222> LOCATION: (113)..(161)
<223> OTHER INFORMATION: Xaa, if present, can be any amino acid
<220> FEATURE:
<221> NAME/KEY: misc_feature
<222> LOCATION: (163)..(164)
<223> OTHER INFORMATION: Xaa can be any amino acid
<220> FEATURE:
<221> NAME/KEY: misc_feature
<222> LOCATION: (167)..(215)
<223> OTHER INFORMATION: Xaa, if present, can be any amino acid
<220> FEATURE:
```

```
<221> NAME/KEY: misc_feature
<222> LOCATION: (217)..(218)
<223> OTHER INFORMATION: Xaa can be any amino acid
<220> FEATURE:
<221> NAME/KEY: misc_feature
<222> LOCATION: (220)..(268)
<223> OTHER INFORMATION: Xaa, if present, can be any amino acid
<220> FEATURE:
<221> NAME/KEY: misc_feature
<222> LOCATION: (270)..(271)
<223> OTHER INFORMATION: Xaa can be any amino acid
<220> FEATURE:
<221> NAME/KEY: misc_feature
<222> LOCATION: (275)..(276)
<223> OTHER INFORMATION: Xaa can be any amino acid
<220> FEATURE:
<221> NAME/KEY: misc_feature
<222> LOCATION: (278)..(281)
<223> OTHER INFORMATION: Xaa can be any amino acid

<400> SEQUENCE: 125

Pro Xaa Xaa Pro Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Pro Xaa Xaa Pro Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Ser Xaa Tyr Xaa Xaa Leu
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160

Xaa Pro Xaa Xaa Pro Glu Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Tyr Xaa Xaa Leu Xaa Xaa Xaa Xaa
    210                 215                 220

Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Pro Xaa Xaa Pro
            260                 265                 270

Asp Tyr Xaa Xaa Leu Xaa Xaa Xaa Xaa
            275                 280

<210> SEQ ID NO 126
<211> LENGTH: 13
```

```
<212> TYPE: PRT
<213> ORGANISM: Bovine leukemia virus

<400> SEQUENCE: 126

Lys Cys Leu Thr Ser Arg Leu Leu Lys Leu Leu Arg Gln
1               5                   10

<210> SEQ ID NO 127
<211> LENGTH: 4
<212> TYPE: PRT
<213> ORGANISM: Artificial Sequence
<220> FEATURE:
<223> OTHER INFORMATION: motif of CD domain
<220> FEATURE:
<221> NAME/KEY: misc_feature
<222> LOCATION: (2)..(3)
<223> OTHER INFORMATION: Xaa can be any amino acid

<400> SEQUENCE: 127

Tyr Xaa Xaa Leu
1

<210> SEQ ID NO 128
<211> LENGTH: 5
<212> TYPE: PRT
<213> ORGANISM: Artificial Sequence
<220> FEATURE:
<223> OTHER INFORMATION: motif of CD domain
<220> FEATURE:
<221> NAME/KEY: misc_feature
<222> LOCATION: (3)..(4)
<223> OTHER INFORMATION: Xaa can be any amino acid

<400> SEQUENCE: 128

Asp Tyr Xaa Xaa Leu
1               5

<210> SEQ ID NO 129
<211> LENGTH: 4
<212> TYPE: PRT
<213> ORGANISM: Artificial Sequence
<220> FEATURE:
<223> OTHER INFORMATION: motif of CD domain
<220> FEATURE:
<221> NAME/KEY: misc_feature
<222> LOCATION: (2)..(3)
<223> OTHER INFORMATION: Xaa can be any amino acid

<400> SEQUENCE: 129

Pro Xaa Xaa Pro
1

<210> SEQ ID NO 130
<211> LENGTH: 4
<212> TYPE: PRT
<213> ORGANISM: Artificial Sequence
<220> FEATURE:
<223> OTHER INFORMATION: motif of CD domain
<220> FEATURE:
<221> NAME/KEY: misc_feature
<222> LOCATION: (2)..(3)
<223> OTHER INFORMATION: Xaa can be any amino acid

<400> SEQUENCE: 130

Tyr Xaa Xaa Phe
1

<210> SEQ ID NO 131
<211> LENGTH: 5
```

```
<212> TYPE: PRT
<213> ORGANISM: Artificial Sequence
<220> FEATURE:
<223> OTHER INFORMATION: motif of CD domain
<220> FEATURE:
<221> NAME/KEY: misc_feature
<222> LOCATION: (3)..(4)
<223> OTHER INFORMATION: Xaa can be any amino acid

<400> SEQUENCE: 131

Asp Tyr Xaa Xaa Phe
1               5
```

The invention claimed is:

1. A membrane vesicle comprising a chimeric polypeptide, wherein said chimeric polypeptide comprises or consists of the following domains:
   (i) a peptide or polypeptide of interest;
   (ii) a transmembrane domain having the capacity to anchor in the lipid bilayer of a cell membrane; and
   (iii) a mutated cytoplasmic domain (CD) of the transmembrane protein (TM) of the Bovine Leukaemia Virus (BLV), wherein a sequence of the mutated cytoplasmic domain comprises or consists of the sequence SEQ ID NO: 12, wherein said mutated cytoplasmic domain has the capacity of addressing of said chimeric polypeptide to membrane vesicles and/or to the cell compartment(s) involved in the formation of said membrane vesicles, and wherein the sequence of said mutated cytoplasmic domain is a 45-80 amino acid sequence.

2. The membrane vesicle of claim 1, which is an exosome.

3. The membrane vesicle of claim 1, wherein the peptide or polypeptide of interest is exposed, partly or completely, on the outside of said membrane vesicle.

4. An immunogenic composition, which comprises one or several membrane vesicle(s) of claim 1.

5. The immunogenic composition of claim 4, which is a drug.

6. The immunogenic composition of claim 4 or 5, which is a drug for the prophylaxis and/or treatment of a bacterial, viral or parasitic infection, or of a tumour, by induction or stimulation of a humoral and/or cellular response against said tumour, virus, bacterium or parasite.

7. A recombinant exosome-producing cell, which comprises or has absorbed a membrane vesicle according to claim 1.

8. A method for in vitro production of membrane vesicles, which comprises bringing an exosome-producing cell into contact with one or several membrane vesicle(s) according to claim 1;
   a) growing said exosome-producing cell; and
   b) recovering the membrane vesicles produced by said exosome-producing cell.

9. The method of claim 8, which further comprises an intermediate step between steps a) and b), during which said cell is selected and/or stimulated to induce and/or increase the secretion of exosomes or to induce a specificity in the composition of the exosomes in certain cellular proteins.

10. A method for preparing a polyclonal serum directed against one or several antigenic peptide(s) or polypeptide(s) of interest expressed on the surface of membrane vesicles, comprising the following steps:
    a) administering to a non-human animal, the membrane vesicle of claim 1, or the immunogenic composition of claim 4, associated or not with an adjuvant, to induce the production of antibodies by said non-human animal; and
    b) recovering from said non-human animal the antibodies, which bind to said antigenic peptide(s) or polypeptide(s) of interest.

11. A method for preparing monoclonal antibodies directed against one or several antigenic peptide(s) or polypeptide(s) expressed on the surface of membrane vesicles, comprising the following steps:
    a) fusing, with myeloma cells, spleen cells previously obtained from a host to which the membrane vesicle of claim 1, or the immunogenic composition of claim 4 has been administered to produce hybridomas;
    b) growing said hybridomas under conditions allowing the production of antibodies;
    c) recovering the monoclonal antibodies, which are directed against said antigenic peptide(s) or polypeptide(s) of interest.

12. The membrane vesicle of claim 1, wherein the sequence of the mutated cytoplasmic domain is a 45-60 amino acid sequence.

13. The membrane vesicle of claim 1, wherein the sequence of the mutated cytoplasmic domain is devoid of the sequence KCLTSRLLKLLRQ (SEQ ID NO: 126).

14. The membrane vesicle of claim 1, wherein said peptide or polypeptide of interest (i) comprises or consists of
    one or several domain(s) of an extracellular protein; or
    one or several cytoplasmic domain(s) of a transmembrane protein; or
    one or several domain(s) of a cytosolic protein.

15. The membrane vesicle of claim 1, wherein said peptide or polypeptide of interest (i) is a viral peptide or polypeptide, or a bacterial peptide or polypeptide, or a tumor antigen.

16. The membrane vesicle of claim 1, wherein said peptide or polypeptide of interest (i) is
    the ectodomain of the haemagglutinin (HA) of an influenza virus, or a fragment comprising or consisting of one or several epitope(s) of said ectodomain; or
    the ectodomain of the HA protein of the H5N1 avian influenza virus, or a fragment comprising or consisting of one or several epitope(s) of said ectodomain; or
    the ectodomain of the Spike protein of a coronavirus of severe acute respiratory syndrome (SARS) or a fragment comprising or consisting of one or several epitope(s) of said ectodomain.

17. The membrane vesicle of claim 1, wherein said transmembrane domain (ii) is the transmembrane domain of the membrane protein of a virus, a bacterium or a tumor; or is a mutated derivative of said transmembrane domain, wherein said mutated derivative of transmembrane domain is defined by substitution, deletion and/or insertion of one or several residue(s) in the sequence of said transmembrane domain and by the capacity to anchor in the lipid bilayer of a cell membrane, and wherein the sequence of said mutated derivative of transmembrane domain consists of 10-50 amino acids and is at least 80% identical to the sequence of said transmembrane domain.

18. The membrane vesicle of claim 1, wherein said peptide or the polypeptide of interest (i) and said transmembrane domain (ii) are not fragments of the same protein.

19. The membrane vesicle of claim 1, wherein said chimeric polypeptide further comprises at least one linker linking two of said domains (i), (ii) and (iii).

20. The recombinant exosome-producing cell of claim 7, which is a cell of the immune system.

21. The recombinant exosome-producing cell of claim 7, which is a lymphocyte.

* * * * *